United States Patent
Busch et al.

Patent Number: 5,246,868
Date of Patent: Sep. 21, 1993

[54] INFRARED EMISSION DETECTION

[75] Inventors: Kenneth W. Busch, Waco, Tex.; M. Keith Hudson, Little Rock, Ark.; Marianna A. Busch, Waco, Tex.; Sidney W. Kubala, Jr., Hewitt, Tex.; David C. Tilotta, Waco, Tex.; Christopher K. Y. Lam, Waco, Tex.; Ravishankar Srinivasan, Waco, Tex.

[73] Assignee: Research Corporation Technologies, Inc., Tucson, Ariz.

[21] Appl. No.: 415,141

[22] Filed: Sep. 29, 1989

Related U.S. Application Data

[63] Continuation-in-part of Ser. No. 263,089, Oct. 26, 1988, abandoned, which is a continuation-in-part of Ser. No. 120,050, Oct. 26, 1987, abandoned.

[51] Int. Cl.$^5$ .......................................... G01N 21/72
[52] U.S. Cl. .................................. 436/101; 436/124; 436/133; 436/143; 436/146; 436/160; 436/171; 422/80; 422/82.05; 356/315
[58] Field of Search .............. 250/339, 338.4, 338.1; 356/311, 315, 316, 317; 436/155, 143, 171, 146, 133, 101, 124, 160; 422/82.05, 94, 78, 80, 54

[56] References Cited

U.S. PATENT DOCUMENTS

| | | | |
|---|---|---|---|
| 3,696,247 | 10/1972 | McIntosh et al. | 250/343 X |
| 3,854,881 | 12/1974 | Cohen | 436/146 X |
| 4,730,925 | 3/1988 | Chiba et al. | 356/315 X |
| 4,849,636 | 7/1989 | Fertig, Sr. | 250/343 |
| 5,153,673 | 10/1992 | Amirav | 356/315 |

FOREIGN PATENT DOCUMENTS 1332203  8/1987  U.S.S.R. .............. 356/315

OTHER PUBLICATIONS

Davidchuck, et al., "Unit for Investigating the Radiation Spectrum of the Combustion Products of Condensed Systems In the Range of 0.5-8 μM", *Combustion Explosion & Shock Waves*, vol. 10, No. 5, Sep. 1974, pp. 683-685.

Hylton, et al., "System for the Measurement of Spectral Emittance at High Temperature", AIAA Journal, vol. 14, No. 9, Sep. 1976, pp. 1303-1310.

Hergert, et al., "Remote Fourier Transform Infrared Air Pollution Studies", Optical Engineering, vol. 19, No. 4, Jul. 1980, pp. 508-514.

Plyler, et al., *J. Opt. Soc. Amer.* 1952 42 360.

Gaydon, A. G., *The Sepctroscopy of Flames*, Chapman and Hall: London 1974, pp. 221-243.

Gaydon, et al., *Flames, their Struction, Radiation and Temperature*, 4th Ed., Chapman and Hall: London 1979, pp. 238-259.

(List continued on next page.)

*Primary Examiner*—James C. Housel
*Assistant Examiner*—Jeffrey R. Snay
*Attorney, Agent, or Firm*—Scully, Scott, Murphy & Presser

[57] ABSTRACT

Apparatus and method for qualitatively and quantitatively analyzing infrared emission from excited molecules in samples of interest is disclosed. Over the wavelength interval from 1 to 5 um, two strong emission bands are observed with a PbSe detector when organic compounds are introduced into an hydrogen/air flame. The band at 4.3 um (2326 cm$^{-1}$ is due to the asymmetric stretch of carbon dioxide while the band at 2.7 um is due to both water and carbon dioxide emission. The carbon dioxide emission at 4.3 um is most intense at the tip of the flame, and increases with the amount of organic compound introduced into the flame. For chromatographic application, an optical filter can be used to isolate the 4.3 um emission band. The infrared emission detection system finds application in the determination of total inorganic carbon, chloride and available chlorine in aqueous samples. The detector is optimized by use of a dual beam system with background subtraction capabilities thereby eliminating background noise and the fluctuations therein.

42 Claims, 50 Drawing Sheets

OTHER PUBLICATIONS

Plyler, E. K., *J. Res. Nat. Bur. Stand.*, 1948 40 113.
Nakamoto, K., *Infrared Spectra of Inorganic and Coordination Compounds*, John Wiley, New York 1963, p. 77.
Curcio, et al., *Appl. Opt.*, 1966 5 231-233.
Putley, *Optical and Infrared Detectors*, Keyes (Ed.) Springer-Verlag, Berlin, 1980, Chp. 3.
Boyd, *Radiometry and the Detection of Optical Radiation*, John Wiley, New York 1983, Chp. 10.
Busch, et al., *Anal. Chem.*, 1974 46 1231.
Garrett, R. L., *J. Pet. Tech.*, Jun. 1978, p. 860.
Small, R. A., et al., *International Laboratory*, May 1986.
Bernard, *A Summary of TOC Developments*, Jun. 1985.
Small, *Pollution Engineering*, Sep. 1980, p. 53.
Capelle, et al., *Review of Scientific Instruments*, vol. 49, No. 8, Aug. 1978, pp. 1124-1129.
Karger, et al., *An Introduction to Separation Science*, Wiley, New York 1973, pp. 232-236.
Greenberg, et al., Eds, *Standard Methods for the Examination of Water and Wastewater*, American Public Health Association, Washington, D.C. 1985, pp. 286-294.
Manahan, S. E., *Environmental Chemistry*, 3rd E., Willard Grant Press, Boston, Mass. 1979, p. 29.

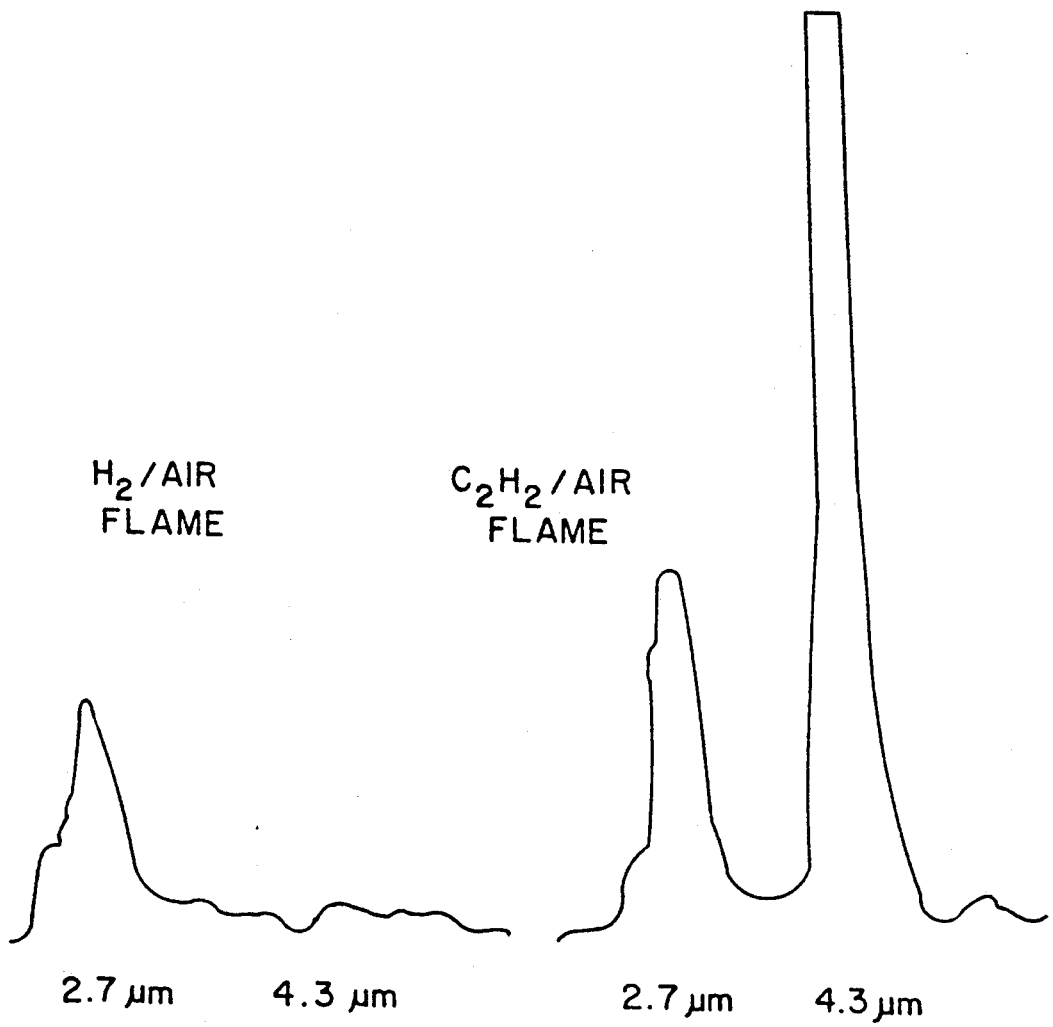

2.7 μm   4.3 μm

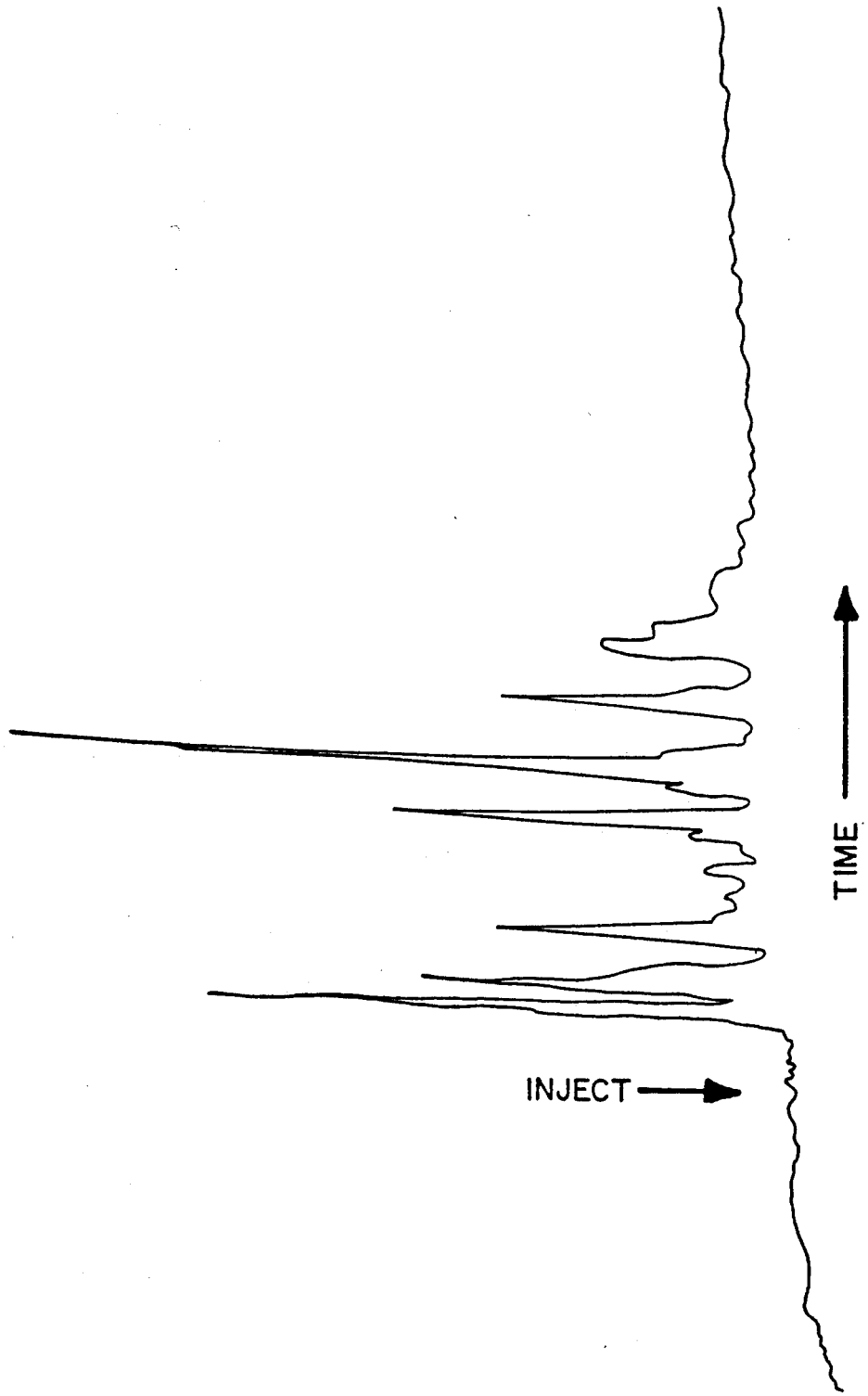

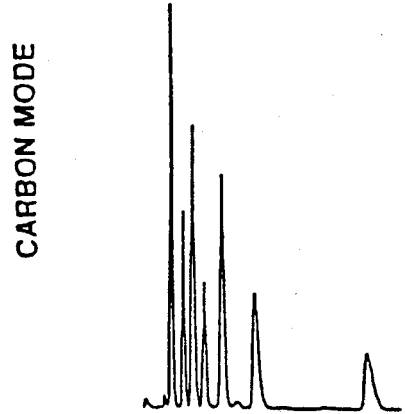 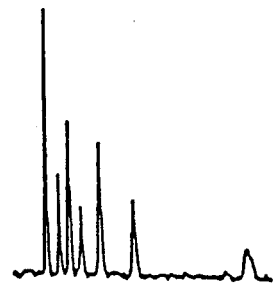
FIG.48C
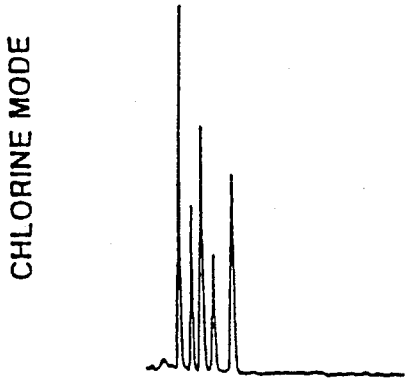 
FIG.48B
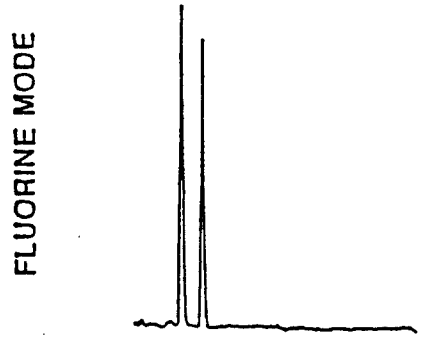 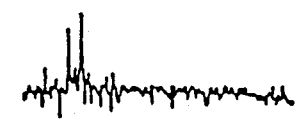
FIG.48A
SUBTRACED MODE UNSUBTRACED MODE

INFRARED EMISSION DETECTION

This application is a continuation-in-part of application Ser. No. 263,089 filed Oct. 26, 1988, now abandoned, which is a continuation-in-part of application Ser. No. 120,050, filed Oct. 26, 1987, now abandoned.

DESCRIPTION

1. Technical Field

This invention relates to infrared emission detection means and method for detecting selected molecules of interest in a gaseous sample or samples which can be converted to the gas phase. The invention is particularly applicable to the fields of gas chromatography, liquid chromatography, $CO_2$ detection, total organic carbon analysis, total inorganic carbon analysis, water analysis, environmental analysis, chlorofluorocarbon analysis, $SO_2$ analysis, process analysis and $NO_x$ analysis.

2. Prior Art

Combustion flames have long been employed analytically as spectroscopic sources. Although, the analytical application of combustion flames as spectroscopic sources has been studied in great depth, the work, to date, has been confined almost entirely to studies of the radiant emissions falling within the UV-visible region of the electromagnetic spectrum.

U.S. Pat. No. 3,836,255 describes a spectrometric substance analyzer which monitors both emission and absorption. In this analyzer a fluid is cyclically heated and cooled wherein the radiation variation is characteristic of the substance of interest in the fluid.

U.S. Pat. No. 3,516,745 describes a method for observation of gas spectral emissions. The gas is contained in a chamber where it is cyclically compressed and allowed to expand. The variation in infrared emission can be correlated to the concentration of gas within the piston. The oscillation excites or energizes the gas contained in the chamber to give off spectral emissions.

U.S. Pat. No. 3,749,495 like U.S. Pat. No. 3,516,745 describes an IR emission analyzer where the sample is periodically compressed and expanded. The compressed gas becomes heated due to increased molecular collision and thereby produces infrared emissions. Comparison of the emissions of the compressed and expanded gas produces a differential emission dependent upon gas concentration.

Despite the fact that a sizable fraction of the total radiation emitted from combustion flames lies in the infrared region of the spectrum, the use of this emission for analytical purposes does not appear to have been studied.

In terms of optical radiation, the energy radiated from a combustion flame extends from the ultraviolet region of the spectrum to the far infrared region. Of the total energy radiated by the flame, emission from the ultraviolet and visible regions of the spectrum accounts for only about 0.4% (Gaydon, A. G.; *The Spectroscopy of Flames;* Chapman and Hall: London, 1974; pp 221-243). By contrast, it is estimated that infrared emission from a combustion flame may account for as much as 20% of the total energy radiated (Gaydon, A. G.; Wolfhard, H. G.; *Flames, Their Structure, Radiation and Temperature,* 4th ed.; Chapman and Hall; London, 1979; pp. 238-259.) For transparent flames such as the hydrogen/air flame, the visible emission is negligible and most of the radiated energy falls in the infrared region of the spectrum. In spite of these facts, the analytical applications of infrared emissions from combustion flames have not been studied.

Despite the lack of analytical studies, a great deal of work has been done on the infrared emissions from hot gases, primarily for the purpose of tracking jet aircraft and ordinary combustion flames have been employed as models for exhaust gases from airborne vehicles. Plyler (Plyler, E. K.; *J. Res. Nat. Bur. Stand.* 1948, 40, 113.), in particular, has studied the infrared emission from a Bunsen flame over the wavelength range from 1 to 22 $\mu$m. In the wavelength interval from 1 to 5 $\mu$m, Plyler found that two bands predominate as a result of infrared emission from molecules of $CO_2$ and $H_2O$ (Plyler, E. K.; *J. Res. Nat. Bur. Stand.* 1948, 40, 113.). One band is located at 2.7 $\mu$m (3704 cm$^{-1}$) while the other is located at 4.3 $\mu$m (2326 cm$^{-1}$).

Studies of the infrared emission of carbon dioxide have shown that $CO_2$ emits strongly at 2.8 and 4.4 $\mu$m (Gaydon, A. G., *The Spectroscopy of Flames,* Chapman and Hall: London, 1974; pp 221-243.) The longer wavelength band corresponds to the asymmetric stretch of the carbon dioxide molecule (Nakamoto, K.; *Infrared Spectra of Inorganic and Coordination Compounds;* John Wiley: New York, 1963, p. 77.). Water, on the other hand, emits at 2.5 and 2.8 $\mu$m. The infrared spectrum observed from a typical combustion flame is a result of the superposition of these two emissions as modified by atmospheric absorption. Since the position of the $CO_2$ absorption band is shifted slightly with respect to the emission band, only a portion of the emission band undergoes atmospheric absorption (Curcio, J. A.; Buttrey, D. V. E.; *Appl. Opt.* 1966, 5, 231.). The observed band at 4.4 $\mu$m is due exclusively to carbon dioxide emission and appears shifted from the true 4.3 $\mu$m $CO_2$ emission due to an alteration in the true band shape by atmospheric absorption by $CO_2$. The band observed from the flame at 2.8 $\mu$m is a result of the overlap of the water bands at 2.5 and 2.7 $\mu$m with the carbon dioxide band at 2.7 $\mu$m and is also attenuated by atmospheric absorption by water vapor. Although other bands have been observed over the wavelength range from 1 to 22 $\mu$m, the bands at 2.7 and 4.3 $\mu$m are the two most intense emissions.

The amount of infrared emission observed from flames is also dependent on a number of other parameters. Studies of flames have shown that most of the energy is lost by conduction and convection occurring upon mixing with the cooler atmospheric air (Gaydon, A. G.; *The Spectroscopy of Flames;* Chapman and Hall: London, 1974; pp. 221-243.) In addition, turbulent flow has been observed to decrease the amount of infrared radiation emitteed (Gaydon, A. G.; Wolfhard, H. G.; *Flames, Their Structure, Radiation and Temperature,* 4th ed.; Chapman and Hall: London, 1979; pp. 238-259.). Self absorption is another factor which can reduce emission. Thus, the size, shape, and nature of the flame are important parameters when considering the amount of radiation from the flame.

In addition, the region of observation within the flame is an important consideration. Spatially, the emission of infrared radiation is observed to be a maximum in the outer cone and the surrounding gases with little or no emission from the inner conal area (Gaydon, A. G.; *The Spectroscopy of Flames; Chapman and Hall: London,* 1974; pp. 221-243.). Previous studies have shown that approximately one-seventh of the infrared emission comes from the inner conal area with the remaining six-sevenths originating in the outer cone/hot gas layer (Gaydon, A. G.; *The Spectroscopy of Flames;* Chapman and Hall: London, 1974; pp. 221-243.). The hot gaseous combustion products formed in the flame continue to emit above the visible portion of the outer cone until they are cooled by the entrainment of atmospheric air.

Finally, and most importantly from an analytical standpoint, the amount of infrared radiation emitted from the flame is a function of the number of $CO_2$ and $H_2O$ molecules present in the hot gases. Thus both quantitative and qualitative analyses are possible.

BRIEF DESCRIPTION OF THE DRAWINGS

FIGS. 11A to 11B are the infrared spectra obtained with the system for a hydrogen/air flame and an acetylene/air flame using the PbSe detector.

FIG. 18 is a chromatogram of 5 $\mu L$ of unleaded gasoline obtained on 10% OV-101. Column temperature was maintained at 55° C. for 4 minutes and then ramped to 200° C. over a period of 7 minutes.

addition of concentrated sulfuric acid to a bleach sample.

Figure 41:
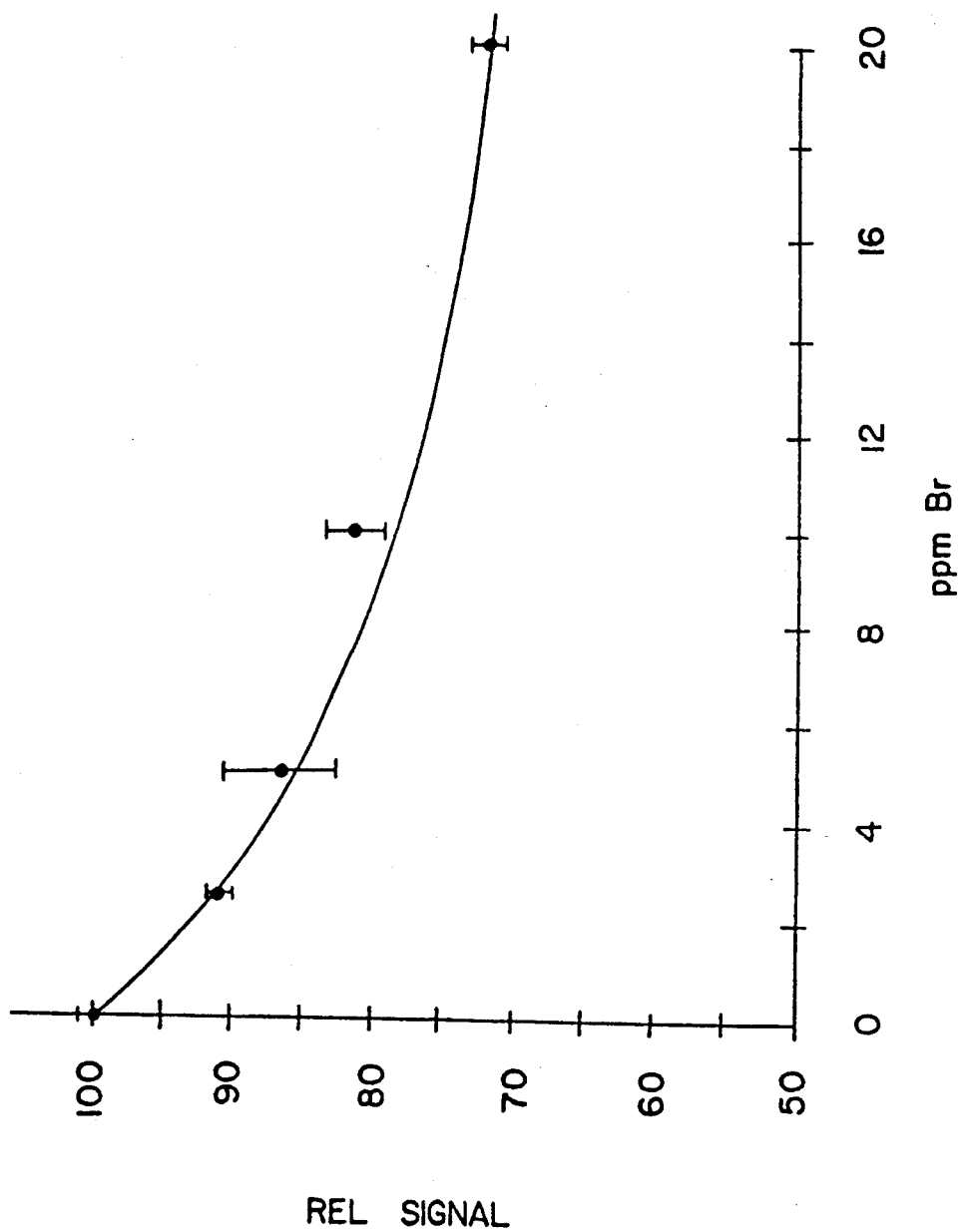

FIG. 41 graphically illustrates the HCl flame infrared emission signal versus bromide concentration.

Figure 42:
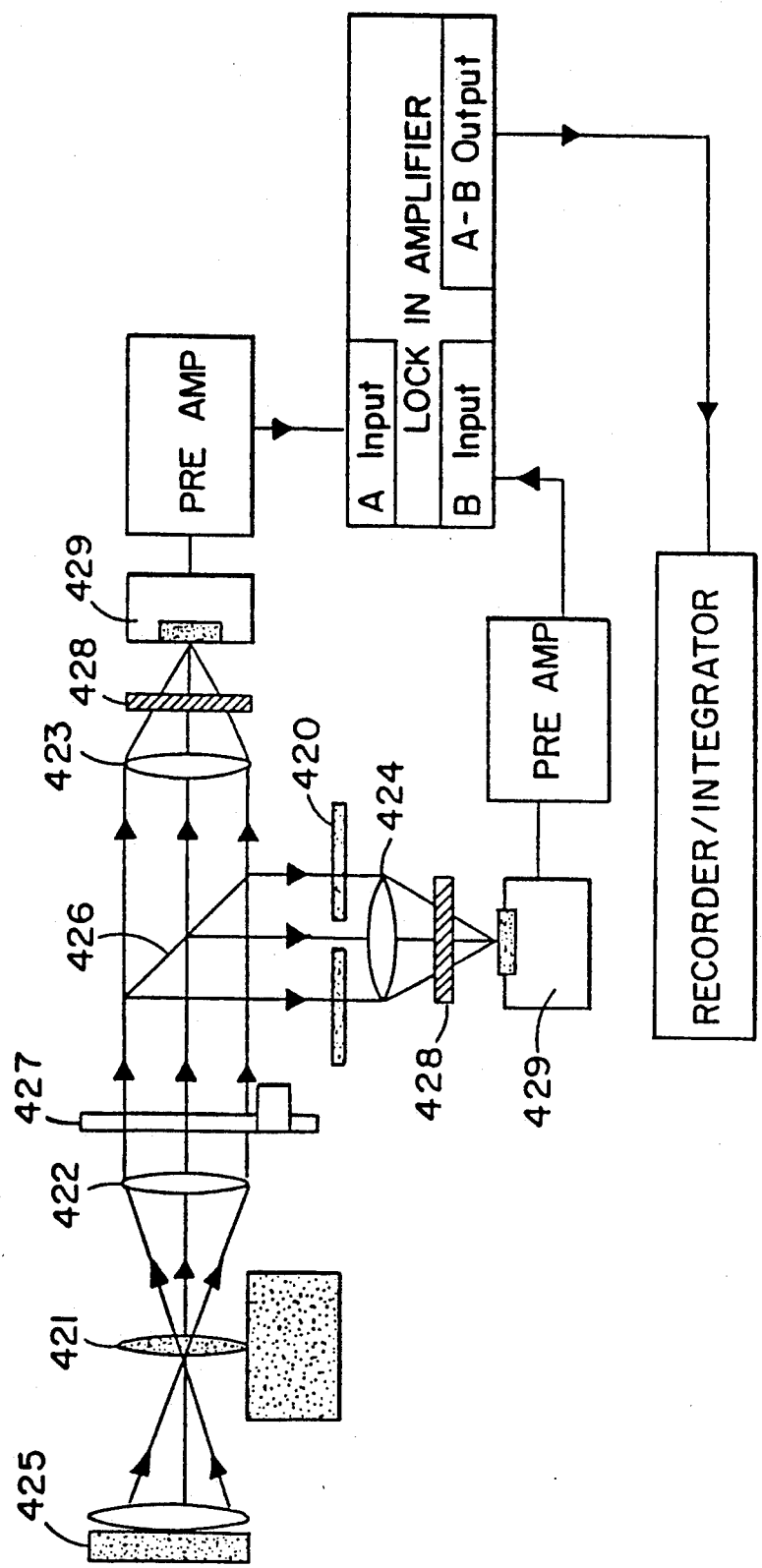

FIG. 42 schematically illustrates the dual channel system of Experiment 5.

Figure 43:
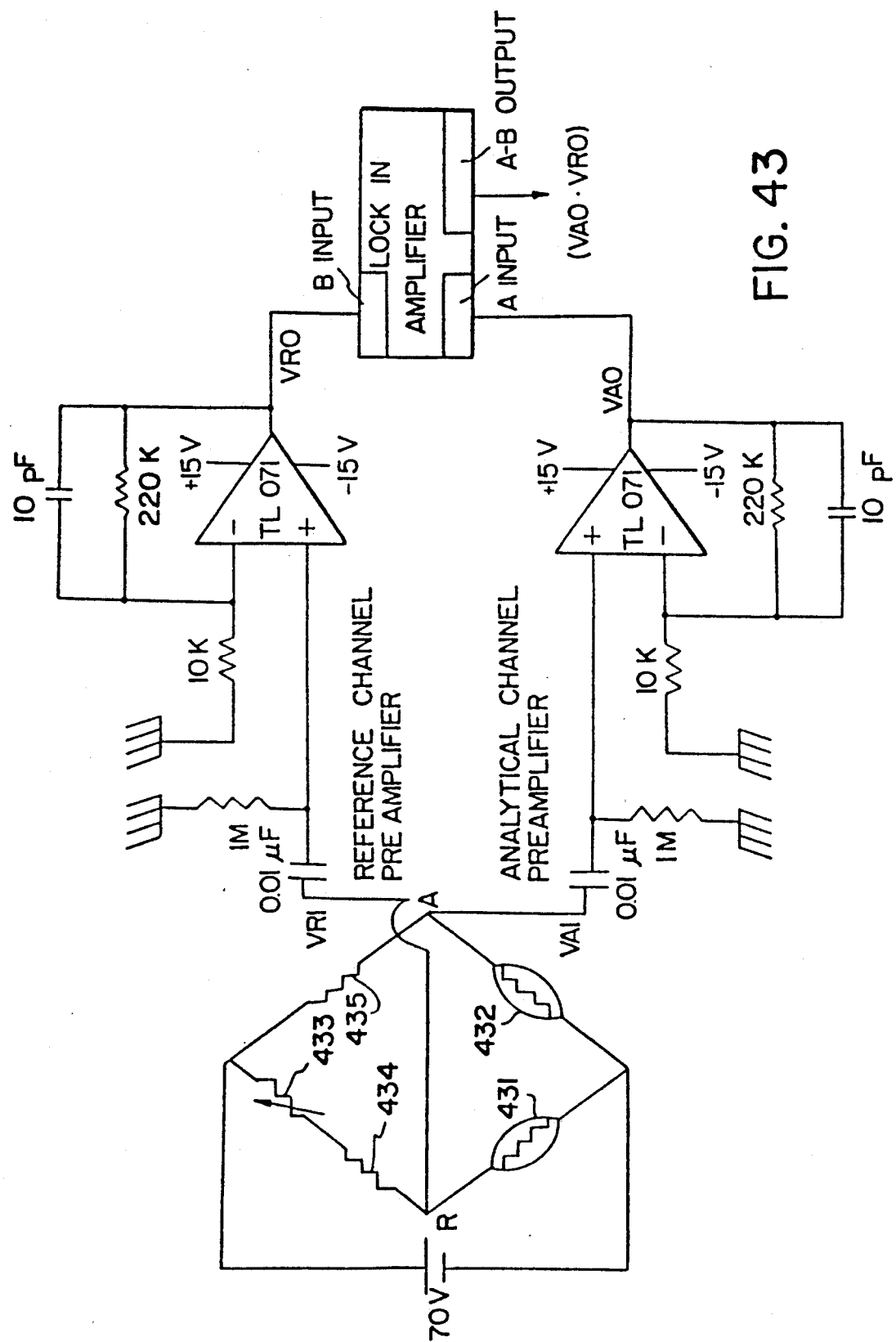

FIG. 43 schematically illustrates the electronic signal processing module of the dual channel system with optical attenuation.

Figure 44:
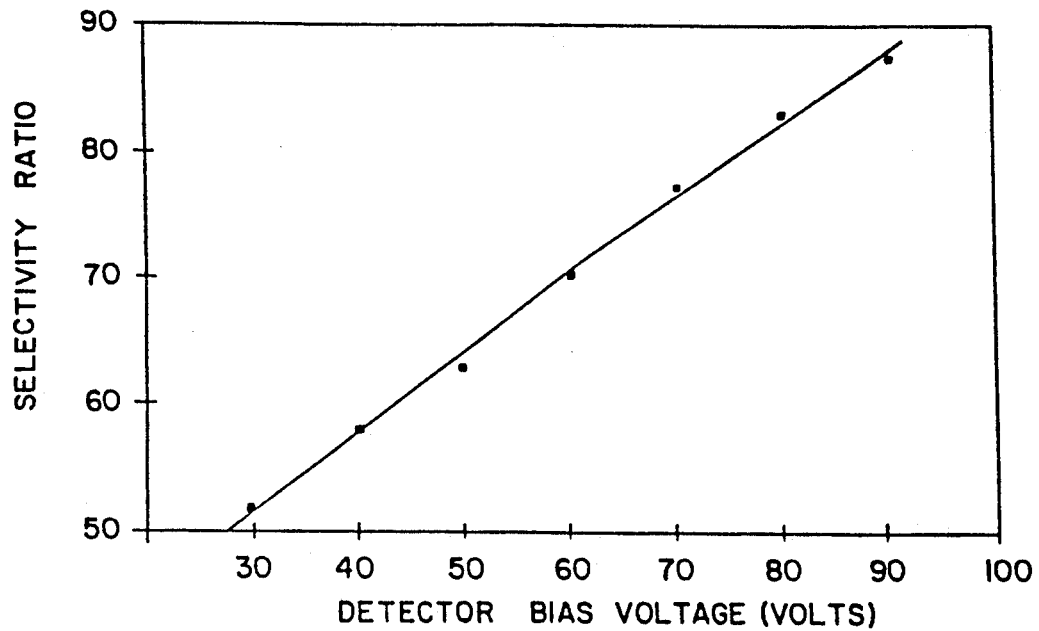
Figure 44:
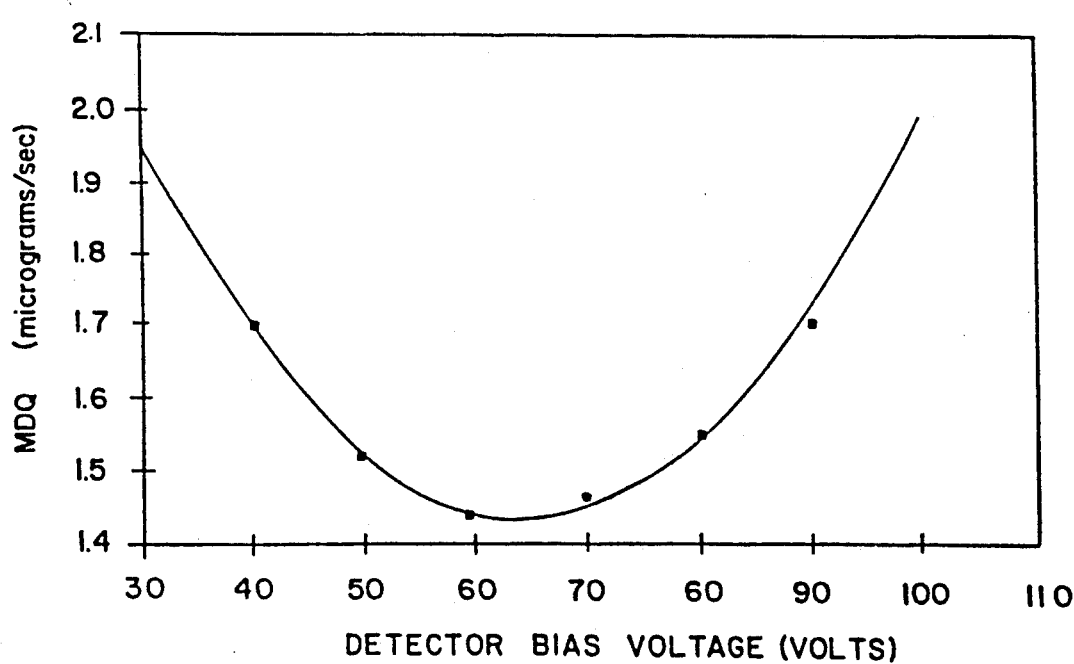

FIGS. 44A and 44B graphically illustrates (A) the selectivity ratio versus detector bias voltage and (B) the detection limit concentration versus detector bias voltage for the dual channel system.

Figure 45:
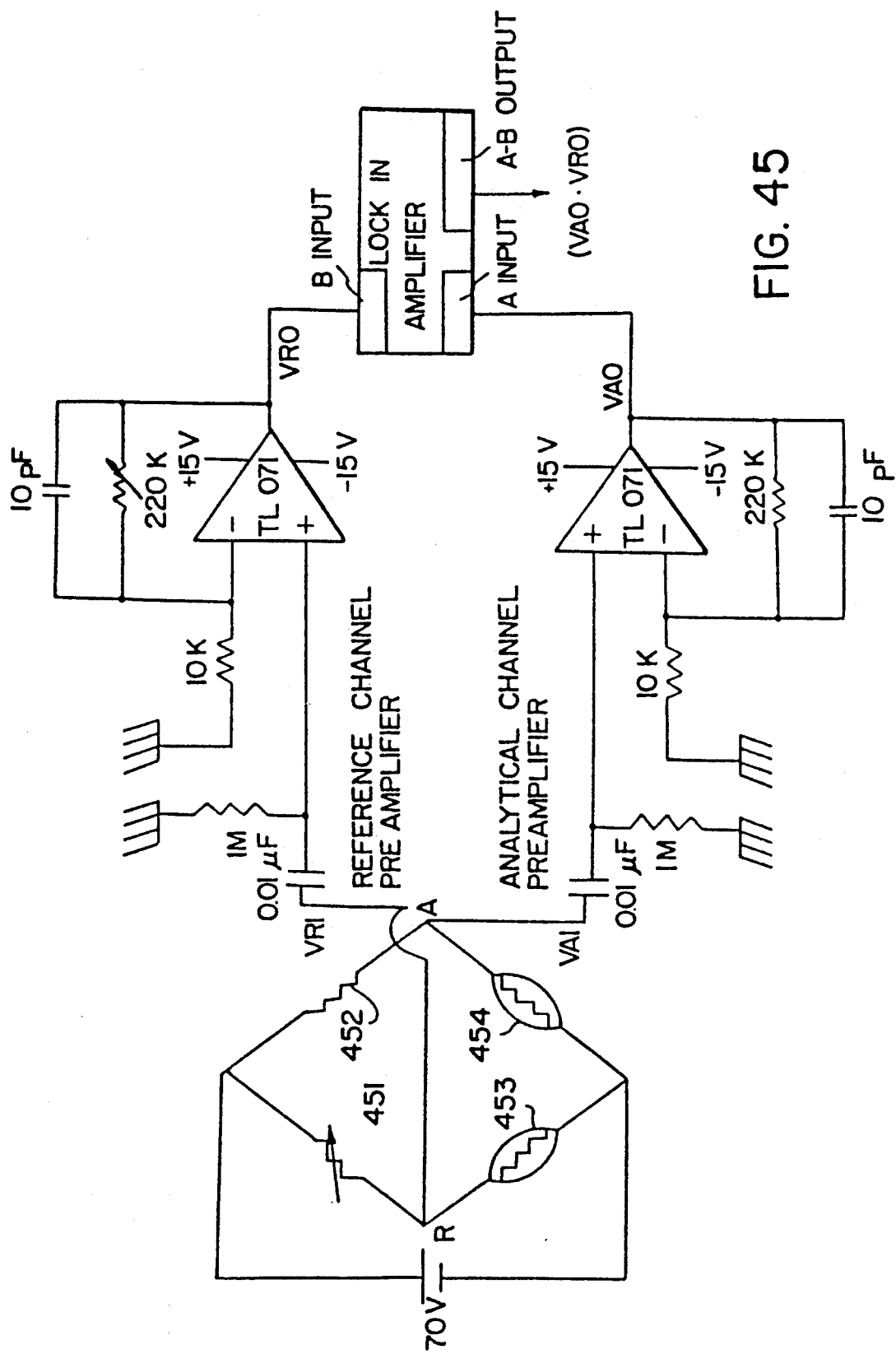

FIG. 45 schematically illustrates the electronic signal process module of the dual channel system with an adjustable load resistor.

Figure 46:
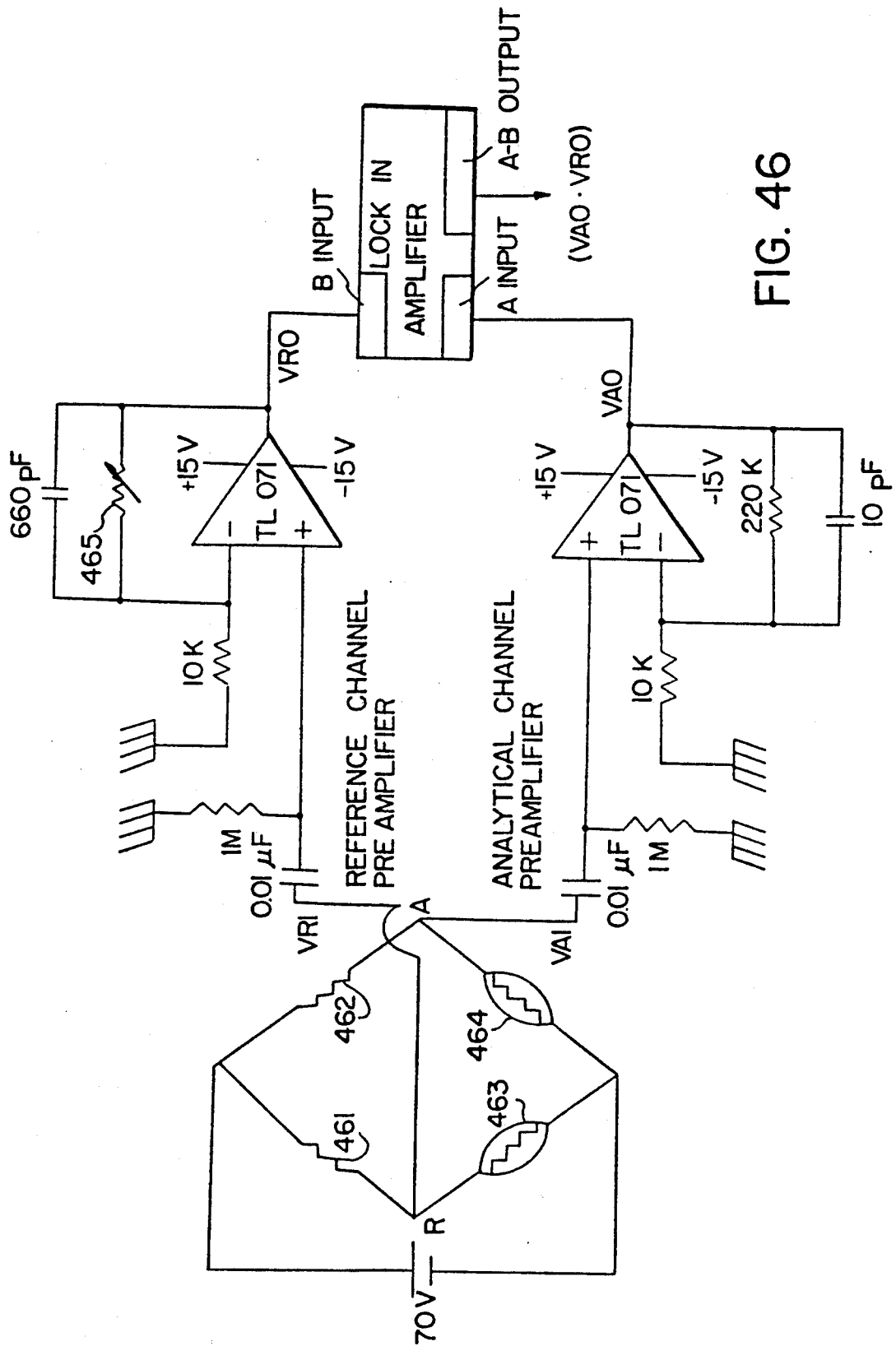

FIG. 46 schematically illustrates the electronic processing module of the dual channel system with an adjustable preamplifier gain.

Figure 47C:
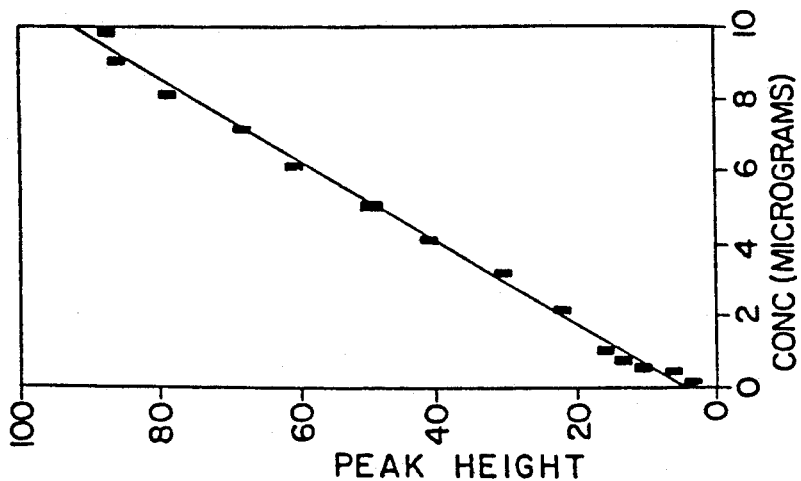
Figure 47B:
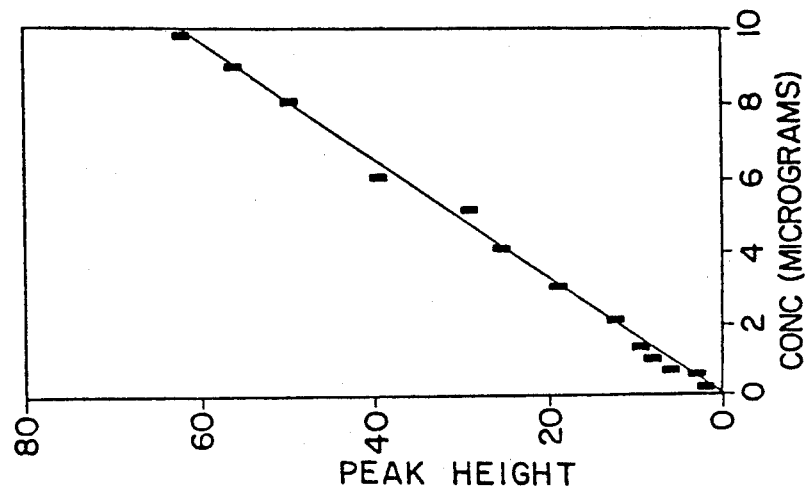
Figure 47A:
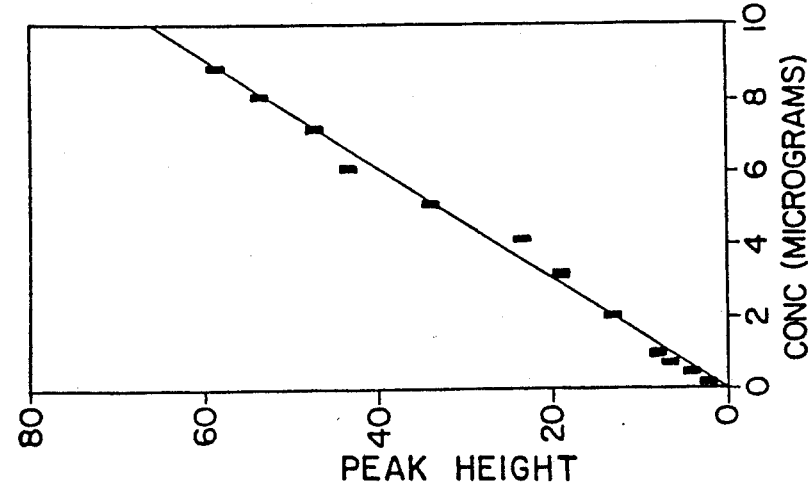

FIGS. 47A to 47C graphically illustrate peak height versus concentration for the dual channel system in the fluoride sensitive, chloride sensitive and carbon sensitive modes.

FIGS. 48A to 48C are flame infrared emission chromatograms illustrating the relative performance of the subtracted and unsubtracted modes of operation in three selective modes.

Figure 49:
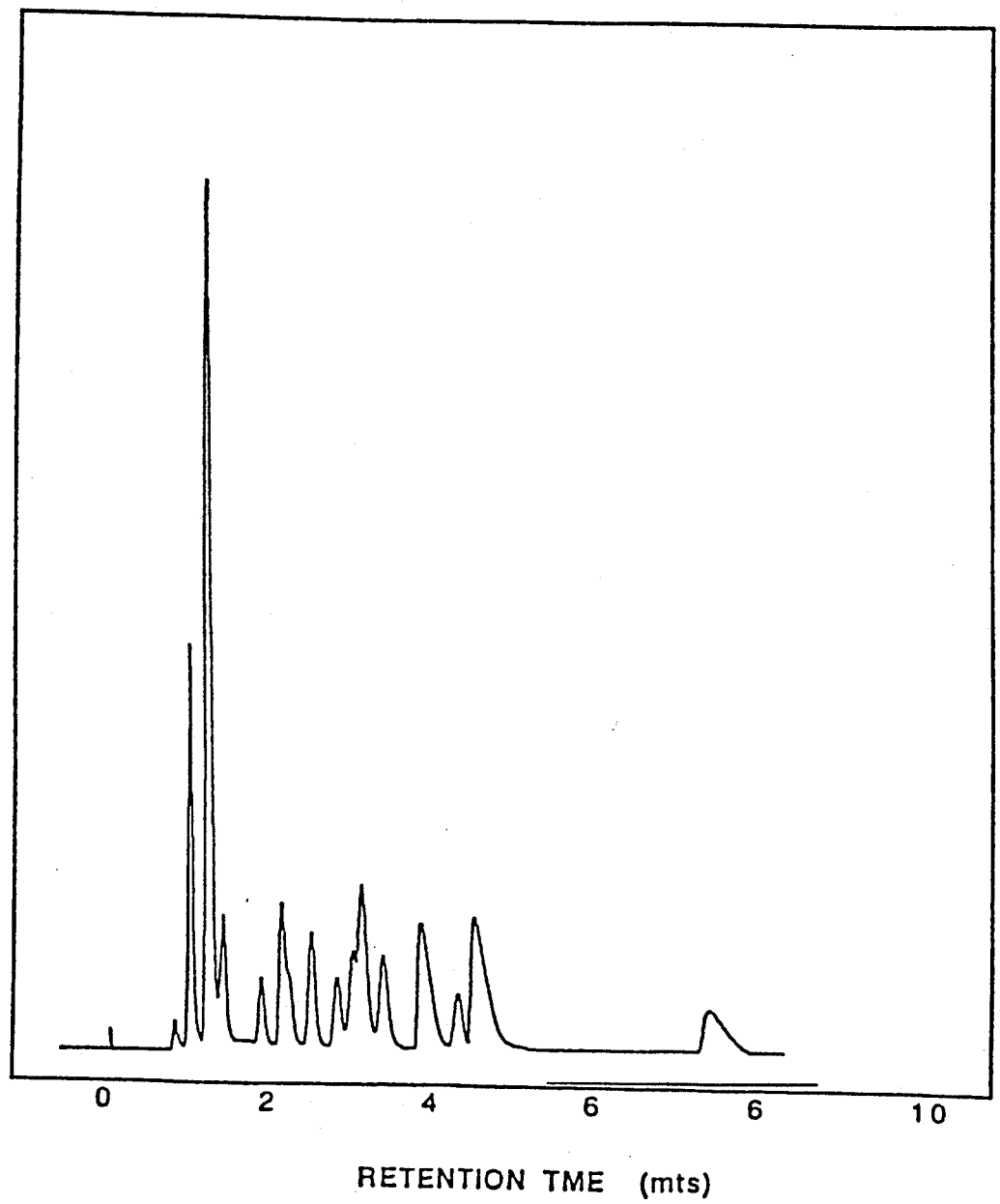

FIG. 49 is a chromatograph of a complex mixture utilizing a commercial TCD detector.

Figure 50:
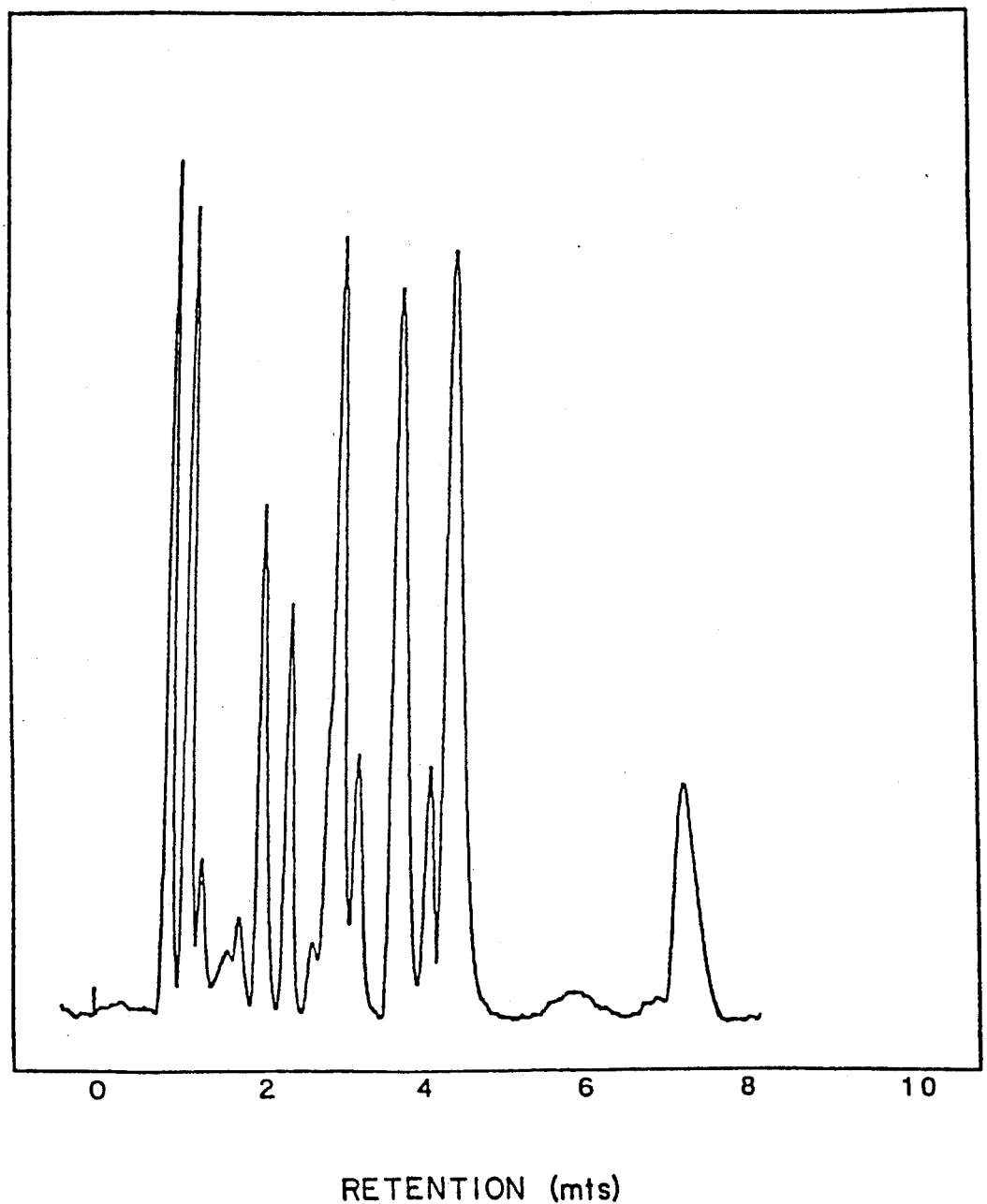

FIG. 50 is a chromatograph of a complex mixture utilizing a flame infrared emission detector in the carbon mode.

Figure 51:
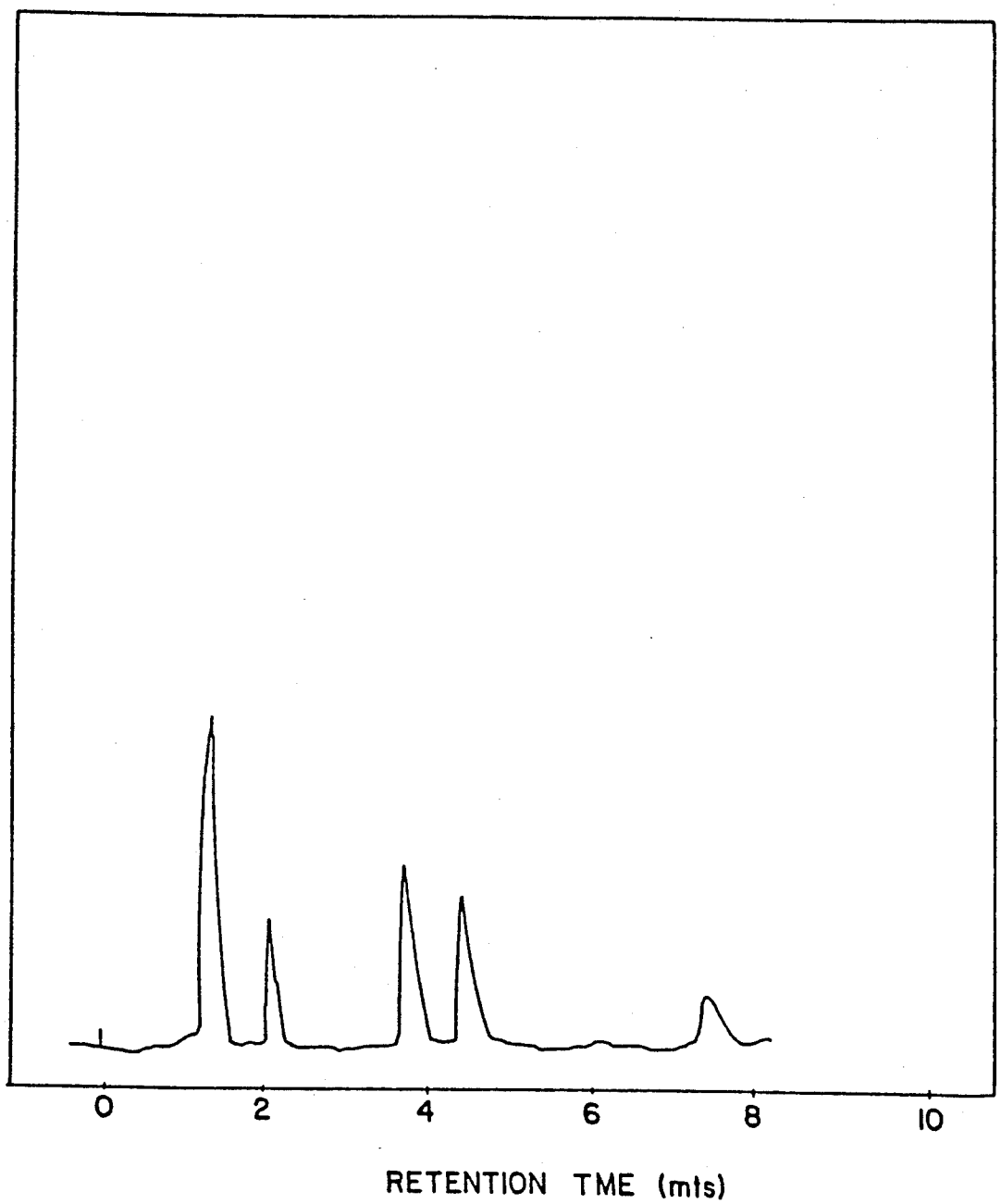

FIG. 51 is a chromatograph of a complex mixture utilizing a flame infrared emission detector in the fluoride selective mode.

Figure 52:
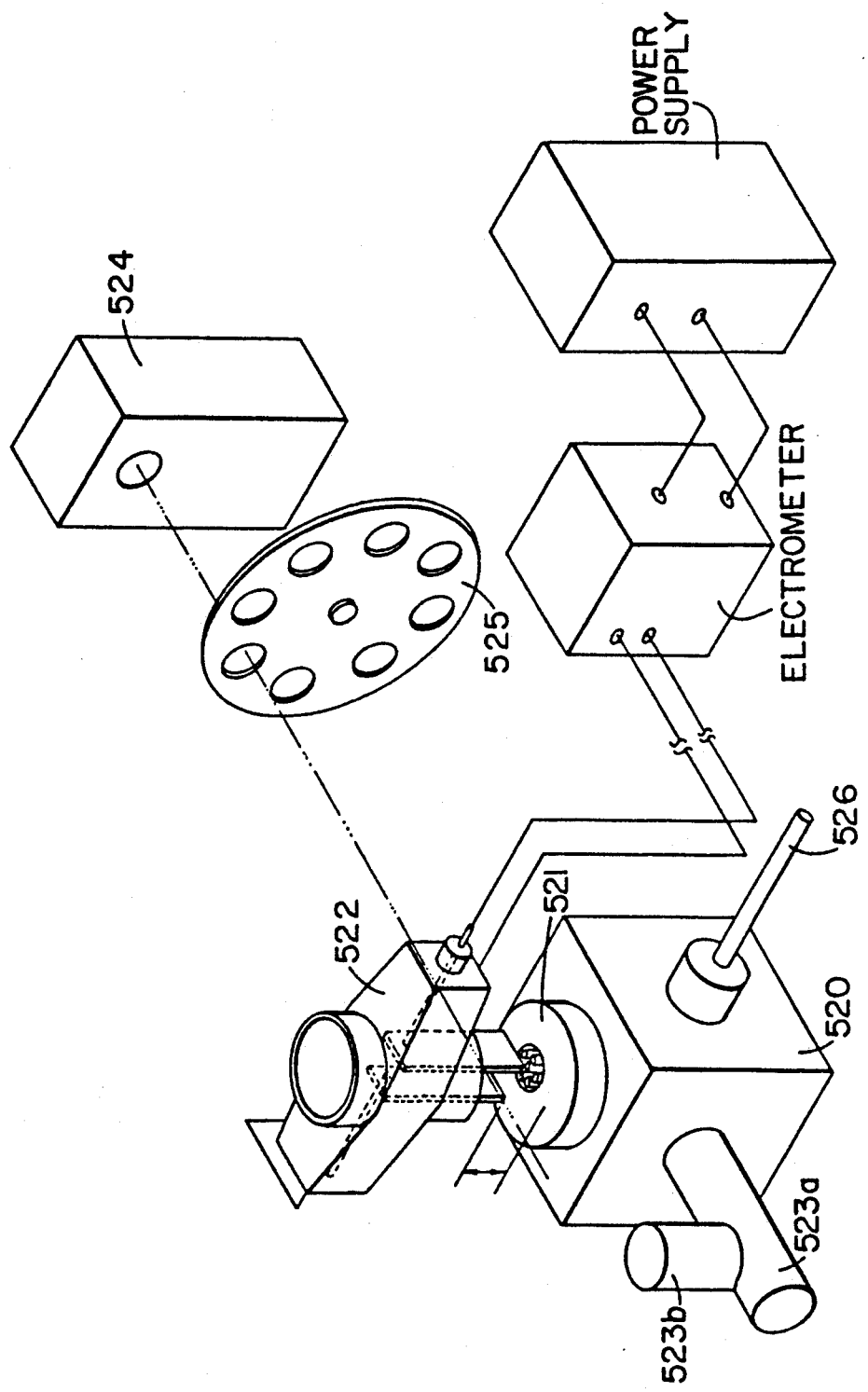

FIG. 52 schematically illustrates the apparatus for a combined infrared and flame ionization detector.

SUMMARY OF THE INVENTION

The present invention relates to infrared emission detection means and method whereby the infrared emission of excited molecules of interest in a sample is used as a basis for detection of compounds.

In one aspect of the invention, infrared emission is observed as a means of detection for chromatography. Organic compounds introduced into a flame result in the production of carbon dioxide which allows observation of two strong emission bands over the wavelength from 1 to 5 $\mu$m. Other infrared active species could be produced as well over the entire infrared region.

Both total organic carbon (TOC) and total inorganic carbon (TIC) determinations in aqueous samples can be made. Total inorganic carbon and total organic carbon are important analytical parameters in the environmental characterization of water. Total organic carbon determinations are performed routinely as a non-specific measure of the organic content of water in polution monitoring. Inorganic carbon exists in water as bicarbonate and carbonate ions and as dissolved carbon dioxide. The sum of these carbon species is called Total Inorganic Carbon (TIC). TIC can be determined directly by acidification of the sample to convert bicarbonate and carbonate ions into dissolved $CO_2$, purging of the sample with a suitable gas to remove the dissolved $CO_2$, and measurement of the $CO_2$ (usually by infrared absorption). Total inorganic carbon determinations by flame infrared emission detection can be used in place of alkalinity titrations to determine the amount of inorganic carbonate present in a water sample.

Infrared emission detection can be used to monitor carbon impurities in electronic grade gases. Carbon/hydrogen characterization of compounds by infrared emission detection is possible by observing the two strong emission bands, one associated with carbon dioxide and one with both water and carbon dioxide. Molecules or molecular fragments containing heteroatoms can be observed by Fourier transform infrared emission spectroscopy. In that many biochemical reactions result in the release of carbon dioxide as a by-product, infrared emission detection can provide the basis for a variety of clinical and biochemical assays.

The infrared emission detection system finds application in the determination of chloride and available chlorine in aqueous samples. The chlorine analysis method includes means for pretreating the sample to evolve chlorine gas. Samples containing aqueous chloride are pretreated with a strong oxidant such as permanganate ion, peroxide ion or $MnO_2$ thereby forming chlorine gas. Samples containing available chlorine due to dissolved molecular chlorine, hypochlorous acid and/or hypochlorite ion are pretreated with acid thereby rapidly generating molecular chlorine gas. The molecular chlorine gas is then liberated from the sample and reacted with hydrogen to form HCl which is excited to emit a characteristic infrared radiation pattern which is detected. In a preferred embodiment, the infrared emission detector is a flame infrared emission detector wherein the flame is a hydrogen/entrained-air flame. In this preferred embodiment, the chlorine gas reacts with hydrogen from the flame to form HCl. The HCl is excited by the flame and exhibits a strong, well-resolved emission band which lies between those for water and carbon dioxide. A 3.8 $\mu$m bandpass filter in the infrared emission detector is used to monitor the emission band and subsequently determine the concentration of chloride and available chlorine in the sample.

The performance of the basic infrared emission detector is improved two orders of magnitude by the use of a dual beam system with background subtraction capability. The selectivity ratio and detection limits are optimized by adjusting the detector bias voltage, using an optical filter in the reference channel for background compensation and balancing the Wheatstone bridge network. The improved detector can therefore detect smaller quantities of species of interest. A preferred embodiment is the use of the improved detector for the detection of carbon compounds, chlorinated compounds, fluorinated compounds as well as chlorofluorocarbons.

The flame ionization detector (FID) is probably the most currently used GC detector. It is surely the most sensitive for organic compounds. A combination infrared detector combining an FID and a flame infrared emission detector provides FID sensitivity and flame infrared emission detection of CO, $CO_2$ and other compounds.

DETAILED DESCRIPTION OF THE INVENTION

The present invention relates to an infrared detection means and a method for detecting selected molecules of interest in a gaseous sample or samples which can be converted to the gas phase. The infrared detection means includes a detector means and a means for exciting molecules of interest in the sample to emit a characteristic infrared radiation pattern. In one embodiment, heating by a flame is employed to combust and excite the molecules of interest in the sample to produce vibrationally excited molecules such as carbon dioxide which can emit infrared radiation. A pre-determined wavelength of infrared radiation emitted by the molecules of interest is observed with a detector by generating an electrical signal in response to the emission at the observed wavelength. The observation wavelength is preselected from the characteristic infrared radiation pattern of the molecule of interest. The means for isolating a preselected wavelength of infrared radiation is mounted between the exciting and detector means.

A factor necessary for successful implementation of infrared emission is to achieve a useful level of contrast between the source and the background, that is the source should be at a higher temperature than the surrounding background, and the temperature of the source should be greater than the temperature of the detector. For this reason, one would not expect to see infrared emission from a gas at room temperature if the background and the detector are also at room temperature. Therefore, the first requirement for the successful implementation of this technique is in most cases a means to heat the gas above room temperature. This does not necessarily mean that a flame is required. However, the hotter the gases, the greater the radiant emissivity, and the more sensitive the detection system. Since flames typically have temperatures on the order of 1000–3000 K., they represent potentially good emission sources for this application if a low-background flame in the vicinity of the selected emission band can be found.

It should be stressed, however, that other means could be used to excite the gases so that they would emit infrared bands. Other excitation means include: 1) other thermal excitation such as a furnace excitation; 2) excitation by electron impact in a gas discharge; 3) excitation of carbon dioxide by collisions of the second kind with vibrationally excited nitrogen (similar to the mechanism used in the carbon dioxide laser); and 4) photo-excitation with an appropriate source. Photoexcitation can be accomplished from the 000 level of $CO_2$ (resonance excitation) or from the 010 level which is appreciably populated even at room temperature (non-resonance excitation). Such infrared fluorescence could be conveniently excited with a carbon dioxide laser emitting radiation at 10.6 $\mu$m. Absorption of such radiation would cause the transition from 010 to 001.

A second requirement for high sensitivity is the avoidance of the use of any form of solid containment such as a sample cell. In order to see infrared emission, there must be some contrast between the infrared emitting source (i.e., the gas in this case) and the background as a result of a thermal gradient. When a heated gas is introduced into a solid sample container, however, the gas immediately begins to heat the container and the thermal gradient and the contrast gradually disappear with time as the system reaches thermal equilibrium. As a result of this process, the emission signal, which is initially present from the gas because it is hotter than the walls of the cavity, gradually fades into the background until it disappears. As a result of this phenomenon, previous experiments had to employ complicated recirculating systems so that hot gases and cold gases could be alternately admitted into the sample cell at a rate sufficiently great that the system would not have time to reach thermal equilibrium (i.e., use of thermal cycling).

If no sample containment is used, as with a flame, there is no blackbody radiator to heat up in the vicinity of the emitting gases, and a steady-state emission signal can be observed. This emission signal is present as long as sample is introduced into the flame, and does not decay away with time as would be the case with the previous systems where the background gradually increases. For this reason, thermal cycling is unnecessary with the present system.

Use of a high temperature excitation source is also beneficial in reducing the effects of atmospheric absorption (i.e., telluric absorption when observing $CO_2$ emission) due to carbon dioxide in the atmosphere. As a gas is heated, various upper level vibrational states become populated, and transitions between upper levels occur. Thus, the emission band observed for a hot gas contains components arising from upper level vibrational transitions (say, $v=4$ to $v=3$) and is therefore broadened and shifted somewhat to longer wavelengths as the temperature is increased. By contrast, carbon dioxide at room temperature is present mainly in the lowest vibrational level ($v=0$). Since the emission band is shifted with respect to the absorption band (because the emitters are at a higher temperature than the absorbers), atmospheric absorption by carbon dioxide is not a significant problem.

Finally, when $CO_2$ emission is being observed in a flame, a flame must be chosen which does not itself produce or contain carbon dioxide. This excludes the use of all carbon-containing fuels, and suggests the use of hydrogen-fueled flames. Two possibilities exist—the hydrogen/air flame and the hydrogen/oxygen flame. Of the two, the hydrogen/air flame is more convenient because it has a lower burning velocity which makes it easier to design a burner which will not flash-back (i.e., explode). The hydrogen/oxygen flame may produce a larger signal because of its higher temperature. Although one of the carbon dioxide emission bands is overlapped with two water emission bands in the hydrogen/air flame (producing a composite band at 2.7 $\mu$m), the region at 4.3 $\mu$m where the only other carbon dioxide emission occurs is clear of any other potentially interfering flame background. For these reasons, the hydrogen/air flame was selected as an excitation source for preliminary studies of flame infrared $CO_2$ emission.

Many detectors sensitive in the infrared are also sensitive in the UV/visible, although they are generally not used in this region because they are considerably less sensitive than other available detectors such as the photomultiplier. The photomultiplier is based on the external photoelectric effect whereby a photon absorbed by a suitable photoemissive material is ejected from the material into the surrounding vacuum. To give the electron sufficient energy to escape the surface of the photoemitter, the photon absorbed must possess an energy greater than the sum of the energy bandgap and electron affinity of the photoemitter. Detectors based on photoemission of electrons as a result of the photoelectric effect can be made very sensitive by the use of electron multiplication with a dynode chain. Thus, photomultipliers can be made so sensitive that they are often limited by the fluctuation in the arrival rate of photons rather than fluctuations arising within the detector itself. Unfortunately, the energy requirement for external photoemission is sufficiently large that the use of photomultipliers is confined essentially to the UV/visible region of the spectrum. By reducing the electron affinity of certain photoemitters, photomultipliers that respond to longer wavelengths beyond the visible (out to about 950 nm) have been produced.

Detectors which respond to infrared radiation can be classified into two basic categories: thermal detectors and quantum detectors. Thermal detectors respond to the heating effect of the infrared radiation and include thermocouples, thermistors, and pyroelectric detectors. Quantum detectors make use of the internal photoelectric effect whereby an electron is promoted from the valence band to the conduction band but is not ejected from the material. As a result, these detectors respond out to wavelengths whose energies correspond to the semiconductor bandgap. These detectors include photovoltaic and photoconductive detectors. Neither category of detector discussed above employs any form of internal amplification comparable to the photomultiplier and for this reason, IR detectors are less sensitive than detectors commonly used for the detection of UV/visible radiation. Since the major source of noise with these detectors originates within the detector itself and is not due to fluctuations in the radiation field, these detectors are frequently cooled to reduce detector noise, and spectrometers which employ them are termed detector-noise limited.

Of the various infrared detectors which are available, quantum detectors generally have a higher specific detectivity than thermal detectors, although thermal detectors have the advantage of flat response over a wide wavelength range. For the applications under consideration, a detector which did not require cooling to dry ice or liquid nitrogen temperatures was desired. For the wavelength region under consideration (2-5 $\mu$m), the lead selenide and indium antimonide detectors were two possibilities. Of the two, the indium antimonide had the higher specific detectivity but generally required cooling. For this reason, the PbSe detector was selected as the most appropriate for preliminary studies on the basis of spectral response and cost. Even with the PbSe detector, however, some thermoelectric cooling may be beneficial to shift the maximum response of the detector to longer wavelengths.

To detect the 4.3 $\mu$m emission band from carbon dioxide without interference from other emission bands (such as the one at 2.7 $\mu$m), some form of wavelength descrimination or isolation was needed. Because the radiation throughput of a conventional grating monochromator can be relatively small, these systems have not been completely satisfactory in the infrared region, and for this reason, Fourier-transform methods are often useful. However, for single molecule response a filter is satisfactory, and therefore a bandpass filter which would transmit the desired band was selected. In this way, the desired band was isolated without reducing the radiation throughput to the detector.

In the visible region of the spectrum, the advantage of emission measurements over absorption measurements is well known among spectroscopists. In view of this, it is surprising that no one thought to exploit this advantage in the infrared. The reason, no doubt, lies in the intuitive, but completely erroneous, notion prevalent among chemists that emission is less sensitive than absorption because emission is based on monitoring excited state populations whereas absorption employs ground state populations. Since everyone knows that the ground state is more populated than any excited states, it follows, ergo, that absorption must be more sensitive than emission. The great fallacy in this argument is the fact that it is irrelevant.

In fact, the reason that absorption measurements are less sensitive than the corresponding emission experiment is due to the fact that as the detection limit is approached, the absorbance, which is the logarithm of the ratio of the incident beam intensity to the transmitted beam intensity, approaches zero. This means that the magnitude of the transmitted beam intensity approaches the magnitude of the incident beam intensity. The question of detection then revolves around whether it is possible statistically to tell the difference between these two large numbers. It is well known from statistics, that differences between two large numbers, which are close to one another in magnitude and which fluctuate, are often not significant. In emission, by contrast, the detection limit occurs when the signal cannot be statistically distinguished from the background. Since the background is hopefully small, this situation is equivalent to the difference between two small numbers which is statistically more reliable. In addition, emission measurements are usually linear over a much wider range of concentrations. Thus, use of emission measurements rather than absorption measurements is based on sound analytical reasoning and is not simply an alternative way of accomplishing the same thing.

It is instructive to point out that, if a flame is used to combust and convert the sample into carbon dioxide, the sensitivity with which this carbon dioxide could be monitored by absorption measurements is likely to be poor. Again, the reason is based on an understanding of Kirchoff's law. Ideally, for greatest sensitivity, if the carbon dioxide produced by the flame were to be monitored by absorption measurements, a blackbody emission source hotter than the temperature of the flame gases would be required. Since flame temperatures are often 2300 K., finding a solid blackbody source which is hotter than the flame is unlikely to say the least.

Process gases are those gases used in manufacturing and electronic-grade gases in particular are those gases used in the manufacture of electronic devices. Impurities such as CO, $CO_2$, and trace hydrocarbons in gases used in the manufacture of semiconductor devices must be controlled to assure reliable manufacturing conditions. Concentrations of impurities as low as 0.5 to 1 ppmv in nitrogen and argon have been reported to cause difficulties (Whitlock, W. H. et al., *Microcontamination*, May, 1988). Currently, one method for determination of the above impurities is carried out using a flame-ionization detector (FID) using instruments based on gas chromatography. Because the FID does not respond to either CO or $CO_2$, a catalyst system using nickel as the catalyst must be employed to convert the CO and $CO_2$ to methane. The need for the catalytic methanator and complex valving makes the current technology less than ideal.

By contrast, the infrared emission detector has good sensitivity to CO, $CO_2$, and the light gaseous hydrocarbons. Since the catalytic methanator is not needed, problems with the methanation catalyst and complex valving are not encountered. Furthermore, a continuous-monitoring technique is possible with the infrared emission system. In such a system, three gas streams can be analyzed simultaneously. One stream is fed into a flame directly. This stream measures the total impurity concentration (i.e., CO, $CO_2$, and hydrocarbons) ($S_1$) A second stream passes first through a bed of a CO absorbent prior to entering a second infrared emission detector. This stream measures the sum of the $CO_2$ and hydrocarbons ($S_2$) A third stream passes first through a bed of $CO_2$ absorber (Ascarite) prior to entering a third infrared emission detector. This stream measures the sum of the CO and hydrocarbons ($S_3$) The signals from the three streams relate to the impurity concentrations as follows:

$$S_2 + S_3 - S_1 = \text{hydrocarbons}$$

$$S_1 - S_3 = CO_2$$

$$S_1 - S_2 = CO$$

By measuring combinations of components simultaneously, the infrared emission system has a multiplex advantage over systems which measure one component at a time.

Another major application of infrared emission technology is for water analysis. This includes drinking water (potable water), environmental samples, wastewater, and even clay-based drilling muds used in petroleum production (i.e., oil rigs). This application falls into two major categories: total inorganic carbon- and organic carbon determinations.

The presence of carbonates in water and other fluids often has a deleterious effect on the use of these liquids. For example, the presence of dissolved carbonates along with dissolved calcium can lead to scale formation in both domestic and industrial plumbing systems. Scale formation in plumbing systems not only impedes fluid flow but reduces the heat transfer efficiency of the fluid when used for cooling purposes. In petroleum production, the presence of carbonates adversely affects the performance of deflocculated clay-based drilling muds (Garrett, R. L., *J. Pet. Tech.*, June, 1978; p. 860.)

In current water technology practice, the carbonate concentration is determined indirectly by means of alkalinity titrations. The alkalinity of a water sample is determined from the proton condition of the solution as $$C_B - C_A = [\text{Alk}] = [HCO_3^-] + 2[CO_3^{2-}] + [OH^-] - [H^+]$$

$$[\text{Alk}] = \alpha_1 C_T + 2\alpha_2 C_T + [OH^-] - [H^+]$$

where
$C_A$ = concentration of strong acid
$C_B$ = concentration of strong base
$C_T = [H_2CO_3] + [HCO_3^-] + [CO_3^{2-}]$
$D = ([H^+]^2 + K_1[H^+] + K_1K_2)$
$\alpha_1 = K_1[H^+]/D$
$\alpha_2 = K_1K_2/D$
and $K_1$ and $K_2$ are the first and second dissociation constants of carbonic acid. The alkalinity of a water sample is also a measure of the acid neutralizing capacity of the solution.

By titrating a water sample with strong acid ($H_2SO_4$) to a methyl orange endpoint, the total alkalinity of a water sample is determined. The total inorganic carbon or $C_T$ is determined from a knowledge of the alkalinity by rearranging the alkalinity relationship:

$$C_T = ([\text{Alk}] - [OH^-] + [H^+])/(\alpha_1 + 2\alpha_2)$$

$$C_T \sim [\text{Alk}]/(\alpha_1 + 2\alpha_2)$$

Thus as long as there are no other alkaline materials in the water besides carbonate the alkalinity and the pH of the solution are all that is needed to determine $C_T$. In certain determinations, however, such as drilling muds, there are appreciable amounts of other alkaline materials present which make alkalinity titration data unreliable as a means of determining $C_T$. Even in the absence of other interferences, the alkalinity titration is difficult to perform because the indicator endpoint is not sharp. Even when potentiometric titrations are performed, the endpoint is still not sharp because the sample is being titrated back to carbonic acid.

By contrast, the infrared emission TIC determination is simple, convenient and direct. By direct, it is meant that the infrared emission measures $C_T$ directly rather than a property which is related to $C_T$ (i.e., the acid neutralizing capacity). The use of a direct measurement technique leads to more reliable data on the actual parameter of interest. The direct measurement does not require a knowledge of the dissociation constants for carbonic acid to calculate the desired parameter from the measured quantity.

In the infrared emission procedure, sulfuric acid (0.5 mL) is introduced into a fritted sparging tube where it is subsequently degased. A water sample (1 mL) is added to release carbon dioxide gas which is flushed with helium into a hydrogen/air flame. The infrared emission from carbon dioxide is measured with an infrared emission detector as described previously. A calibration curve prepared from standard carbonate solutions is used to determine the total inorganic carbon concentration in the sample.

Infrared emission detection is also useful in determining the carbon dioxide content in carbonated beverages such as soft drinks and beer.

Organic materials in water samples may arise from naturally occurring compounds produced by living organisms or from anthropogenic sources. The sum of the naturally occurring organic materials and the synthetic organic materials is referred to as the total organic carbon in the water sample. Thus, the total organic carbon content of a sample is a non-specific (i.e., doesn't determine the actual individual compounds present) measure of the organic content of the sample. Total organic carbon (TOC) determinations are performed on a wide range of samples, including ground water, drinking water, semiconductor process water, municipal wastewater, and industrial wastewater (Small, R. A. et al., *International Laboratory*, May, 1986). Industrial applications of TOC determinations include determination of organic contamination in mineral products such as acids, caustic solutions, as well as aluminum-, nickel-, and cobalt chlorides. Power generation plants use TOC measurements to determine organic contaminants in cooling water and steam-generation water. Even small amounts of formic- and acetic acid can cause corrosion of turbine blades and heat exchanger equipment (Bernard, B. B., "A Summary of TOC Developments", O. I. Corporation College Station, Texas, 1985). Since an increase in the organic content of water can be an indication of pollution, TOC determinations have been used to monitor surface water, ground water (i.e., wells), and other water sources for wastewater contamination and industrial effluents.

Currently, TOC determinations are performed by first oxidizing the organic material to carbon dioxide by a variety of methods (Small, R. A. et al., *International Laboratory* May, 1986). The carbon dioxide gas generated by this oxidation is then determined by non-dispersive infrared (NDIR) absorption spectrophotometry. Although a variety of NDIR procedures have been employed, a primary problem with absorption measurements is the concomitant absorption by water vapor and acid gases. Partial elimination of the water vapor interference has been achieved through humidity control of the reaction gases flushed into the infrared absorption cell. Because measurements are made in absorption, all TOC analyzers require an infrared emission source to produce the infrared radiation.

With the infrared emission system, carbon dioxide is produced by the same methods currently used to oxidize organic materials to $CO_2$. These oxidation methods include one or a combination of the following: chemical methods such as the use of peroxydisulfate, heating such as in a furnace with copper oxide and the use of UV radiation. After oxidation, the $CO_2$ is flushed out of the sample to the infrared emission detector.

Alternatively, for some compounds if the infrared emission detector uses a flame for exciting the molecules of interest in the sample, the sample may be combusted directly in the flame to generate $CO_2$. By utilizing infrared emission instead of absorption of $CO_2$ the interference by other concomitants produced by the oxidation process is avoided. Since the infrared emission detector is not affected by water vapor and acid gases, these interferences are absent with the infrared emission TOC analyzer. Since the infrared emission system employs a filter, it falls in the category of non-dispersive infrared analysis (only in emission rather than absorption).

Since two strong emission bands are observed in the flame, one corresponding to the asymmetric stretching vibration of carbon dioxide and the other to water and carbon dioxide combination bands, carbon/hydrogen characterization of compounds is possible by using both bands. In the combustion of any organic material, carbon dioxide, water vapor, and other combustion products are produced. The presence of carbon dioxide and water alters the intensities of the water band at 2.0–3.5 $\mu$m in addition to the carbon dioxide band at 4.25–4.8 $\mu$m. Thus, a chromatography infrared emission detector monitoring both of these bands provides additional information about the compound beyond that available with an FID or thermal conductivity detector. Although this system may not be able to determine the carbon/hydrogen ratio with the same precision as conventional combustion analysis, it distinguishes different alkanes, alkenes, aromatics, et cetera. A carbon to hydrogen ratio instrument is useful for combustion monitoring, as in smoke stack and rocket engine firing monitoring.

The infrared emission is useful as a detector in conventional carbon/hydrogen analyses (as opposed to using it as a detector in chromatography). As with the TOC analyses, the infrared emission system is used as the detection means in the analysis. Thus, an instrumental carbon/hydrogen analyzer can use conventional combustion tube techniques to transform the organic material into water and carbon dioxide. The infrared emission is then used to detect the amounts of these materials which have been generated.

Various other emission bands are emitted when organic compounds containing heteroatoms are introduced into the hydrogen/air flame. Fluorine and chlorine containing compounds produce characteristic emission spectra of HCl and HF. Silicon and sulfur containing compounds produce emission characteristic of Si-0 vibrations and $SO_2$ vibrations. Freon 113 produces a very interesting emission spectrum with HF, HCl, $CO_2$, $H_2O$, and a number of bands attributed to other vibrations.

The element chlorine is widely distributed in nature and is used extensively in its various oxidation states. Aqueous elemental chlorine ($Cl_2$) and hypochlorite ($OCl^-$), for example, are employed as bleaching agents and as disinfectants to prevent the spread of waterborne diseases. Because of the reactivity of the higher oxidation states of chlorine, the element occurs in nature primarily as the chloride ion ($Cl^-$) and is one of the major inorganic constituents of surface waters, groundwaters, and wastewaters. In seawaters, chloride levels, expressed as chlorinity, are approximately related to salinity and can be used to determine the concentrations of all other bio-unlimited elements present in a sample. Chloride concentration is also used as an indicator of water condition. For example, elevated chloride concentrations in the sewerage of coastal areas may signal seawater intrusion into the system, while in potable water they are often associated with wastewater contamination. In process waters, chloride concentrations are monitored regularly since elevated levels are generally associated with increased deterioration of metallic pipes and structures, while in cooling water, they are used to indicate the cycles of concentration.

Because of the widespread use and occurrence of the many forms of chlorine, analytical methods for their determination are of great importance. A large number of methods exist for the determination of chloride ion and chlorine in aqueous samples. These include chromatographic, spectrometric, potentiometric and titrimetric procedures, with the most widely used methods involving titration of the sample.

For the titrimetric determination of aqueous chloride, various argentometric methods exist which use either indicators or potentiometers to detect the endpoint. Alternatively, mercuric nitrate can be used to titrate chloride ion using diphenylcarbazone as an indicator.

For the determination of chlorine in bleach bath liquors and natural and treated waters in concentrations greater than 1 mg/L, iodometric titration is the method of choice. For chlorine levels less than this amount, amperometric titrations are preferred, but require greater operator skill to avoid loss of chlorine through mechanical stirring. Poor endpoints are also a problem unless the electrodes are properly cleaned and conditioned. Alternatively, N,N-diethyl-p-phenylenediamine (DPD) can be used to determine dissolved chlorine colorimetrically or titrimetrically using ferrous ammonium sulfate.

All of these titrimetric methods suffer severe interference by a variety of species including, bromide, iodide, cyanide, sulfide, and orthophosphate (for chloride) and other oxidizing agents (for chlorine). Because of the problems associated with existing procedures, new analytical methods for the determination of chloride ion and chlorine in aqueous samples could be of great importance in a number of disciplines.

In that the combustion of chlorine-containing compounds in the flame produces HCl, infrared emission detection under high resolution conditions provides spectra wherein the P and R branches of the HCl infrared emission can be easily detected above the flame background in the region from 3200–2400 $cm^{-1}$. Since the HCl emission band lies between the water emission band at 3800–3200 $cm^{-1}$ and the carbon dioxide emission band centered at approximately 2262 $cm^{-1}$, the strong, well-resolved infrared emission from HCl should also be useful analytically for the determination of Cl in a variety of chlorine-containing samples.

Since chlorine gas reacts rapidly with hydrogen under flame conditions to form HCl $$H_2 + Cl_2 = 2HCl$$

any reaction that generates elemental chlorine in a quantitative manner could serve as the basis of an analytical procedure employing flame infrared emission as a highly specific means of detection. As one example, samples containing dissolved chloride ion could be oxidized to elemental chlorine according to the following half-cell ($E° = -1.36$ V), $$2Cl^- = Cl_2 (aq) + 2e^-$$

using such strong oxidants as permanganate ion ($E° = +1.51$ V in acid solution), peroxide ion ($E° = +1.77$ V in acid solution) or peroxydisulfate ion ($E° = +2.01$ V). The resulting chlorine gas could then be purged from solution using an inert gas and introduced into a hydrogen-air flame to form excited HCl which could be detected by means of its infrared emission.

A second example of an analysis that could be carried out in this manner is the determination of available chlorine in bleaches prepared from elemental chlorine and hypochlorite. In solution these species produce hypochlorous acid ($pK_a = 7.60$ at 25° C.) according to the following two equations, respectively, $$Cl_2 + 2H_2O = HOCl + H_3O^+ + Cl^-$$

$$OCl^- + H_2O = HOCl + OH^-$$

and the term available chlorine refers to the total oxidizing power of the solution due to chlorine, hypochlorous acid and hypochlorite ion, expressed in terms of an equivalent quantity of $Cl_2$. (The distribution of Cl between these three species is temperature and pH dependent). Since the following equation $$Cl_2 + 2H_2O = HOCl + H_3O^+ + Cl^-$$

is readily reversible ($K_{eq}^{-1} = 2.2 \times 10^3$ at 24° C.), addition of acids leads to the rapid generation of dissolved molecular chlorine which can be purged from solution, converted to HCl in the flame, and detected by infrared emission as described previously.

This application reports the development of a new chlorine-specific method for the direct determination of chloride and available chlorine in aqueous samples based on the principle of infrared emission. The flame infrared emission-chlorine analyzer described in Experiment 4 consists of two commercially available purge devices coupled to a flame infrared emission detector. Aqueous chlorine-containing samples are treated chemically to convert the chloride or hypochlorous acid present into molecular chlorine ($Cl_2$) which is then liberated from the sample cell using an inert carrier gas and introduced into a hydrogen/entrained-air flame to produce vibrationally excited HCl.

A substantial improvement in detection capabilities results when a dual beam system is used as the detector of a flame infrared emission detection method. The dual beam system allows subtraction of the background and most importantly the fluctuations in the background (i.e. the noise). The signal is improved by two orders of magnitude with the use of the improved dual beam system. The selectivity ratio and detection limits can be optimized by varying the detector bias voltage, by use of a 3.0 μm filter for background compensation, an optical attenuation method to balance the bridge network, and a variable bridge resistor.

Many biochemical reactions release carbon dioxide as a by-product of the reaction (for example, fermentation of sugar by yeast). Infrared emission is therefore useful for a variety of clinical and biochemical assays involving carbon dioxide, such as the clinical determination of carbon dioxide in blood.

The following experimental embodiments are illustrative.

EXPERIMENT 1

Figure 1:
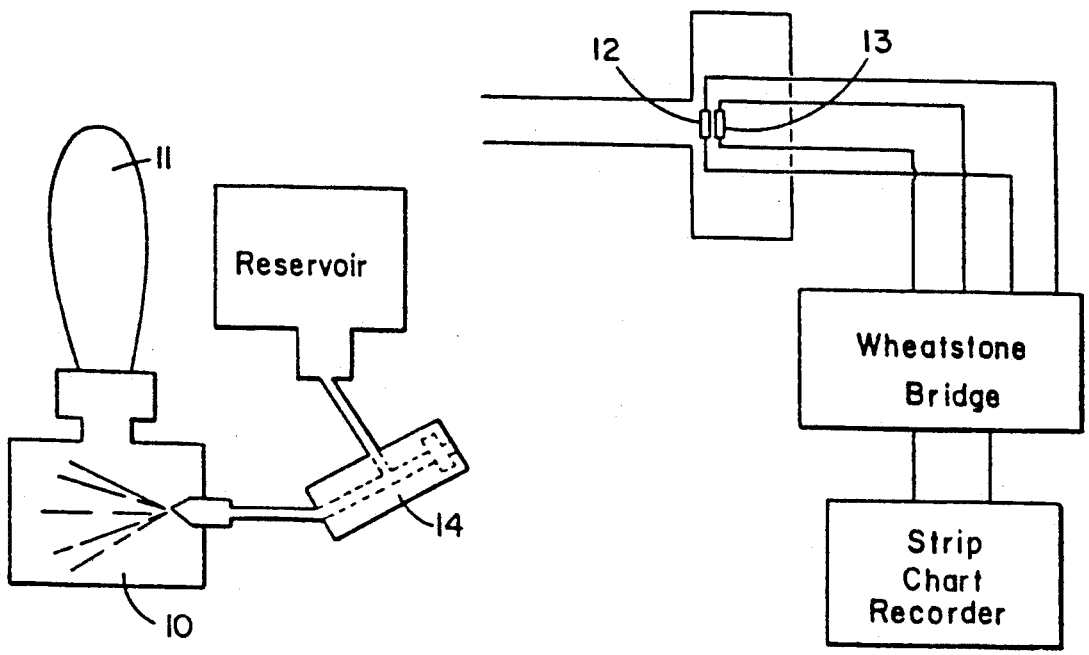
FIG. 1 schematically illustrates the apparatus used in Experiment 1 for the non-dispersive studies.

FIG. 1 shows the experimental arrangement used for the initial non-dispersive studies using thermistor detection. A Varian Techtron burner assembly 10 was used as a nebulizer and to provide the sample introduction system. A Meker burner head producing a flame 11 with a diameter of 1.5 cm was designed and fitted to the burner assembly. Initial studies of the infrared emission from a hydrogen/air flame 11 were made using various thermoflake thermistors 12 (Thermometrics Inc., Edison, N.J.) mounted in a detector head/housing unit on a test setup facing the burner. For these non-dispersive studies, a metal tube was attached to the detector housing to limit the field of view of the thermistor flake. The thermistors 12 and 13 were incorporated into a Wheatstone bridge circuit and a Model 3120TX Bascom Turner digital data aquisition unit (Bascom Turner Instruments, Norwood, Mass.) was employed to record the output. Sample introduction was accomplished by means of a teflon injection device 14 consisting of a T-coupler with one passage capped to accept a septum. The teflon injector unit 14 described above was employed with this test setup to study the direct injection of organic compounds into the flame 11 and to simulate sample introduction from the chromatograph. Using this arrangement, samples up to 50 μL could be injected by means of a Hamilton microsyringe.

Figure 2:
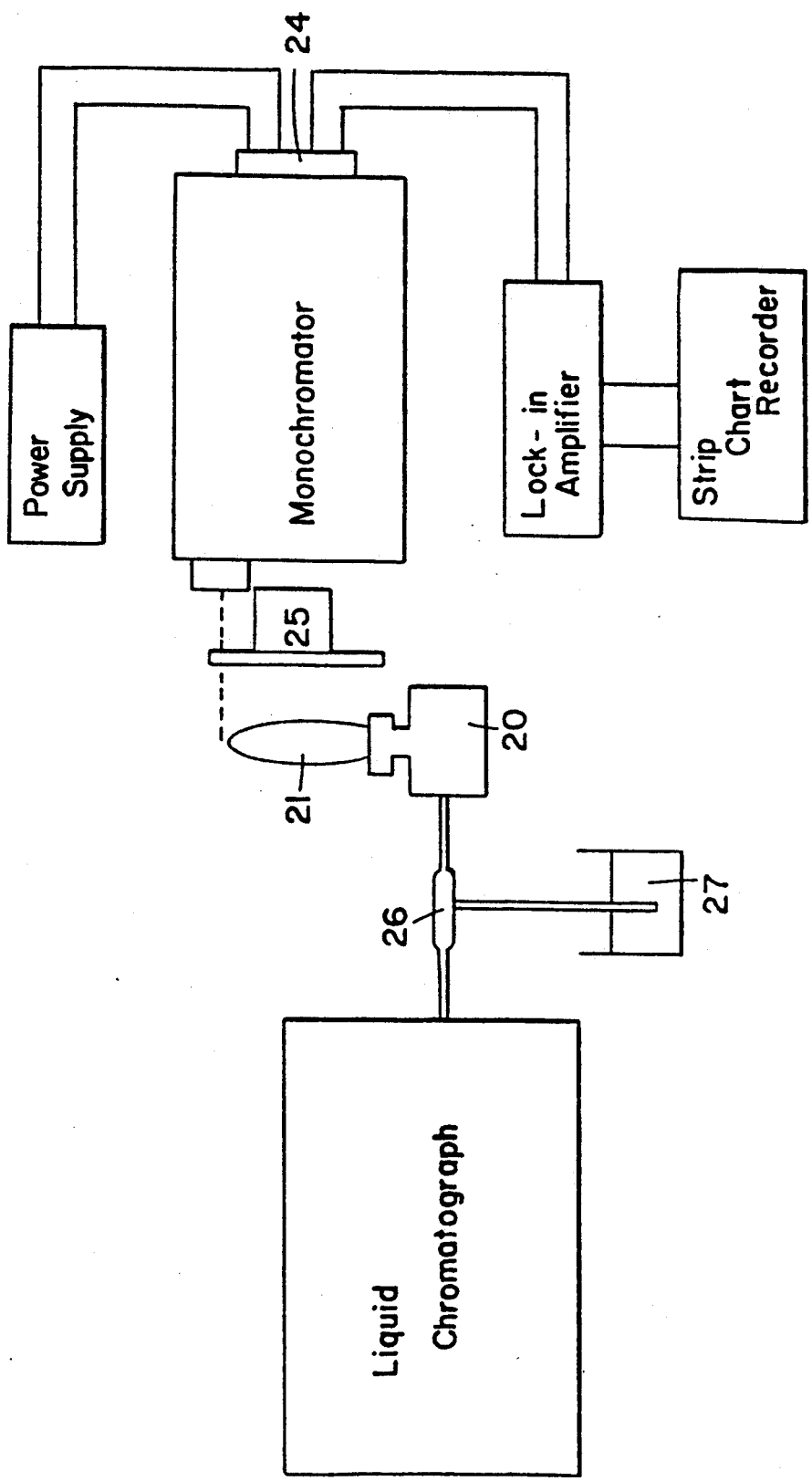
FIG. 2 schematically illustrates the apparatus used in the wavelength-selective studies of Experiment 1.

FIG. 2 shows the experimental arrangement employed for the dispersive wavelength-selective studies using PbSe detector 24. The IR detection system used in this study was assembled using devices and equipment from various manufacturers as listed in Table I.

TABLE I

| Equipment Used | |
| --- | --- |
| Burner | Varian Techtron burner/nebulizer with Meker burner head |
| Dispersion System | Spex Model 1870 0.5-m Czerny-Turner monochromator with 150 groove/mm Bausch and Lomb grating blazed for 4 μm |
| Entrance slit | 3 mm wide, 3 cm high |
| Detector | Hamamsatsu Model PbSe Model P2038-01 |
| Amplifier | Princeton Applied Research Model 128A lock-in amplifier with PAR Model 125A variable speed chopper |
| Readout | Varian Aerograph chart recorder |
| Flow meters | Brooks Instrument Division calibrated flow meters |
| Chromatograph | Varian Model 5000 HPLC with MCH-5 column |

A Spex 0.5-m Czerny-Turner monochromator (Spex Industries, Inc., Metuchen, N.J.) is used as the primary wavelength dispersive device or isolation means. The monochromator is equipped with a 150 groove/mm grating blazed for 4 μm. A 3-mm entrance slit was used. The wavelength scale of the Spex 1870 monochromator was calibrated by the manufacturer for a 1200 groove/mm grating. To determine the wavelength settings with the 150 grove/mm grating, measurements of grating rotation versus counter setting were made. These measurements, combined with the geometric arrangement of the mirrors, enabled the wavelength corresponding to a given counter setting to be calculated by means of the grating equation, $$m\lambda = d[\sin(r-\theta_4) + \sin(r+\theta_2)]$$

where m is the order, is the wavelength, d is the grating constant, and r is the rotation angle of the grating. In this equation, $\theta_2$ is the angle of reflection of the chief ray from the collimating mirror and $\theta_4$ is the angle of incidence of the chief ray on the focusing mirror. For a given optical layout, $\theta_2$ and $\theta_4$ are constants. These calculations were checked by observing the 670.7 nm line from a lithium hollow cathode in the third order and comparing the actual counter setting with the observed counter setting.

A Hamamatsu lead-selenide photoconductive cell 24 with integral thermo-electric cooling (P2038-01, Hamamatsu Corp., San Jose, Calif.) was employed as the infrared detector. Table II lists the specifications of this particular device.

TABLE II

| Performance Characteristics of P2038-01 Hamamatsu PbSe Detector | |
|---|---|
| Sensitive Size: | 1 × 3 mm |
| Peak Responsivity: | 3.8 μm |
| IR Cutoff Wavelength: | 4.85 μm |
| Dark Resistance: | 0.6 Mohm |
| Recommended Load Resistance: | 0.5 Mohm |
| Specific Detectivity (500 K source, 600 Hz chopping frequency, 1 Hz bandwidth): $1.2 \times 10^8$ cm Hz$^{\frac{1}{2}}$ w$^{-1}$ | |

Figure 4:
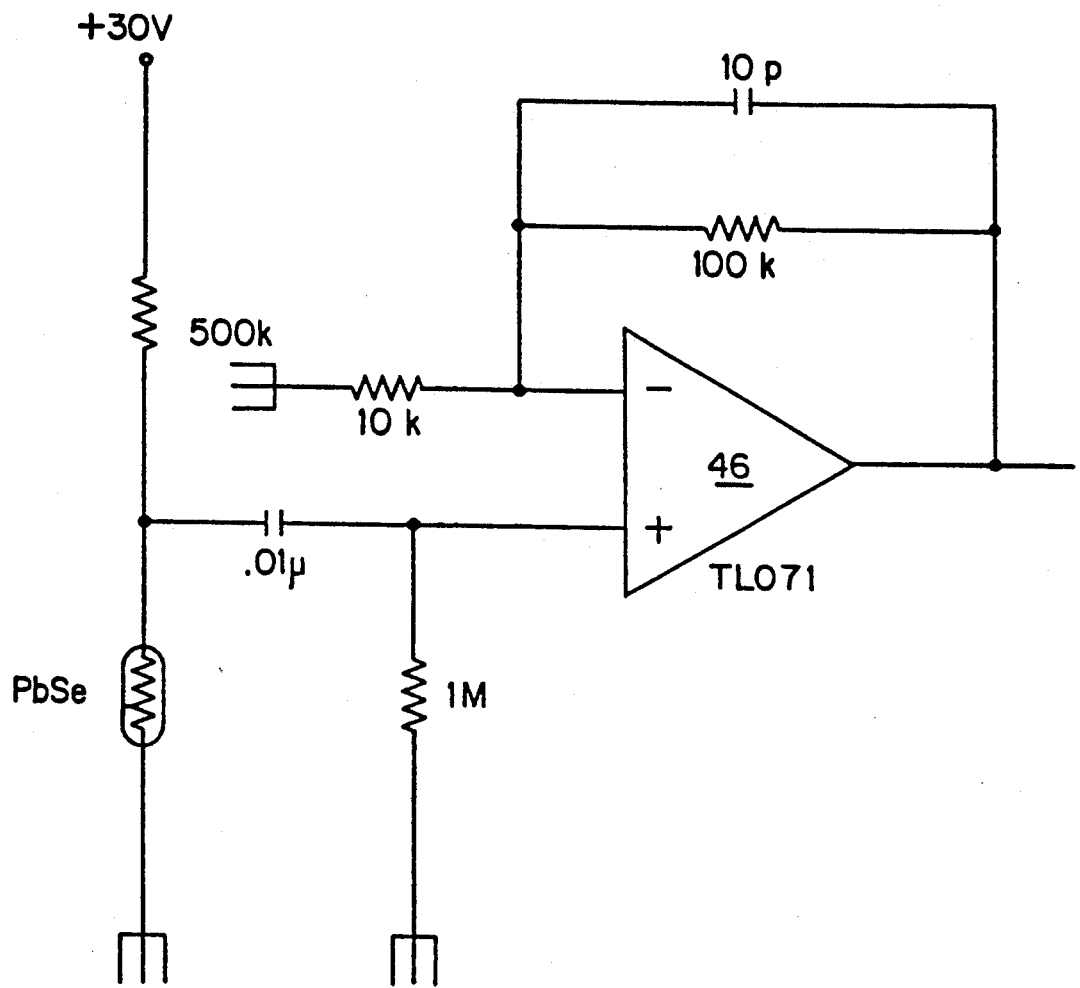
FIG. 4 schematically illustrates the preamplifier circuit for PbSe detector.

A housing/mounting assembly was fabricated so that detector, 24 in FIG. 2, could be mounted in the focal plane of the monochromator with the preamplifier electronics in close proximity. A 30.0 volt regulated power supply was used initially as the power supply for the detector 24. The preamplifier circuit, consisting of a BIFET operational amplifier 46 and associated components, is shown in FIG. 4. The amplified signal from the preamplifier was applied to the input of a Princeton Applied Research Model 128A lock-in amplifier (Princeton Applied Research, Princeton, N.J.), not shown The radiation from the flame was modulated with a Princeton Applied Research Model 125A variable speed chopper (Princeton Applied Research, Princeton, N.J.) at a chopping frequency of 86 Hz. Output from the lock-in amplifier was displayed on a Varian Aerograph stripchart recorder. The PbSe detector 24 was used in all studies utilizing the monochromator.

Wavelength-selective studies were also conducted with a high-pass filter in conjunction with the PbSe detector 24 in FIG. 2 to isolate the 4.3 μm emission band. In this embodiment, a high-pass filter (Corion Corp., Holliston, Mass.) with a short wavelength cutoff of 3.5 μm was mounted in a housing in front of the PbSe detector 24. Since the long wavelength response of the detector 24 only extends out to about 5 μm (See Table II), this arrangement effectively isolates the 4.3 μm band without the need for a monochromator.

The Varian Techtron burner assembly 20 (Varian Instruments, Palo Alto, Calif.) used for the non-dispersive studies is also used as the sample introduction system in the dispersive studies. A flame shield is constructed of sheet stainless steel and attached to the burner assembly to minimize the effect of drafts on the flame. Flow of combustion and other gases to the burner 20 was controlled using Brooks Instrument gauges and flow meters (Brooks Instrument Division, Emerson Electric Co, Hatfield, Pa.). Three fuel/oxidant mixtures are employed in this study: hydrogen/air, acetylene/air, and hydrogen/20% oxygen-80% argon.

The liquid chromatograph used in this study was a Varian Model 5000 (Varian Instruments, Palo Alto, Calif.), equipped with a MCH-5 reverse-phase column. The interfacing of the Model 5000 and the Varian burner assembly 20 was accomplished initially by simply attaching a polycarbonate tube of similar diameter to the stainless steel outlet tube of the MCH-5 column by means of a zero volume stainless steel coupler. After initial experimentation and testing, a telfon T-coupler 26 was added. This allowed other solvents to be mixed with the chromatographic effluent prior to aspiration by the burner 20. The purpose of the coupler 26 is to improve sample aspiration by the burner/nebulizer 20 by mixing the chromatographic effluent with water prior to nebulization; alternatively, the same device permitted the direct introduction of column effluent into the burner 20 without prior mixing with water if desired. All chromatographic results reported are obtained using the T-coupler 26.

Methanol and water are used as the solvents in all chromatographic runs. The methanol is HPLC grade and the water is triply deionized. All standard compounds are reagent grade.

Chromatographic runs were done using various mixtures of methanol and water as well as pure water as the eluent Injection loops of either 10 or 50 microliter volume were employed in all runs. Samples were prepared from mixtures of pure compounds and were loaded into the sample loop using a .1-mL syringe. Samples were introduced onto the column by means of the conventional rotary valve. All runs were done using water as the make-up solvent 27 in the T-coupler 26 prior to aspiration by the burner assembly 20.

Initial non-dispersive studies aimed at determining the feasibility of monitoring infrared emission from a combustion flame were conducted using thermistor detectors. The flake thermistors used in this study fall in the category of thermal detectors as described in Putley (Putley, E. H. In *Optical and Infrared Detectors*, Keyes, R. J., Ed.; Springer-Verlag: Berlin, 1980, Chapter 3) and are fabricated so that the actual detector mass is kept as low as possible, thereby producing a faster response time (75 ms) and increasing the relative response by keeping the heat capacity of the detector low.

Although flake thermistors are more sensitive than their nonflake counterparts, they were not found to be sensitive enough to detect the levels of infrared energy present when the radiation from the flame was dispersed by the 0.5-m monochromator. This lack of response in the dispersive mode is attributed, at least in part, to the relatively high dispersion obtained with the 0.5-m monochromator. Used in a non-dispersive mode (i.e., with the thermistor placed about 30 cm from the flame), however, these detectors are easily able to monitor changes in infrared energy emitted from the flame as a result of introducing microliter amounts of carbon-containing compounds into the flame.

Figure 3:
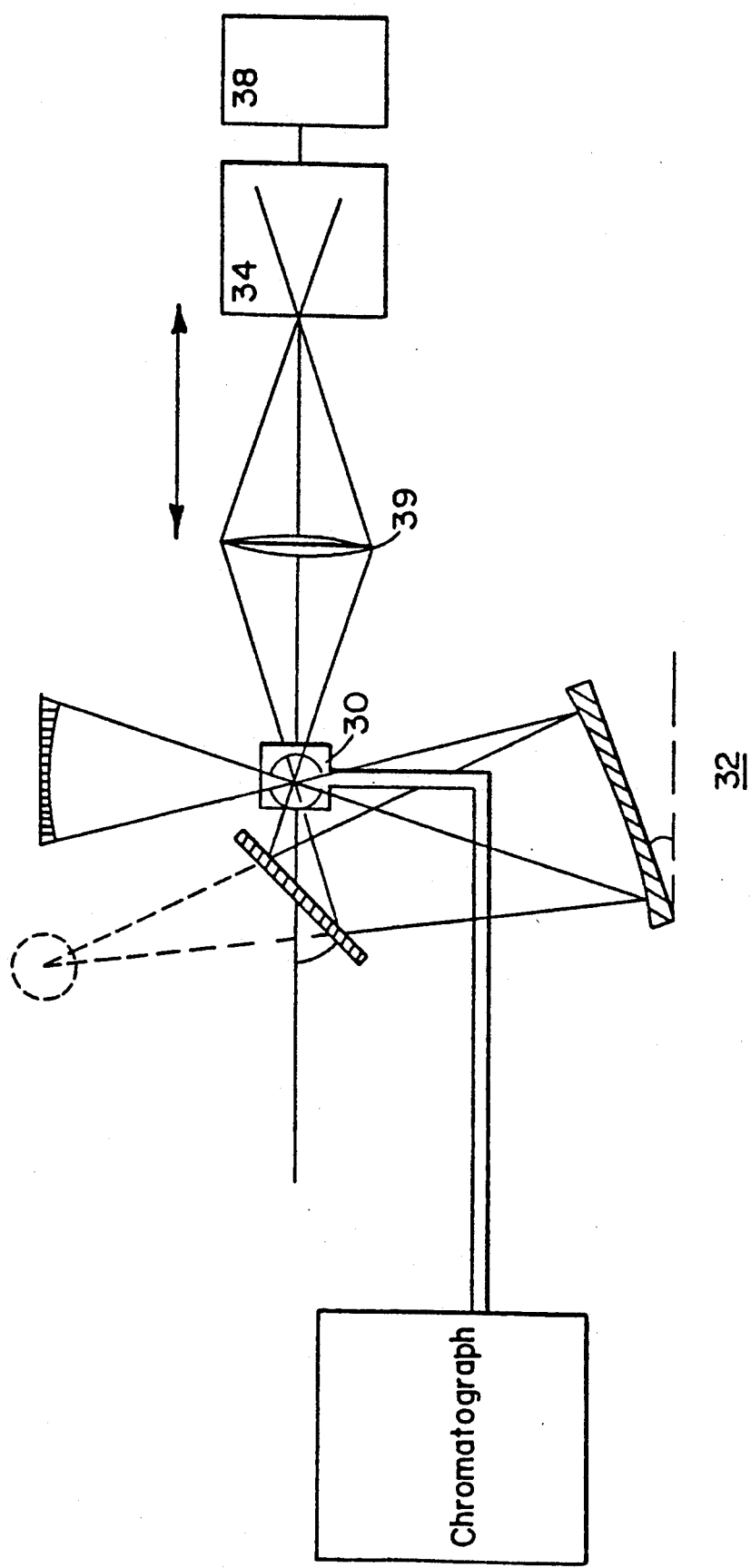
FIG. 3 schematically illustrates an optical system for use in Fourier Transform spectrometer studies.

In a preferred embodiment shown in FIG. 3, the effluent from a chromatograph is analyzed by fast Fourier Transform interferometery. A burner/nebulizer 30 is used for vaporizing and exciting liquid chromatograph effluent sample. The burner assembly 30 may be either the burner previously discussed with respect to FIG. 2, or the burner assembly illustrated in FIGS. 16 and 17, as will be hereinafter discussed in detail with respect to Experiment 2. After the sample is introduced into the flame, the emitted infrared radiation is focused by a three mirror assembly 32 through lens 39 and thereby directed into an interferometer 34 intrinsically having an amplifier and infrared detector. The distance between lens 39 and interferometer 34 is about 10 cm. The output of the interferometer 34 is connected to a computer 38 to analyze the collected data by a Fast Fourier Transform to obtain the spectral response of the sample and the molecules of interest contained therein.

Figure 5:
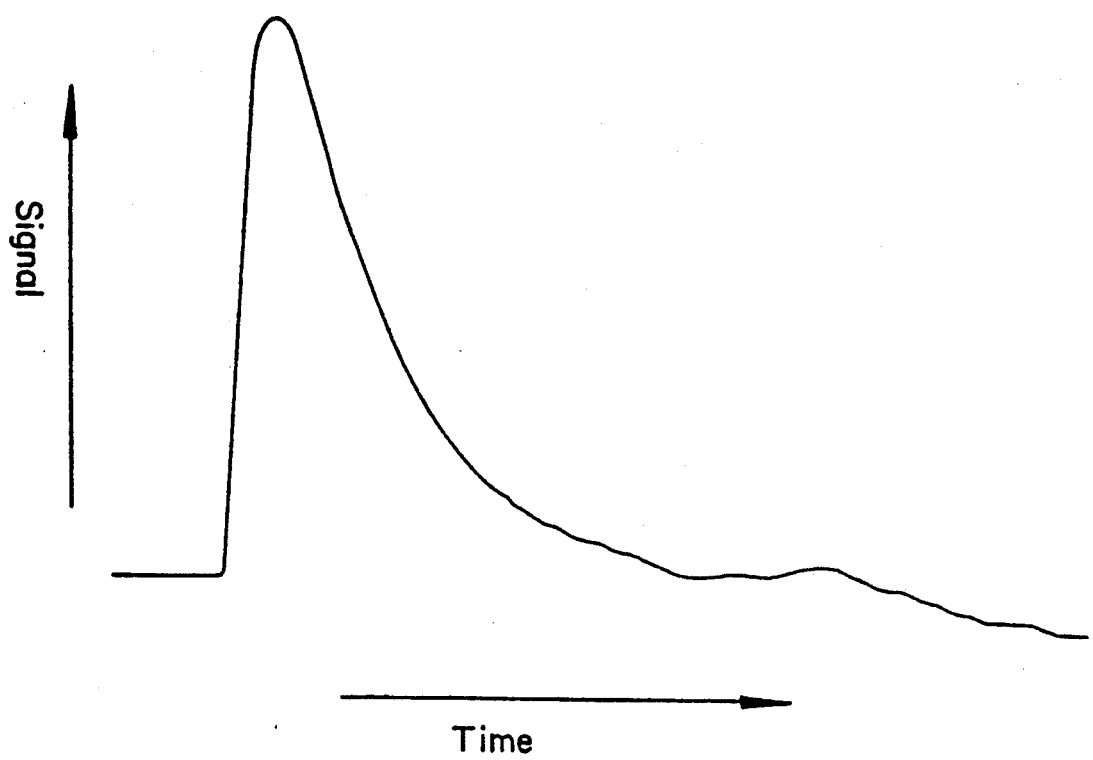
FIG. 5 graphically illustrates the signal profile as a function of time for a 50 $\mu L$ injection of toluene.
Figure 6:
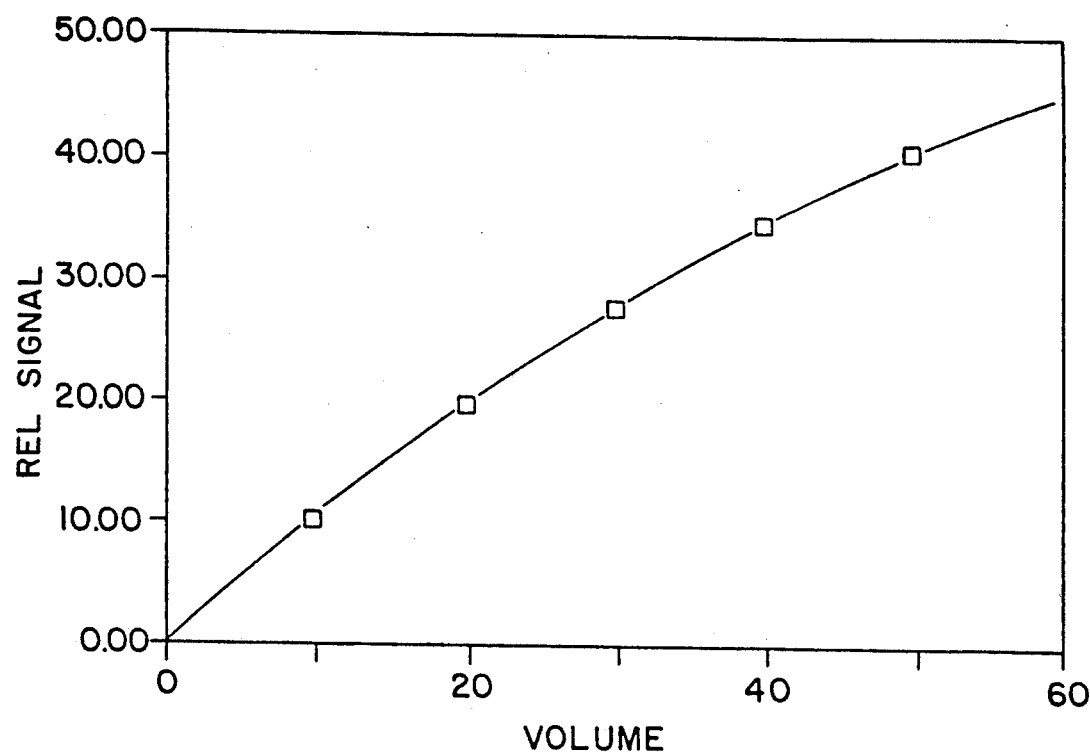
FIG. 6 graphically illustrates the peak height signal as a function of injection volume in microliters for toluene.
Figure 7:
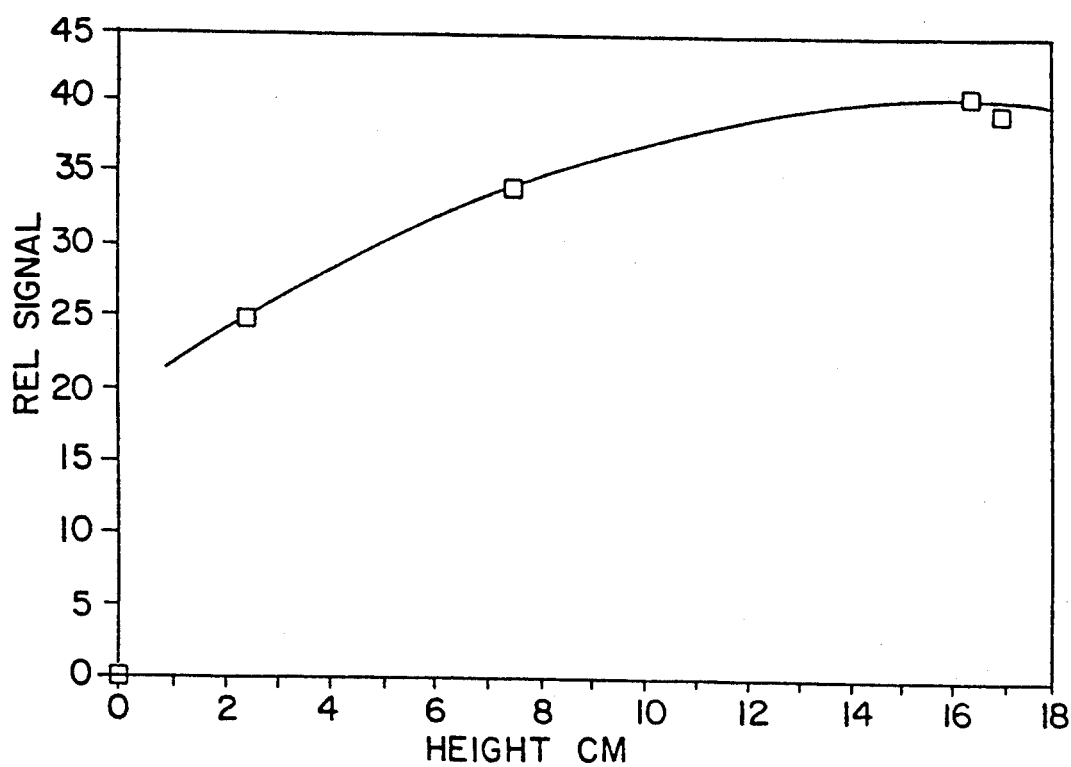
FIG. 7 graphically illustrates the effect of observation height above the burner on the signal when pure ethanol was aspirated into the flame.

Using the apparatus illustrated in FIG. 1, samples were introduced into the hydrogen/air flame by injection using a sample injection device similar to that described earlier,(Busch, K. W.; Howell, N. G.; Morrison, G. H.; *Anal. Chem.* 1974, 46, 1231). FIG. 5 shows the signal profile obtained of time for a 50 $\mu$L injection of toluene. FIG. 6 shows a plot of signal (i.e., peak height) as a function of injection volume in microliters. Similar plots were obtained for injections of various volumes of methanol. These results suggest that it is possible to observe infrared emission from the hydrogen/air flame as a result of the combustion of small amounts of organic compounds. The results also establish that the emission observed is a function of the amount of sample introduced into the flame. Subsequently, a series of studies was conducted to determine the effect of various flame parameters on the infrared emission observed. FIG. 7 shows the effect of observation height in the flame on the signal obtained when pure ethanol was aspirated into the flame. These results were obtained non-dispersively with the thermistor detector located 25 cm from the flame. To limit the field of view seen by the detector, a stainless steel tube 10 cm long with a 1.2 cm diameter is attached to the detector housing. Using this arrangement, maximum emission was found to occur just above the tip of the visible portion of the secondary combustion zone. Studies of the effect of fuel-to-oxidant ratio with this system revealed that flame stoichiometry had less of an effect on the signal than observation height in the flame. Over the range of flame stoichiometries available, the maximum signal was always observed just above the tip of the flame and did not appear to be greatly affected by flame stoichiometry. A fuel-to-oxidant ratio of 0.53 was used in all subsequent studies because it gave a flame of convenient size (i.e., not too tall) that was not greatly affected by drafts. Since a stoichiometric hydrogen/air flame corresponds to a fuel-to-oxidant ratio of 0.4, the flame used in these studies was slightly fuel rich.

Studies on the influence of flame parameters on the signal observed are consistent with the hypothesis that the majority of the infrared emission observed is due to emission from the excited combustion products. Since complete combustion of organic samples to carbon dioxide and water is likely to be achieved only relatively high in the flame, if at all, the concentration of $CO_2$, for example, is likely to be greatest relatively high in the flame. The increase in the concentration of $CO_2$ with increasing distance from the burner is counteracted by a decrease in temperature as well as dilution effects from entrained air. The combination of these factors would then be expected to result in a maximum signal at some point above the burner. From the results obtained, the point at the tip of the visible portion of the secondary combustion zone corresponds to the maximum concentration of excited combustion products. Since this maximum is located at the tip of the flame, it is not surprising that the signal observed is not greatly affected by the fuel-to-oxidant ratio.

Figure 8:
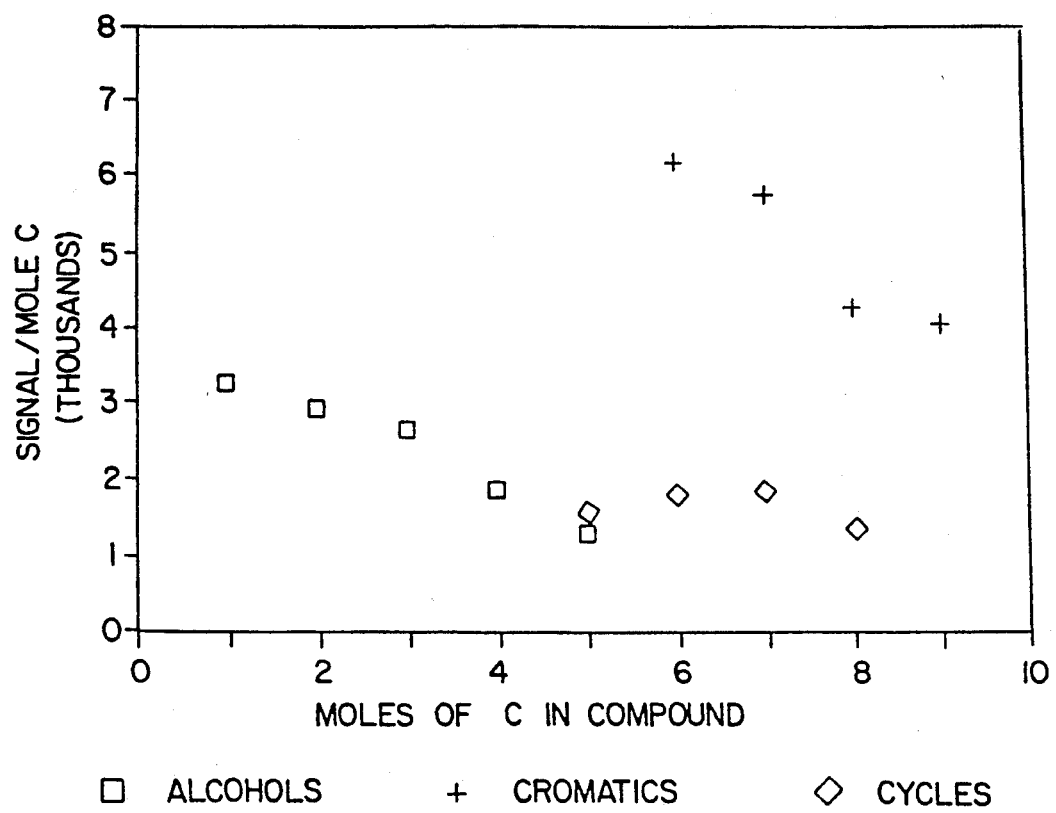
FIG. 8 graphically illustrates the signal obtained per mole of carbon as a function of the number of carbon atoms in the molecule.

A series of studies was conducted to determine the effect of compound structure on the signal observed. Three homologous series of organic compounds were selected on the basis of availability: alcohols, cycloalkanes, and aromatics. FIG. 8 shows the signal per mole of carbon as a function of the number of carbon atoms in the molecule at a particular observation height. If all the compounds introduced into the flame burned completely to carbon dioxide, a horizontal plot would be obtained. FIG. 8 shows that the signal obtained per mole of carbon in the compound depends on the number of carbons in the compound as well as the compound type. The decrease in response observed with the longer chain compounds is probably a result of incomplete combustion of the compound to carbon dioxide. Likewise, the difference in response between saturated and aromatic compounds is undoubtedly a result of differences in the ease and extent of combustion. Regardless of the actual mechanism of signal production, it is clear that the response of the system is compound dependent. As a result, quantitative determination is possible using individual calibration curves.

To improve the sensitivity of the system to the point where it would be possible to use the monochromator for wavelength studies, a PbSe photoconductive detector was evaluated using the apparatus illustrated in FIG. 2. These detectors are about two orders of magnitude more sensitive than the thermistor and respond over the wavelength range from 1 to 5 $\mu$m. Other detectors suitable for flame infrared emission detection are indium antimonide and mercury cadmium telluride. For this embodiment, the lead selenide detector was selected on the basis of the cost effectiveness. Since PbSe detectors are intrinsic semiconductors (i.e., not doped), the long wavelength response cutoff is determined by the inherent energy gap between the valence band and the conduction band. (Boyd, R. W.; *Radiometry and the Detection of Optical Radiation;* John Wiley: New York, 1983, Chapter 10). As a result, the detector response drops off rapidly as the photon energies approach the bandgap energy. When operated at room temperature peak response occurs at 3.8 $\mu$m. When the device is operated with cooling, the peak response is shifted to longer wavelengths. In addition to the shift in the wavelength of peak response, the dark resistance and time constant also change with cooling. For example, according to manufacturer's specifications, cooling causes the dark resistance to increase by 2.5%/°C. and the time constant to increase by 5.3%/°C. Cooling with dry ice ($-77°$ C.) or liquid nitrogen ($-196°$ C.) increases the detectivity (D*) by an order of magnitude. The device used in this study was provided with a thermoelectric cooling system which could maintain the detector at $-10°$ C.

Figure 9:
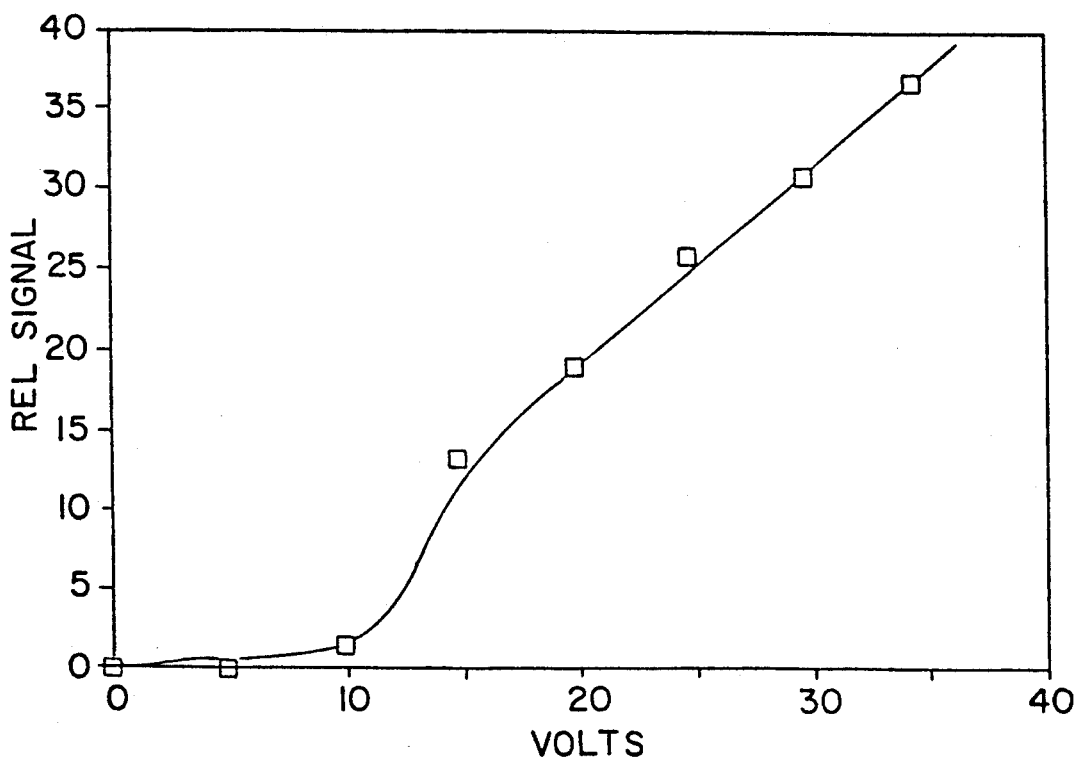
FIG. 9 graphically illustrates the effect of detector bias voltage on the signal observed at 4.3 $\mu m$ when 10% methanol/water mixture was pumped into the burner from the liquid chromatograph at 2 mL/minute.

In studying the influence of operating conditions on the performance of the PbSe detector, two factors were investigated: the effect of applied voltage and the effect of chopping frequency. FIG. 9 shows the effect of bias voltage on the signal observed at 4.4 μm when a 10% methanol/water mixture was pumped into the burner from the liquid chromatograph at a constant rate of 2 mL/minute. From the figure, it can be seen that a threshhold voltage of 10 volts is required to produce a minimum measurable signal. For bias voltages above 15 volts, the signal increases almost linearly with increasing bias voltage. A bias voltage of 30 volts was employed in all subsequent studies in Experiment 1.

Throughout all of the above experiments, it was observed that the noise on the signal appeared to be constant. In an effort to determine potential sources of noise in the system, the filtered dc power supply which was used to provide the bias voltage was replaced with a 30 volt battery. This substitution decreased the observed noise by a factor of five. For this reason, the 30 volt battery was used in place of the dc power supply to provide the bias voltage in all subsequent experiments in Experiment 1.

Figure 10:
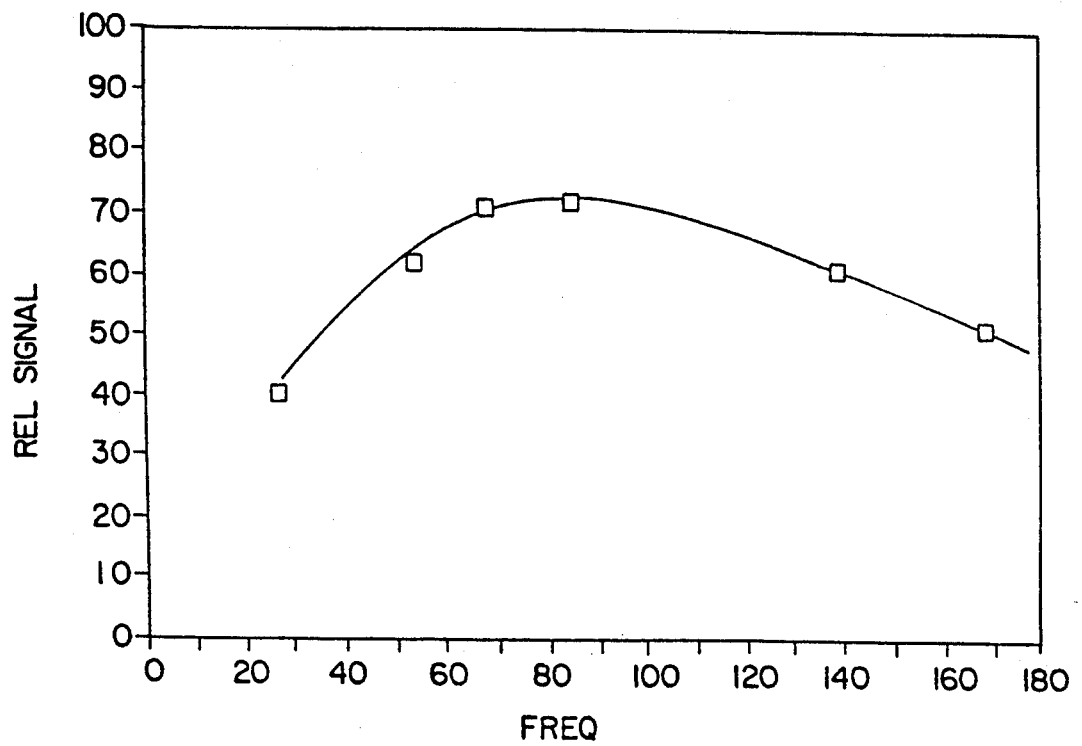
FIG. 10 graphically illustrates the effect of chopping frequency on the signal observed when pure ethanol was aspirated into the flame at a steady rate.

The other factor which was studied was the effect of chopping frequency on the signal observed when pure ethanol was aspirated at a steady rate into the flame. FIG. 10 shows the results of this study. From the figure, it can be seen that the maximum signal is obtained for a chopping frequency of about 90 Hz. On the basis of this study, a chopping frequency of 86 Hz was employed in all studies in Experiment 1 with the PbSe detector.

The 0.5-m monochromator used in this study was selected solely on the basis of its availability in the laboratory and not on the basis of optical considerations. In fact, a shorter focal length dispersion system would have been preferable. When equipped with a 150 groove/mm grating, the system had a reciprocal linear dispersion of 13 nm/mm which is much lower than is necessary for infrared work of the type described here. Furthermore, since the entrance slit was wider (3 mm) than the width of the PbSe detector (1 mm), the dispersion system was characterized by a trapezoidal slit function with a base equivalent to 0.04 μm and a flat peak equivalent to 0.01 μm. In spite of the non-ideal slit function, the effective spectral bandwidth of the system was much less than the halfwidth of the molecular emission bands (0.4 μm) being studied, so instrumental distortion of the band shapes was not a problem. Since high resolution is not required, a shorter focal length system with a correspondingly higher value for the reciprocal linear dispersion would have permitted more energy from the infrared bands to have been focused on the detector rather than dispersing it on either side as occurs with the current system. Measuring the integrated band intensity with a lower resolution system would therefore be expected to increase the sensitivity of the system significantly.

A hydrogen/air flame was selected because of its low background in the vicinity of the 4.4 μm $CO_2$ band. FIG. 11 shows a comparison of the spectra obtained with the system for an hydrogen/air flame and an acetylene/air flame using the PbSe detector. The spectrum obtained with the acetylene/air flame is typical of the results obtained when a carbon-containing fuel is used and is in agreement with the spectrum obtained by Plyler (Plyler, E. K.; *J. Res. Nat. Bur. Stand.* 1948, 40, 113) for a Bunsen flame. Since the 4.4 μm emission band is due solely to excited carbon dioxide, it is not present to any great extent in the hydrogen/air flame. The band at 2.7 μm, on the other hand, is due to both water and carbon dioxide and is therefore present in both flames.

Compared with the hydrogen/air flame, no significant difference in the spectrum was observed when the hydrogen/20% oxygen-80% argon flame was used. It was anticipated that the use of the hydrogen/20% oxygen-80% argon flame might produce a lower background in the 4.4 μm region because, compared with air, this gas mixture did not contain carbon dioxide. Since a reduced background was not observed, use of the 20% oxygen-80% argon gas mixture was discontinued.

Figures 12A, 12B:
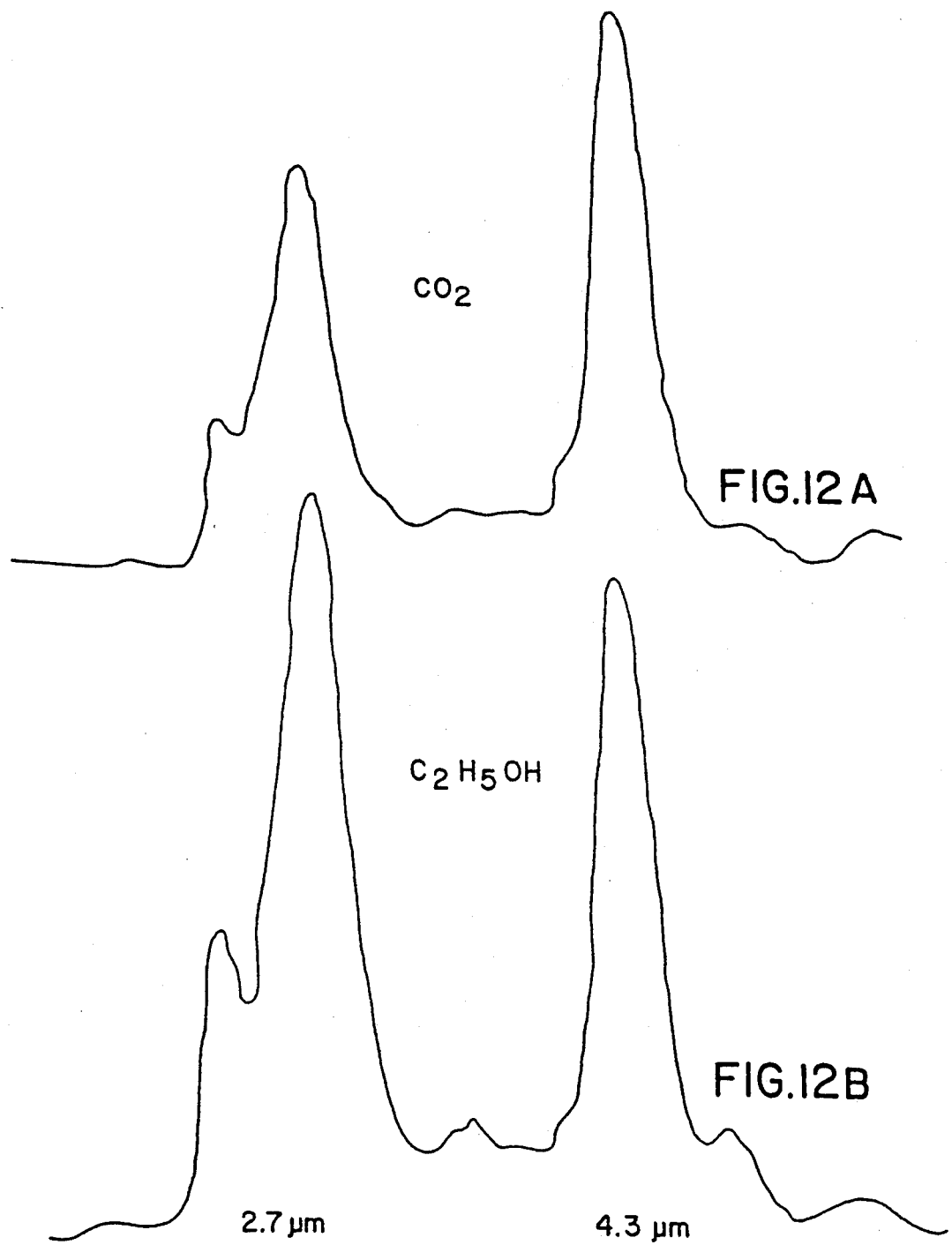
FIGS. 12A to 12B are the infrared spectra obtained with the system when $CO_2$ and ethanol were introduced into the flame.

To prove that the emission observed at 4.4 μm when organic compounds were introduced into the hydrogen/air flame was indeed due to carbon dioxide emission, the spectrum of carbon dioxide gas introduced into the flame was compared with the spectrum obtained when ethanol was introduced into the flame. FIG. 12 shows that similar spectra are produced regardless of whether an organic compound is burned or carbon dioxide is introduced directly into the flame.

Figure 13:
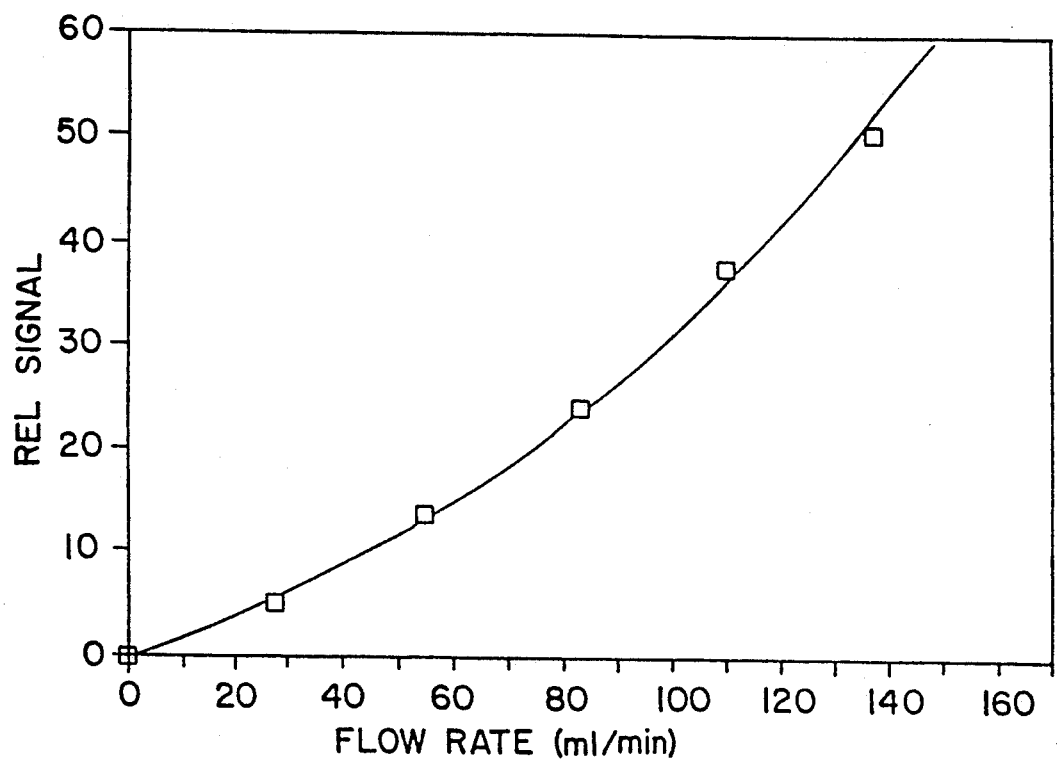
FIG. 13 graphically illustrates the signal observed at 4.3 $\mu m$ as a function of $CO_2$ flow rate.
Figure 14:
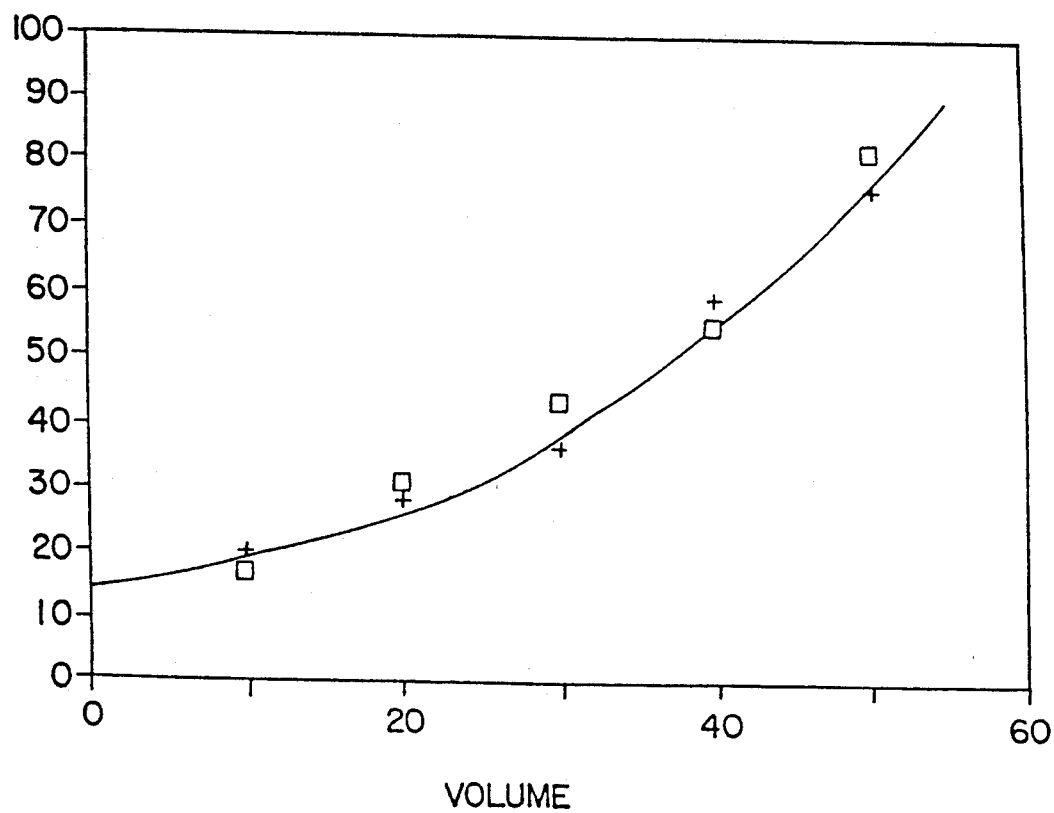
FIG. 14 graphically illustrates the signal obtained at 4.3 $\mu m$ as a function of volume of ethanol injected into liquid chromatograph.

FIG. 13 shows the signal obtained at 4.4 μm as a function of the flow rate of carbon dioxide introduced into the flame. FIG. 14 shows the signal obtained when various volumes of ethanol were eluted from the liquid chromatograph. The zero offset observed with the liquid chromatograph was attributed to the background signal due to the methanol in the eluting solvent. Both experiments produced calibration curves which curved upwards in contrast to the results obtained in the nondispersive studies with the thermistors. This upward bending of the growth curve is reminiscent of the effect caused by ionization when alkali metals are introduced into the flame. Whatever the explanation, the effect clearly involves only carbon dioxide since it is not observed when both the carbon dioxide and water bands are monitored simultaneously.

Only two intense bands (2.7 μm and 4.4 μm) were observed over the wavelength interval accessible by the PbSe detector. Of the two bands, the 4.4 μm band was deemed the most useful analytically since it arises solely from the presence of carbon dioxide. Since it did not appear necessary to vary the wavelength, the monochromator was replaced by a high-pass optical filter in an effort to increase sensitivity by increasing optical throughput. By this means, the wavelength response of the system was limited at lower wavelengths by the short-wavelength cutoff of the filter and at higher wavelengths by the response of the detector itself. The substitution of the filter for the monochromator resulted in an increase in sensitivity of about 2-3 orders of magnitude.

Figure 15:
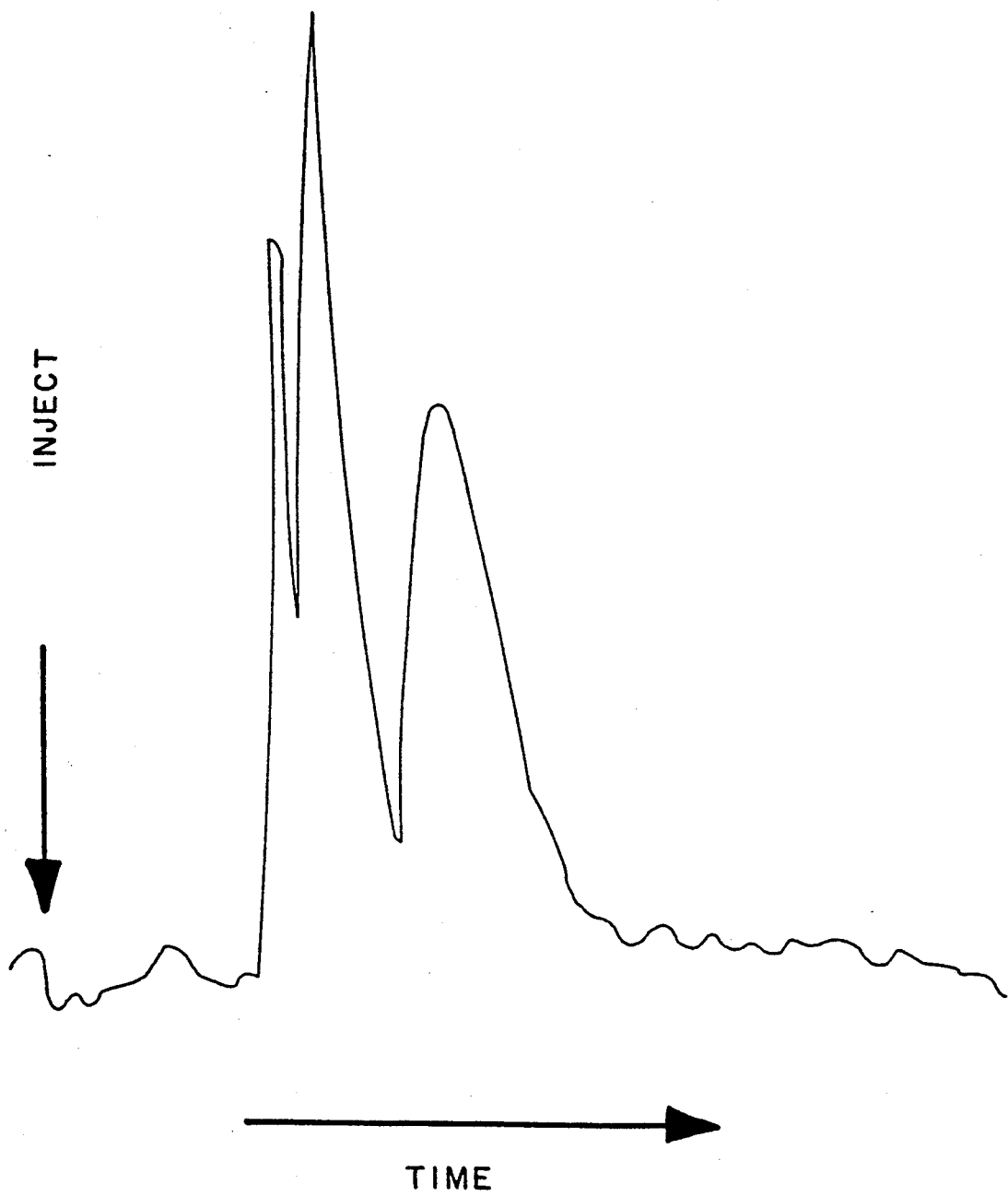
FIG. 15 is the chromatogram obtained when 50 $\mu L$ of an equivolume mixture of methanol, ethanol and propanol were eluted from the liquid chromatograph. The order of elution was methanol, ethanol, propanol.

To demonstrate the potential of infrared emission as a means of detection of organic compounds which have been introduced into the flame, a mixture of methanol, ethanol, and propanol was separated by means of liquid chromatography and detected by means of infrared emission using the PbSe filter arrangement. FIG. 15 shows the results obtained for a 50 μL injection of an equivolume mixture of the three components.

The infrared emission at 4.4 μm provides a sensitive means of detecting small amounts of organic samples introduced into the flame. Since the emission wavelength does not vary, a relatively low-cost filter instrument can be constructed to monitor the desired emission. The detector is suitable for application to both liquid and gas chromatography. The use of the detector with a gas chromatograph is in some respects easier than with a liquid chromatograph because of the absence of the background signal from the eluent which is present when methanol/water mixtures are used. However, as will be discussed later, the dual beam system can be used to remove the presence of interfering background from the eluent.

The experiments reported in this application were conducted with equipment available in the laboratory. The burner assembly used was selected on the basis of its availability in the laboratory, and is not necessarily an ideal system for chromatographic detection because the flame produced with the burner is much larger than is actually necessary. A more appropriate burner for this application is described below under Experiment 2.

EXPERIMENT 2

Figure 16:
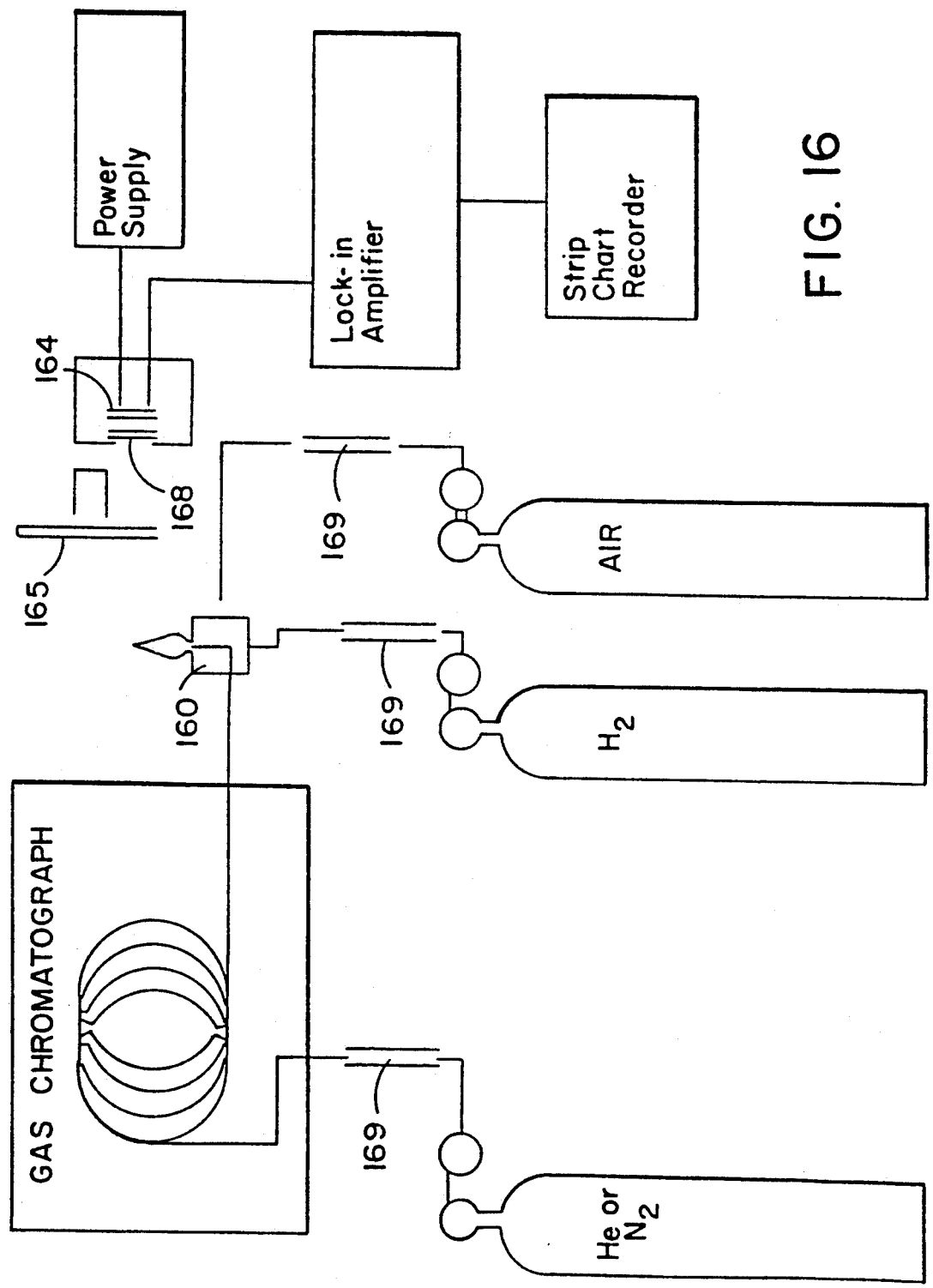
FIG. 16 schematically illustrates the apparatus used in Example 2.

The experimental arrangement used in this second study is shown in FIG. 16. A Hamamatsu lead selenide photoconductive cell (P2038-01, Hamamatsu Corp., San Jose, Calif.) was employed as the infrared detector, and was positioned to view a hydrogen/air flame maintained on a specially designed burner 160 described below. A high-pass filter 168 (Corion Corp., Holliston, Mass.) with a short wavelength cutoff of 3.5 $\mu$m was mounted in a housing in front of the PbSe detector 164 as described in Experiment 1 to give a detection system with a response from 3.5 $\mu$m to about 5 $\mu$m. The power supply and pre-amplifier circuit used in this study for the detector were also as described in Experiment 1. Radiation from the flame was modulated at 90 Hz by a chopper 165 which was constructed in the laboratory. The modulated signal was applied to the input of a Model 128A Princeton Applied Research lock-in amplifier (Princeton Applied Research, Princeton, N.J.), and the amplified signal was displayed on a Varian Aerograph stripchart recorder. A Model 3120TX Bascom-Turner digital data acquisition system (Bascom Turner Instruments, Norwood, Mass.) was used to store and display data for some experiments where peak area measurements were made.

The oven and injection port of a Model 705 Varian Aerograph gas chromatograph (Varian Instruments, Palo Alto, Calif.) were used in conjunction with a $\frac{1}{4}$" stainless steel column packed with 10% OV-101 on Chromasorb W-HP to evaluate the performance of the flame infrared emission detection system for gas chromatography. A vent in the side of the gas chromatograph was utilized to connect the GC column to the detection system. The interface between the $\frac{1}{4}$" GC column and the 0.10" OD stainless steel capillary from the burner system was made by means of an adapter machined from brass.

Mounts and detector shields were fabricated from aluminum sheet metal stock, and were used to isolate the detector from the heat produced by the GC oven and from drafts of air or other heat sources (the detection system is sensitive enough to detect the heat from persons moving in the room). The sides of the baffle surfaces facing the detector were painted flat black to avoid reflection of Infrared energy from the surroundings into the aperture of the detector unit.

Column carrier gas flow and pressure were monitored with Brooks Instrument Division flow meters 169 of FIG. 16 (Brooks Instrument Division, Emerson Electric Co., Hatfield, Pa.) calibrated for helium flow. A metering valve and separate shut-off valve were installed in the gas line of the helium supply. All carrier gas metering was done upstream of the GC and column.

All experimental runs were made after a 30 minute warm-up time to allow the environment of the detector to reach thermal equilibrium. The radiation from the flame was chopped at 90 Hz, and a detector bias voltage of 30 volts, obtained from a bank of batteries, was employed. Injections were made using standard 10 and 50 microliter syringes (Hamilton Co., Reno, Nev.) for liquid samples, and a 500 microliter gas syringe (Hamilton Co., Reno, Nev.) for gas samples. All chromatograms were obtained with a carrier gas flow rate of 40 mL/min. unless stated otherwise. All compounds used were reagent or spectroscopic grade with the exception of pentane which was Eastman 98%.

In all experiments in which detector response for different carrier gas flow rates was being measured, the temperature of the GC oven was maintained at a sufficiently high value to avoid sample interactions with the stationary liquid phase as the sample passed down the column. This procedure minimized any column effects which might alter the readings obtained in these studies.

For injections smaller than 0.5 microliter, solutions of the compound of interest were prepared in a solvent with a higher boiling point than the sample which could be easily separated from the sample by the column. The temperature of the oven would then be held above the boiling point of the compound of interest, but below that of the solvent in order to maximize separation and minimize column effects on the sample.

Small quantities of various gaseous samples (Matheson Gas Products, Secaucus, N.J.) were collected over water from lecture bottles. Chromatograms of these gas samples were obtained by injecting 500 $\mu$L of the gas into the chromatograph with a gas syringe.

The chromatogram obtained for unleaded gasoline was obtained by holding the column temperature at 55° C. for 4 minutes and then ramping the temperature up to 200° C. over a period of 7 minutes.

The detector system used in this study was described above with respect to FIG. 2, and the same conditions for operation of the system were found to be satisfactory for this work. Due to space considerations, the commercial chopper used in the previous study was replaced with a smaller unit which was fabricated in the laboratory and used a synchronous AC motor. Since no optical components to focus the radiation on the detector were employed, it was important to place the detector/chopper combination in close proximity with the flame, and this could be accomplished only with a small chopper. Background signal from a variety of sources was minimized by minimizing the field of view of the detector and shielding the small area viewed by the detector with sheet metal baffles whose interior surfaces were painted flat black to minimize reflections. This shielding also kept air drafts that would affect the flame to a minimum. The use of a 10-cm diameter spherical mirror used as the focusing element in the previous study was rejected as this would have increased the area requiring shielding to an unacceptable level.

The atomic absorption burner unit used in the previous study was replaced by a smaller specially fabricated pre-mixed burner(FIG. 17) because the flame produced by the atomic absorption burner was much larger than necessary.

Figure 17A:
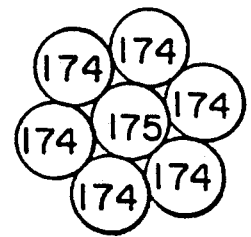
FIGS. 17A to 17C schematically illustrate the burner assembly for Example 2.
Figure 17B:
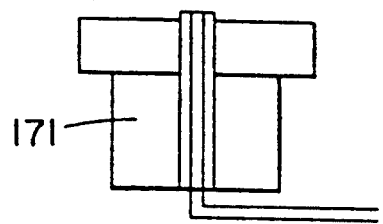
Figure 17C:
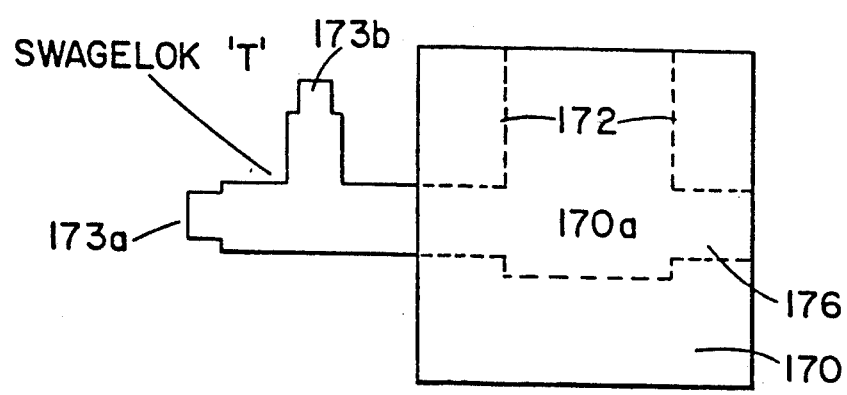

A special burner shown schematically in FIG. 17, was designed to produce a small hydrogen/air pre-mixed flame. The burner was machined from a block of aluminum, and consisted of a burner body 170 with a mixing chamber 170a and a burner head 171 held in the body 170 by a rubber o-ring seal 172. Openings 173a and 173b in the sides of the burner body permitted the burner to be connected to the combustion gas supplies with Swagelok (Crawford Fitting Co., Solon, Ohio) tube fittings.

The burner system described in this application produces a stable flame of small size by means of an array of stainless steel capillary tubes 174. These tubes 174 were cut to a length of approximately 2.5 cm and permitted the use of very low hydrogen/air support gas flow rates without problems from flashback. The combustion gases issued from the burner head through the circular array (FIG. 17.1) of six stainless steel capillaries of 0.10" OD and 0.06" ID which were cemented in a small hole in the burner head by means of epoxy cement. In the burner design implemented in this application, six capillaries arranged in a circular array were used to form the orifice for the combustion gases.

The circular array of capillaries surrounded a central capillary 175 through which flowed the column effluent directly into the center of the hydrogen/air flame and which, therefore served as a connection between the burner and the gas chromatograph. The central capillary 175 was bent at a right angle to exit the burner body through a side port 176, and was held in place by a rubber seal in a tubing fitting.

The new burner design has several important advantages which should be emphasized. Because the rate of sample addition to the flame is determined solely by the carrier gas flow rate and not by the combustion gas flow rates, the rate of sample addition to the flame may be varied independently of the combustion gas flow rates, thereby avoiding changes in the flame size or stoichiometry. By introducing the sample directly into the flame from the central capillary, peak broadening associated with mixing chambers is avoided. Since the capillary has a small internal diameter (0.06" ID), post-column volume can be kept to a minimum (0.5 mL/30 cm length of tubing). Finally, use of a narrow-bore capillary leads to a high linear velocity gas jet which travels up the center of the flame. (A carrier gas flow rate of 40 mL/min., for example, results in a linear velocity in the capillary of 40 cm/s.) At velocities of 40 cm/s, the transit time for the eluted sample through the 30 cm length of exposed capillary, which runs from the end of the GC column to the flame, is about 750 ms. The linear velocity appears to be sufficient to avoid sample condensation on the walls of the exposed capillary, even in the absence of insulation or heating, for the largest sample volumes investigated in this study.

Initially, it was felt that the effluent capillary should be insulated for the short length that it was exposed to the ambient air outside of the GC oven or the burner body to avoid condensation of the chromatographic effluent. The possibility of having to heat this section of the effluent capillary was also considered. Neither of these options were found to be necessary with any of the samples studied in this experiment regardless of sample size. It is believed that the carrier gas flow rates used in this study (which are typical carrier gas flows for packed GC columns) resulted in a gas velocity in the effluent capillary which was so high that the sample components did not have sufficient time to condense on the walls. Although typical carrier gas flow rates of 30 to 40 mL/min. were used, flows as low as 10 mL/min. were employed without any problems.

Combustion gas flow rates of 300 mL/min. and 800 mL/min. were used for hydrogen and air, respectively. This combination of flow rates gave a flame that was approximately 20 mm high and 3 mm wide and produced the smallest flame that the given combination of metering devices and capillary tube size would permit without the flame pulsating or burning out. The fuel-to-oxidant ratio used corresponds to a nearly stoichiometric mixture, and gave the smallest possible flame consistent with good signal conditions. The best signal-to-noise ratio was obtained when the detector was positioned to view the upper portion of the secondary combustion zone of the flame. In aligning the detector with the proper flame zone, a problem was encountered because the flame itself is invisible. To make the flame visible for alignment purposes, a small amount of 1M sodium chloride was applied to the outside surfaces of the burner capillaries to produce a visible sodium (yellow) emission. This sodium signal lasted for quite some time after the system was aligned, but did not affect the detector signal as seen in the chromatogram of several compounds taken while the flame was still yellow. One advantage of the flame infrared emission detection system is that it does not respond to visible emission from the flame or other ambient sources such as the room illumination. Another advantage of the flame infrared emission detection system which was observed was that nitrogen could be used as a carrier gas in place of helium without any change in detector response.

A warm-up period of approximately 30 minutes was found to be necessary because the signal from the PbSe detector varies with temperature changes in the surrounding area. When all the components of the burner/detector combination reached thermal equilibrium (about 30 minutes), a steady baseline was obtained from the recorder. The baffles surrounding the flame had the added effect of insulating the flame area from the infrared emission from the chromatograph oven, thereby decreasing the background signal from the detector. Prior to the installation of the baffles, changes in the GC oven temperature caused baseline drift which necessitated a stabilization period before further chromatography could be conducted. Shielding almost completely eliminated the effect of GC oven temperature on the detector signal except for a slight baseline change which was thought to be due to changes in the temperature of the carrier gas introduced into the flame. This slight baseline shift can be seen in FIG. 18 which shows a temperature-programmed chromatogram obtained with a 5 $\mu l$ injection of unleaded gasoline. The chromatogram shown in FIG. 18 also demonstrated that the flame infrared emission detector could be employed successfully as a detector in an actual gas chromatographic separation. Since the purpose of this study was to demonstrate the performance of the detector, no effort was made in optimizing or improving the separation conditions for the gasoline sample.

Figure 19:
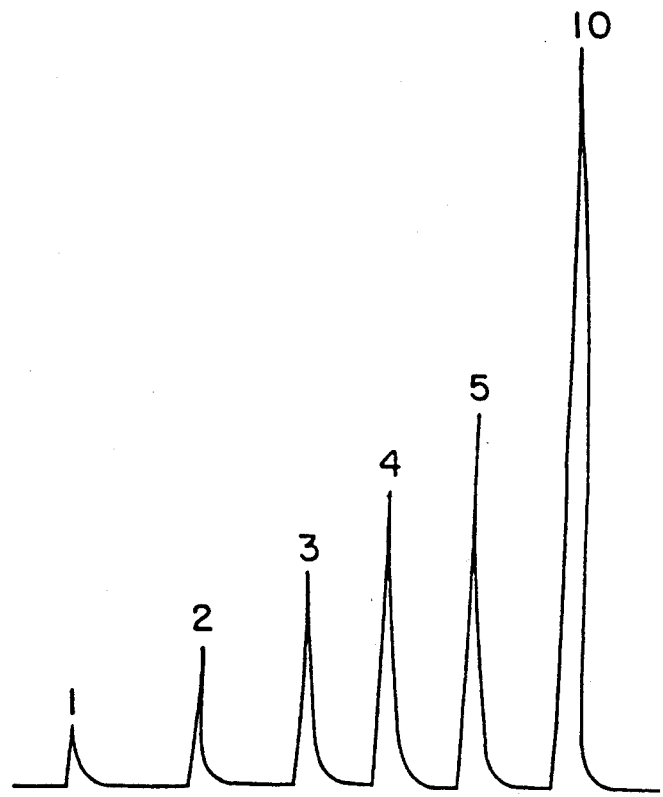
FIG. 19 shows the elution peaks obtained for various volumes of pentane in microliters. Column temperature, 90° C.

FIG. 19 shows the shape of typical peaks obtained from the system when various volumes of pentane were injected into the chromatograph as neat samples. To study the response of the detector itself to various compounds without the influence of column effects, the GC oven was maintained at a temperature above the boiling point of the compound under investigation. This caused the sample to be carried through the column with very little interaction with the stationary phase as indicated by the similarity in the retention times (i.e., within a few seconds of one another) for diverse compounds. This procedure also resulted in peaks with high symmetry as shown in FIG. 19. Such peaks were necessary to enable a comparison of response to be performed on the basis of peak height as opposed to peak area. Since integration of the peaks was not possible with the experimental setup used throughout most of this work, peaks with high symmetry were desired because these peaks showed the best correlation between peak height and the amount of compound present (i.e., peak area). To obtain peaks of similar shape, a carrier gas flow rate of 40 mL/min was used throughout. The use of peak height as a measure of the amount of compound present was justified by the goodness of fit of the data obtained for the calibration curves.

Figure 20:
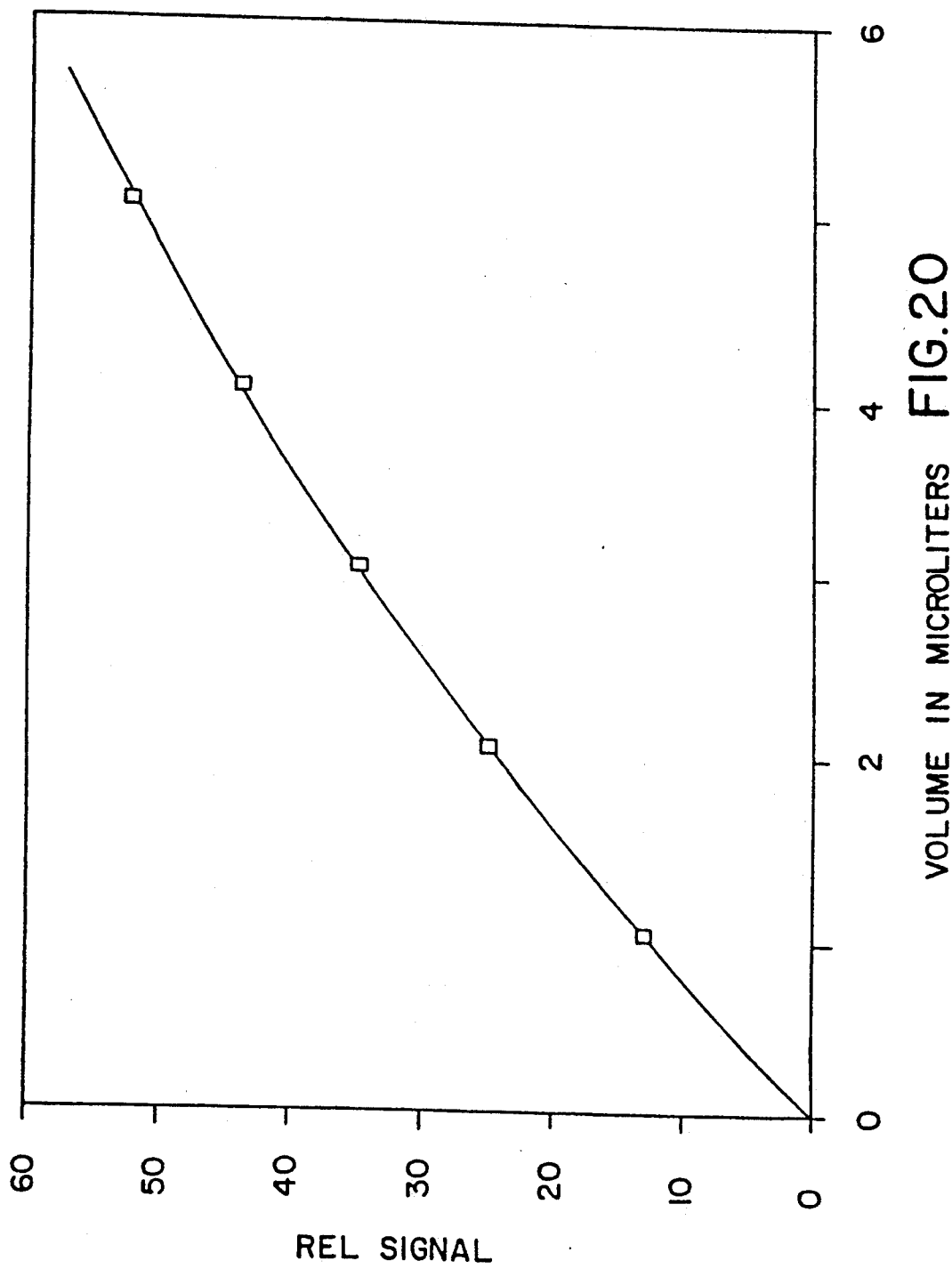
FIG. 20 graphically illustrates peak height versus volume in microliters for dichloromethane.
Figure 21:
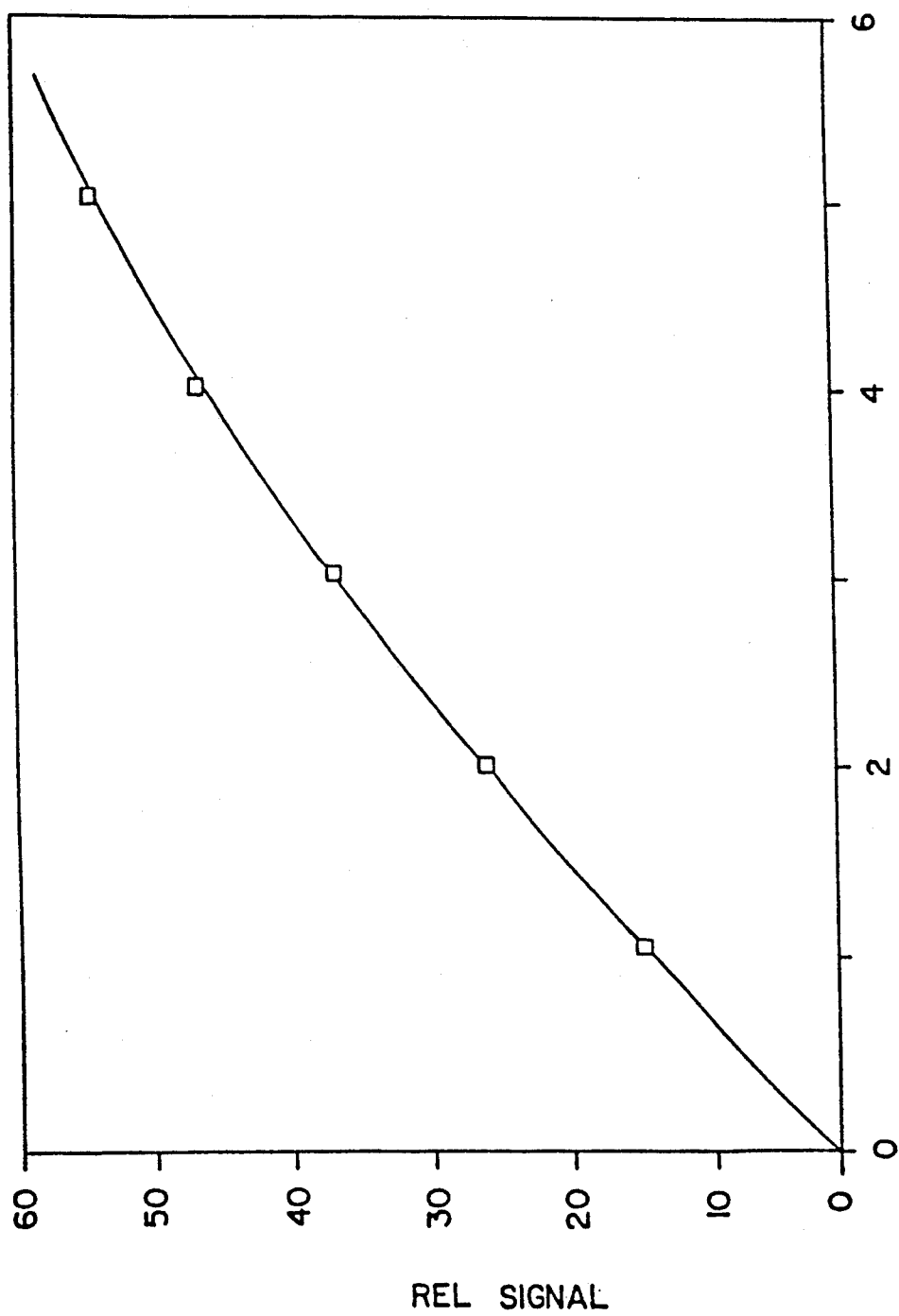
FIG. 21 graphically illustrates peak height versus volume in microliters for trichlorotrifluoroethane.
Figure 22:
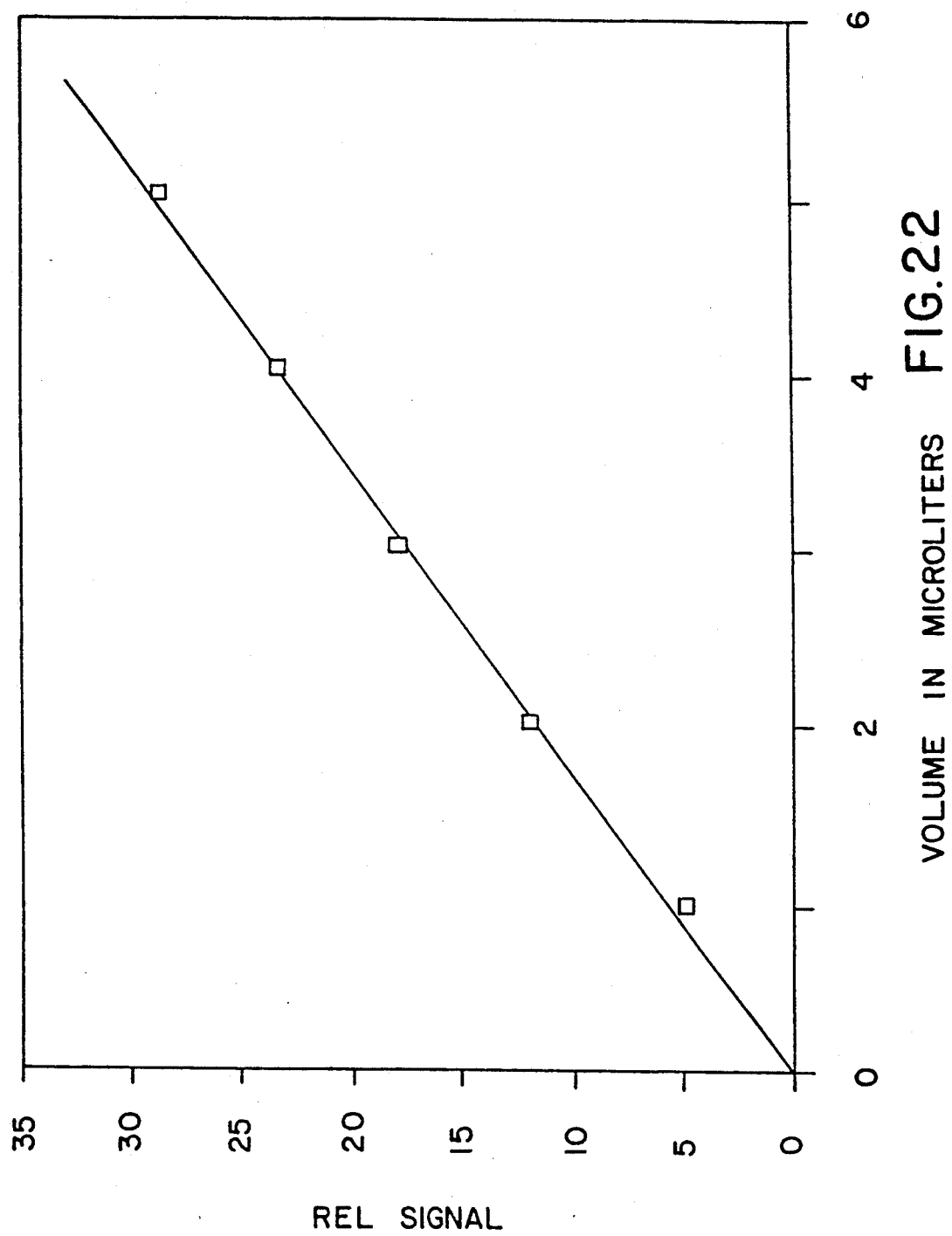
FIG. 22 graphically illustrates peak height versus volume in microliters for carbon tetrachloride.
Figure 23:
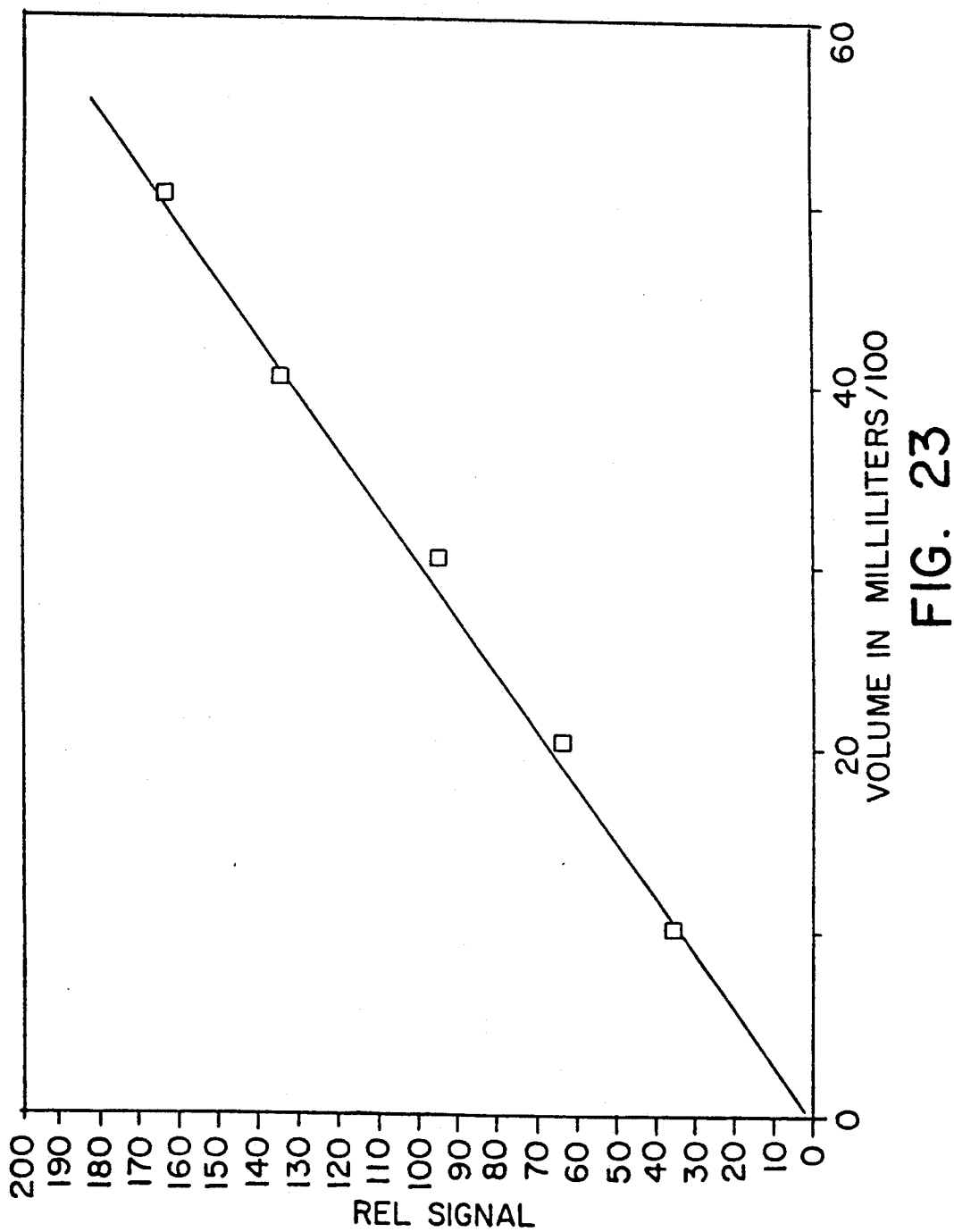
FIG. 23 graphically illustrates peak height versus volume in milliliters for carbon dioxide.

FIGS. 20, 21 and 22 show plots of peak height versus injection volume for dichloromethane, trichlorotrifluoroethane and carbon tetrachloride. These compounds were chosen on the basis of availability and to investigate the ability of the flame to combust them to carbon dioxide. While it was obvious that hydrocarbons and other compounds such as aromatics and cycloalkanes would actually become a fuel in the flame, it was not clear if other compounds such as the halocarbons utilized above would combust sufficiently to give a signal. From the figures, it can be seen that the response is reproducible and is a linear or almost-linear function of the amount injected. This was the case for all of the compounds studied even for those cases where complete combustion to carbon dioxide was somewhat questionable. The calibration curve for carbon dioxide shown in FIG. 23 was prepared to confirm that the phenomenon that was being observed by the detector was, in fact, the emission from carbon dioxide, and also to show that the signal obtained varied linearly with the amount of carbon dioxide introduced. It should be noted that the data shown in FIG. 23 indicate a linear relationship between peak height and sample volume in contrast to the results obtained in the previous study using the atomic absorption burner. It is felt that the linear relationship obtained in the present study is due to the use of the smaller flame, the smaller amounts of carbon dioxide injected, and the method of sample introduction.

Figure 24:
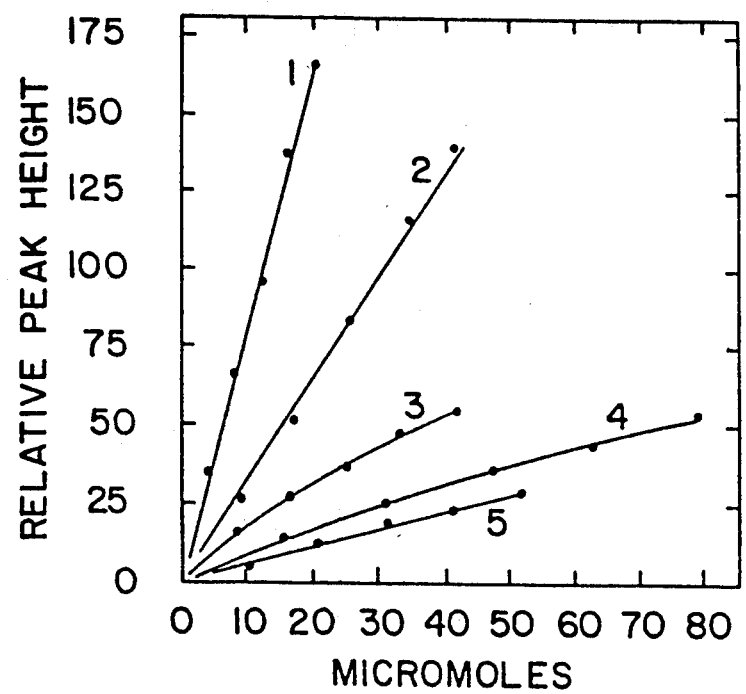
FIG. 24 graphically illustrates peak height versus micromoles of compound injected obtained with a flame infrared emission detector for 1, carbon dioxide; 2, pentane; 3, 1,1,2-trichloro-1,2,2-trifluoroethane; 4, dichloromethane; 5, carbon tetrachloride.

FIG. 24 shows five calibration curves obtained for carbon dioxide, pentane, 1,1,2-trichloro-1,2,2-trifluoroethane, dichloromethane, and carbon tetrachloride. In FIG. 24, points represent single injections; average reproducibility 2.75%. These curves were all obtained under identical conditions and are plotted in terms of moles of compound injected in order to facilitate cross comparison of detector response. While it was obvious that such compounds as hydrocarbons, aromatics, and cycloalkanes would act as a fuel in the flame, it was not clear whether halocarbons would combust sufficiently to give a signal. (Flame ionization detectors give notoriously poor response to such compounds). From FIG. 24, it can be seen that the flame infrared emission system responds well to the three halogenated compounds, although carbon dioxide produced the greatest response (i.e., largest slope). Since detector response should be proportional to the number of moles of carbon dioxide present in the flame, these curves clearly indicate that none of the organic compounds plotted in FIG. 24 are completely oxidized to carbon dioxide in the flame.

It is interesting that the calibration curve for propane (not shown) has a slope that is almost exactly 3 times that obtained for carbon dioxide, indicating essentially complete combustion in the flame. A comparison of the response obtained for the four organic compounds shown in FIG. 24 with the values expected for complete combustion (i.e., 5 times the response for carbon dioxide in the case of pentane, 2 times the response for carbon dioxide in the case of 1,1,2-trichloro-1,2,2-trifluoroethane, etc.) suggests that all four are combusted to only about 7-11%. Thus, while the flame infrared emission detector does show some compound-dependent response (like the FID), many compounds appear to be combusted to roughly the same extent. This conclusion is further supported by a preliminary study of 15 substituted n-alkanes and cycloalkanes, which produced roughly the same signal per mole of carbon.

Table III shows the reproducibility of response in terms of peak height obtained for a series of 1- $\mu$L injections of four different compounds. Each entry in the table represents the peak height obtained for a single injection. The average relative standard deviation in peak height observed for all four compounds was 2.75%.

TABLE III

| REPRODUCIBILITY OF RESPONSE FOR FOUR COMPOUNDS | | | |
|---|---|---|---|
| $CCl_2F$-$CClF_2$ | $C_5H_{12}$ | $CCl_4$ | $CH_2Cl_2$ |
| Relative Peak Height | | | |
| 50 | 64 | 31 | 49 |
| 49 | 61 | 29 | 50 |
| 51 | 58 | 30 | 49 |
| 49 | 61 | 28 | 52 |
|  |  | 29 | 48 |
|  |  | 29 |  |
| Standard Deviation | | | |
| 0.8 | 2 | 0.9 | 1 |
| Relative Standard Deviation, % | | | |
| 1.7 | 3.5 | 3.1 | 2.7 |

Figure 25:
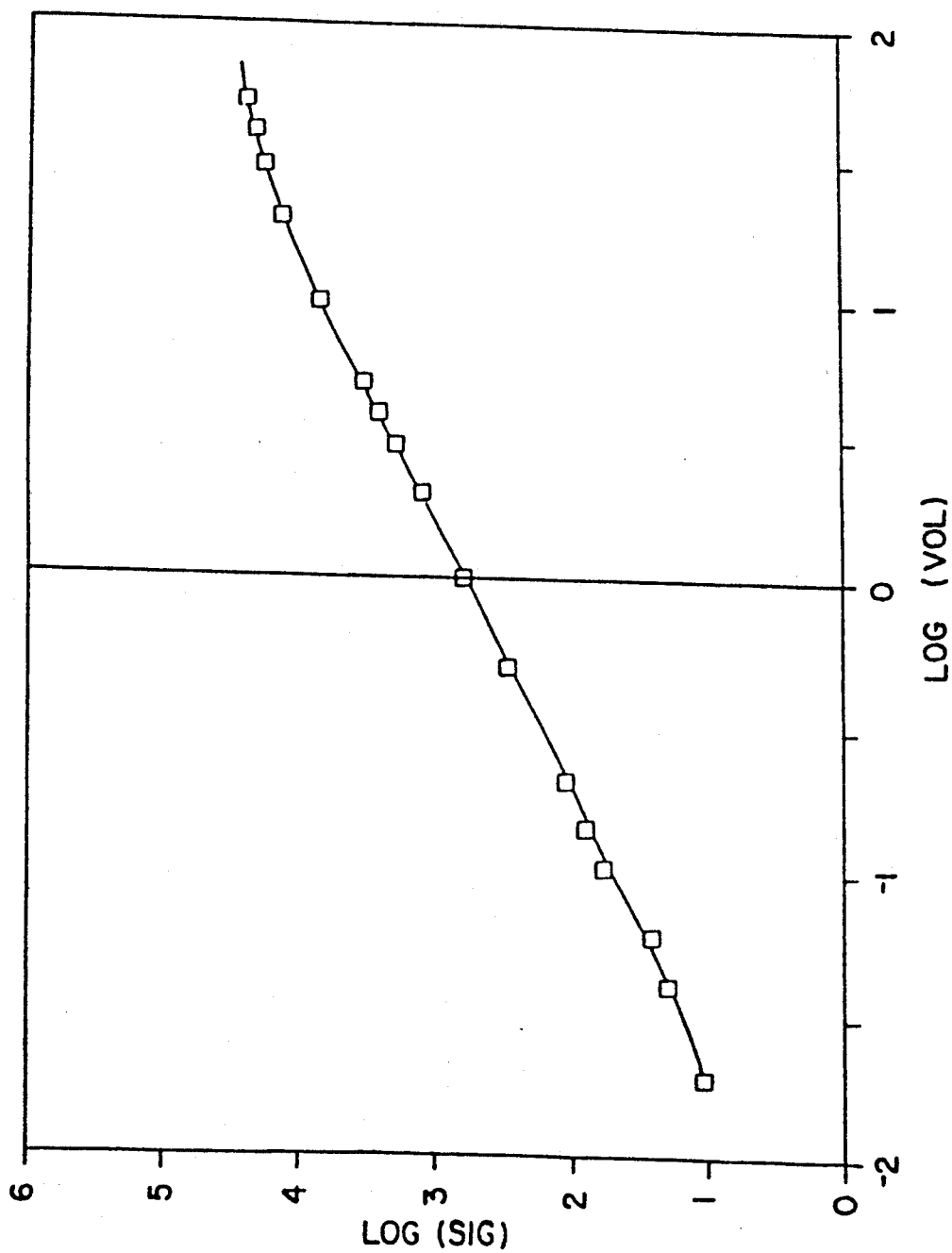
FIG. 25 graphically illustrates the logarithm of peak height versus logarithm of injection volume in microliters for pentane.

The linear dynamic range of the detection system was studied using pentane as a test compound. FIG. 25 shows a log-log plot of chromatographic peak height versus sample volume of pentane introduced into the chromatograph for sample volumes ranging from 0.02 up to 50 $\mu$L. Sample volumes greater than 0.5 $\mu$L were introduced into the chromatograph by direct injection of the neat sample. Signals corresponding to sample volumes less than 0.5 $\mu$L were obtained by injecting appropriate amounts of pentane dissolved in hexane. To obtain data over this range of sample volumes, different degrees of amplification were required which necessitated changes in the gain setting of the lock-in amplifier. The accuracy of these gain changes was checked by comparing the signal obtained for 1-$\mu$L, injections of hexane under different amplifier settings. FIG. 25 shows the response obtained from the lowest level up to injections of approximately 20- to 30-$\mu$L volume, where some downward curving takes place. This downward curving of the calibration curve could be due to several factors including the use of peak height instead of peak area as a measure of the signal, column flooding as a result of injection of large samples, and self absorption of the radiation in the flame. If the downward curving were due to self absorption, the expected slope of the log-log growth curve would be one-half. As expected, the measured slope in the linear portion of the log-log plot was one, and, while there were not a large number of data points to work with in the curving region, the slope did not appear to go to one-half. As a result, it was postulated that the signal drop off was due to column effects, a supposition which was supported by the observation of tailing in the recorder tracings of the larger peaks.

From the data presented in FIG. 25, the dynamic range of the flame infrared emission detector was estimated to be on the order of $10^4$. From this data, if the smallest volume of pentane which could be seen was taken as 0.02 μL, this would correspond to a detection limit of about $4.6 \times 10^4$ mg/s of pentane. This is actually a very conservative estimate of the detection limit because signals obtained for 0.02 μL were readily measurable above background.

To determine the effect of compound structure on the response of the detector, response data were collected for several series of compounds available in the laboratory and compatible with the GC column used. The compounds used were classified into several categories on the basis of their structure, and included substituted methanes and ethanes as well as n-alkanes and cycloalkanes. Gaseous compounds such as methane, carbon monoxide and carbon dioxide were studied by injecting 500 μL of the compound with a gas syringe. The response for various liquid compounds was obtained by injecting 1 uL of the neat liquid. For each liquid compound injected, the relative response per mole of carbon was calculated from the injection volume, the density of the liquid, the formula weight of the compound and the number of carbons in the compound.

Figure 26:
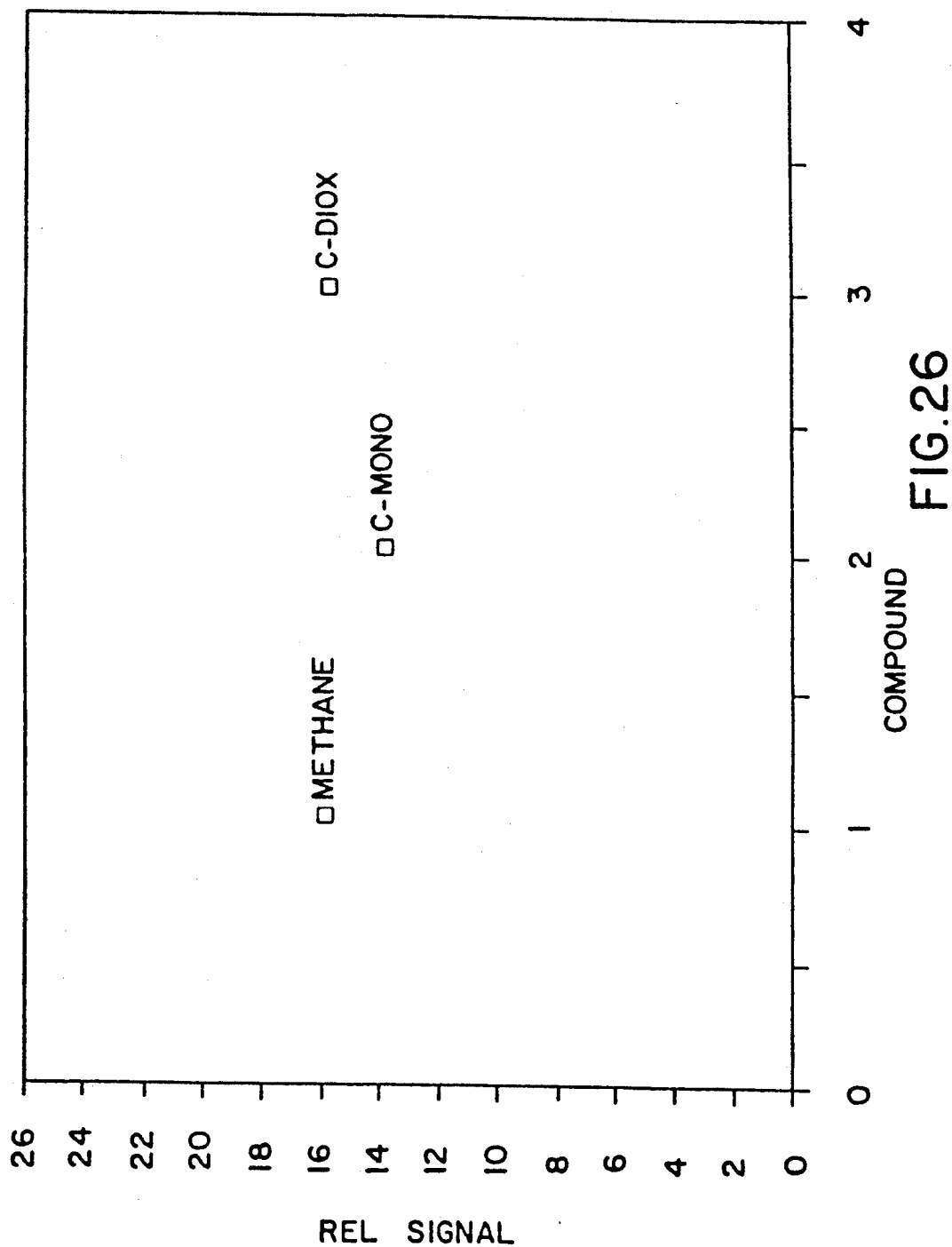
FIG. 26 graphically illustrates the relative response of a flame infrared emission detector for methane, carbon monoxide and carbon dioxide.

FIG. 26 shows the relative response obtained for equal volumes (i.e., equal moles) of one-carbon gases. If both methane and carbon monoxide were completely combusted to carbon dioxide in the flame, their response would be expected to equal that obtained for an equivalent amount of carbon dioxide. Since the data shown in FIG. 26 appear to be equal within experimental error, it suggests that the hypothesis of complete combustion for these gases is valid.

Figure 27:
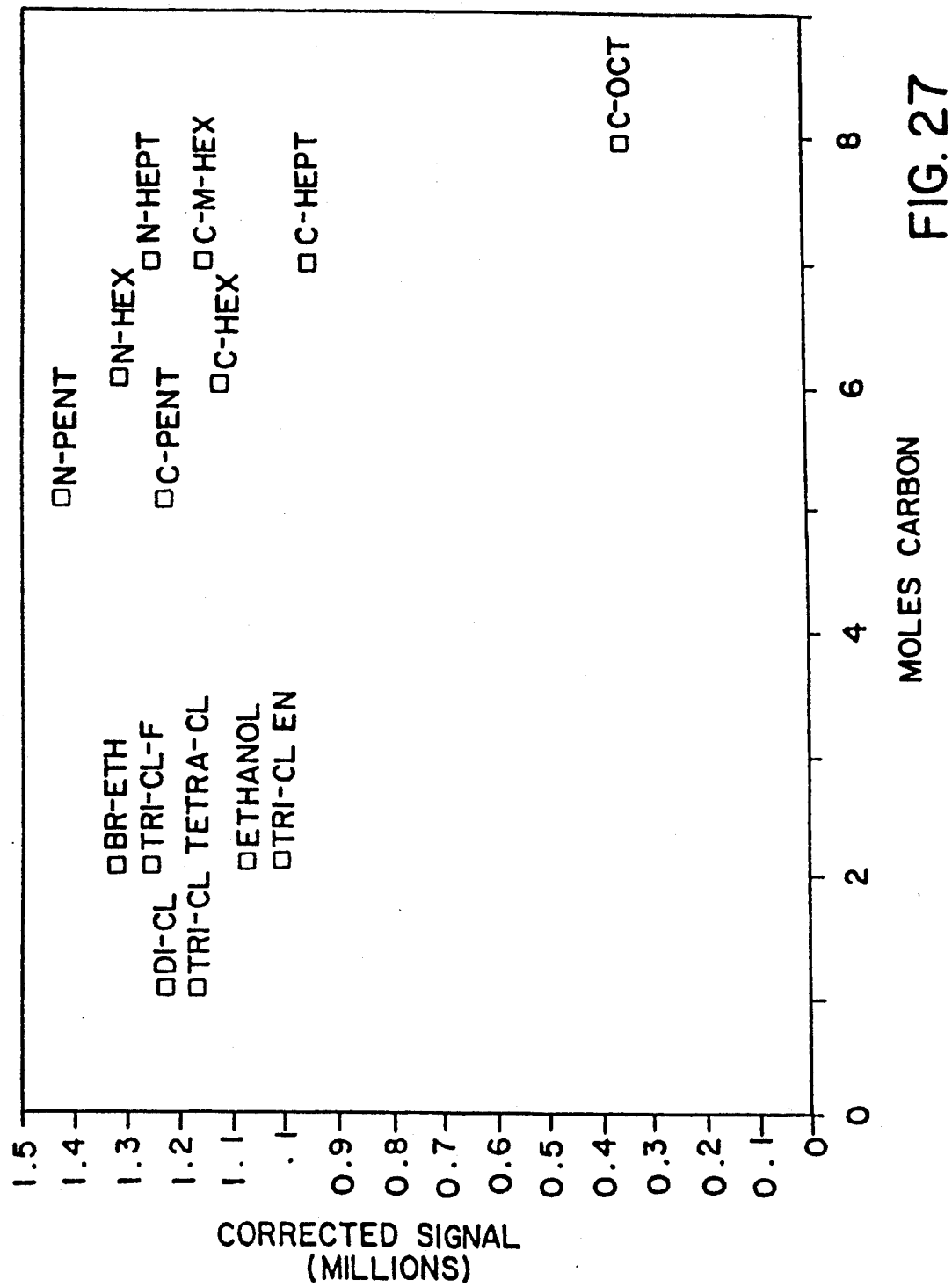
FIG. 27 graphically illustrates the relative response of a flame infrared emission detector per mole of carbon for various compounds containing different numbers of carbons: BR-ETH, bromoethanol; DI-CL, dichloromethane; TRI-CL, tricloromethane; TRI-CL EN, trichloroethanol; TETRA-CL, carbon tetrachloride; TRI-CL-F, trichlorotrifluoroethane; N-PENT, n-pentane; N-HEX, n-hexane; N-HEPT, n-heptane; C-PENT, cyclopentane; C-HEX, cyclohexane; C-HEPT, cycloheptane, C-M-HEX, methylcyclohexane; C-OCT, cyclooctane.

FIG. 27 shows the relative response obtained per mole of carbon as a function of the number of carbons present in 15 compounds. Table IV shows the actual data obtained for 1-uL, injections of the 15 compounds as well as the calculated signal per mole of carbon.

of the signal produced may not have been a reliable indication of the actual peak area. Neglecting the data for cycloheptane and cyclooctane, the average signal per mole of carbon in Table IV is $1 \times 10^6$ units which corresponds to about 50% of the signal per mole of carbon estimated for carbon dioxide. This comparison suggests that the liquid samples were not completely converted to carbon dioxide in the flame at this observation height.

The influence of carrier gas flow rate on the chromatographic peak area was studied in an effort to determine whether the detection system behaved as a concentration-dependent detector or a mass/flow rate-dependent detector. These two different detector response categories can be distinguished from one another on the basis of the effect of carrier gas flow rate on the chromatographic peak area obtained for a given sample size. In the case of the concentration-dependent detector, the chromatographic peak area will vary inversely with carrier gas flow rate, whereas with a mass/flow rate detector the chromatographic peak area will be independent of carrier gas flow rate (McNair, H. M., Bonelli, E. J., *Basic Gas Chromatography*, 5th ed., Varian Instrument Division, Palo Alto, Calif., 1969, pp. 81-5.).

Figure 28:
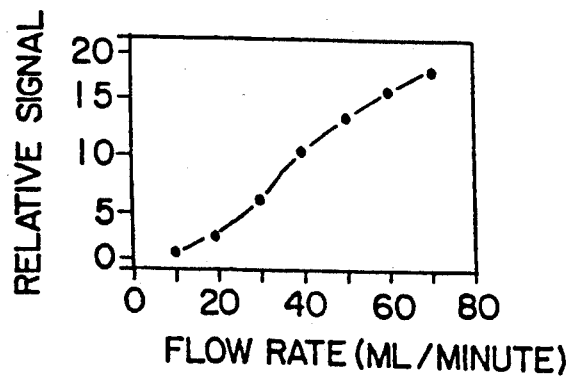
FIG. 28 graphically illustrates peak height for carbon dioxide versus carrier gas flow rate obtained with a flame infrared emission detector.
Figure 29:
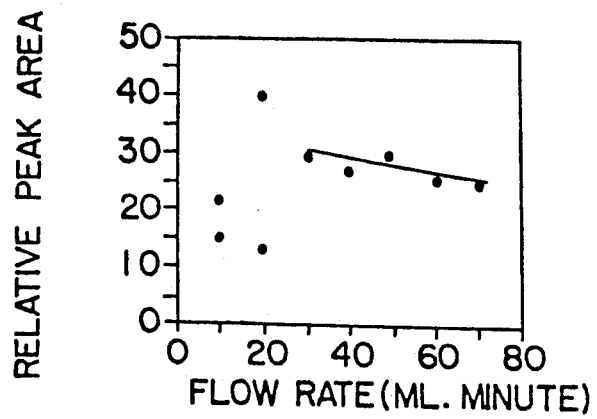
FIG. 29 graphically illustrates peak area versus carrier gas flow rate obtained with a flame infrared emission detector.

FIGS. 28 and 29 show the effect of carrier gas flow rate on chromatographic peak height and peak area for a series of 0.500 mL injections (22.3 μmol at STP) of carbon dioxide. Each point represents a single injection of carbon dioxide; reproducibility is about 2.8%. Because the flame infrared emission detector consumes the sample in the process of producing a signal, the system is expected to behave in a mass-flow rate manner similar to the FID (flame ionization detector). In the case of the flame infrared emission detector, the signal will be proportional to the instantaneous concentration of carbon dioxide present in the flame. The net amount of carbon

TABLE IV

| | Relative Response per Mole of Carbon for Compounds Studied | | | | |
|---|---|---|---|---|---|
| Compound | Peak Height | F.W. | Density | Carbons/mole of compound | Signal/mole C |
| Cyclopentane | 65 | 70.13 | 0.745 | 5 | $1.22 \times 10^6$ |
| Cyclohexane | 62 | 84.16 | 0.779 | 6 | $1.12 \times 10^6$ |
| Cycloheptane | 55 | 98.18 | 0.810 | 7 | $9.52 \times 10^5$ |
| Cyclooctane | 20 | 112.21 | 0.839 | 8 | $3.34 \times 10^5$ |
| Methylcyclohexane | 63 | 98.18 | 0.769 | 7 | $1.15 \times 10^6$ |
| Dichloromethane | 19.3 | 84.94 | 1.336 | 1 | $1.23 \times 10^6$ |
| Trichloromethane | 14.5 | 119.39 | 1.489 | 1 | $1.16 \times 10^6$ |
| Tetrachloromethane | 12.1 | 153.84 | 1.594 | 1 | $1.17 \times 10^6$ |
| n-Pentane | 61.5 | 72.13 | 0.626 | 5 | $1.42 \times 10^6$ |
| n-Hexane | 60 | 86.17 | 0.659 | 6 | $1.31 \times 10^6$ |
| n-Heptane | 60 | 100.2 | 0.684 | 7 | $1.26 \times 10^6$ |
| Ethanol | 37.9 | 46.07 | 0.789 | 2 | $1.11 \times 10^6$ |
| Bromoethanol | 35.5 | 108.94 | 1.46 | 2 | $1.32 \times 10^6$ |
| Trichlorotrifluoroethane | 21.1 | 187.39 | 1.573 | 2 | $1.26 \times 10^6$ |
| Trichloroethanol | 24 | 131.4 | 1.466 | 2 | $1.08 \times 10^6$ |

With the exception of cycloheptane and cyclooctane, FIG. 27 shows that roughly the same relative response was obtained regardless of the number of carbons in the compound out to carbon numbers of about seven. This suggests that, if not completely combusted to carbon dioxide, all of the compounds studied with the exception of the two mentioned above are combusted to about the same extent with very little influence of carbon number or compound structure. The exceptions to this rule obtained for cycloheptane and cyclooctane may be more apparent than real because the peak shapes obtained for these compounds were not symmetric. As a result, the use of peak height as a quantitative measure dioxide present in the flame at any instant will depend on the difference between the rate at which sample is introduced into the flame (and converted into carbon dioxide by combustion) and the rate at which combustion products are removed from the observation zone by transport of flame gases. For a given set of fuel and oxidant flow rates, the rate of removal of combustion products from the observation zones should be fixed. Therefore, the mass-flow rate detector model predicts that peak signal will increase directly with carrier gas flow rate and the integrated peak area will be independent of carrier gas flow rate.

FIG. 28 shows that peak height does indeed increase with carrier gas flow rate, although the relationship is not strictly linear. FIG. 29 shows that for carrier gas flow rates above 30 mL min$^{-1}$, chromatographic peak area varies only slightly with increasing carrier gas flow rate. Apparent deviations from mass-flow rate behavior can be attributed to flame cooling, incomplete mixing, and dilution As the carrier gas flow rate increases, introduction of increasing amounts of helium into the flame will lead to a small decrease in flame temperature as well as a dilution of flame gases. Both of these factors will contribute to a reduction in detector response. In addition, sample mixing with flame gases may become less complete at higher flow rates, leading to incomplete combustion.

At very low carrier gas flow rates (less that 30 mL min$^{-1}$), the reproducibility in peak area measurements degrades severely (FIG. 29) while chromatographic peak height tends to approach a limiting value. Under these low flow rate conditions, sample removal is the dominant process so the net amount of carbon dioxide present in the flame at any instant is small, resulting in a small signal. In addition, low carrier gas flow rates imply a longer retention time and a correspondingly wider peak bandwidth. As the peak bandwidth increases, the concentration of sample introduced into the flame at any given instant decreases. Since a minimum concentration of carbon dioxide is required to produce a measurable signal with the flame infrared emission detector, reducing the carrier gas flow rate, while favoring increased sample mixing and combustion, will eventually lead to $CO_2$ levels in the flame below the limit of detectability. At these flow rates, both response and reproducibility should decrease in the manner observed.

Before reporting the detection limit obtained for pentane by using the flame infrared emission detector, it is worthwhile to discuss how detection limits are determined from chromatographic measurements. Because the flame infrared emission detector responds in a mass flow manner, the detection limit will depend on the limiting base-line noise and the response of the detector. The response, R, of the detector is determined from the slope of the calibration curve obtained by plotting signal, S, versus mass flow rate, $M_f$, into the detector.

$$R = \Delta S / \Delta M_f \quad (1)$$

Mass flow rate, expressed as mg s$^{-1}$, is determined by dividing the total mass of injected sample (mg) by the bandwidth (seconds) of the resulting chromatographic peak. If the calibration curve obtained by plotting signal versus mass flow rate into the detector (i.e., $S = RM_f$) is extrapolated back to smaller mass flow rate values, a point will be reached where the signal can no longer be distinguished from the base-line noise of the chromatogram. If this point is taken as a signal equal to twice the root-mean-square (rms) base-line noise, the detection limit will be given by $$S = RM_f = 2(\text{rms base-line noise}) \quad (2)$$

Solving eq 2 for $M_f$ gives $$(M_f)_{dl} = 2(\text{rms base-line noise})/R \quad (3)$$

where $(M_t)_{dl}$ is the minimum detectable mass flow rate into the detector in mg s$^{-1}$.

To compare the performance of a mass flow rate detector like flame infrared emission with a concentration-dependent detector like the thermal conductivity detector (TCD), the minimum detectable mass flow rate is divided by the carrier gas flow rate to give $$C_{dl}(\text{mg mL}^{-1}) = 2(\text{rms base-line noise})/RF \quad (4)$$

where F is the carrier gas flow rate in mL s$^{-1}$ and $C_{dl}$ is the lowest concentration that the detector can sense. Since the rms base-line noise observed is dependent on the amplifier time constant, it is important to specify the time constant of the system when reporting the detection limit.

With eq 3, the detection limit for pentane was determined from detector response measurements and estimates of the rms base-line noise to be $4.6 \times 10^{-4}$ mg s$^{-1}$ for an amplifier time constant of 3 s. The rms noise was estimated as one-fifth of the peak-to-peak base-line noise. In terms of concentration of sample entering the detector for a 40 mL min$^{-1}$ carrier gas flow rate, the minimum detectable concentration of pentane was determined from eq 4 to be $7 \times 10^{-4}$ mg mL$^{-1}$ or $1 \times 10^{-8}$ mol cm$^{-3}$ of pentane. Assuming standard temperature and pressure, the concentration of pentane reported above corresponds to 224 ppm on a volume basis.

By comparison, detection limits for similar compounds obtained with a flame ionization detector (FID) are on the order of $10^{-11}$ mg s$^{-1}$ and for a thermal conductivity detector (TCD), the detection limit is typically considered to be on the order of $10^{-6}$–$10^{-7}$ mol cm$^{-3}$ (Karger, B. L. et al *An Introduction to Separation Science*, Wiley, New York 1973 pp. 232-236) depending on operating conditions. From the above discussion, it can be seen that the flame infrared emission detector is as sensitive as a TCD, but considerably less sensitive than an FID. Therefore, it is clear that significant increases in sensitivity will be required before the flame infrared emission detector is competitive with the FID. Nevertheless, the detector described in Experiment 2 is only a prototype, and significant improvements in sensitivity can be expected as the detection system is refined and limiting noise sources are identified.

Figure 30:
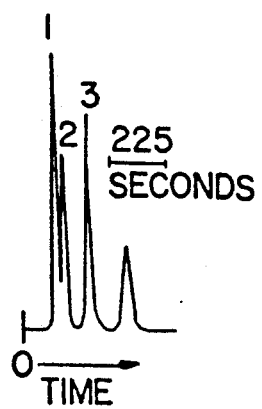
FIG. 30 shows the chromatogram obtained isothermally at 50° C. on an Apiezon-L column for a 5- $\mu L$ injection of a 1:2:1:3 volume mixture: pentane (1); 1,1,2-trichloro-1,2,2-trifluoroethane (2); hexane (3); carbon tetrachloride (4).

FIG. 30 shows the performance of the flame infrared emission system under isothermal conditions for a synthetic sample consisting of a 1:2:1:3 volume mixture of pentane, 1,1,2-trichloro-1,2,2-trifluoroethane, hexane, and carbon tetrachloride. This chromatogram was obtained from a 5-$\mu$L injection of this mixture with an Apiezon L column maintained at 50° C. Since the PbSe detector can respond to intensity variations in the kilohertz range, the flame infrared emission detector has no difficulty in following the relatively slow intensity variations produced during elution of components from the gas chromatograph.

The flame infrared emission detection system has been shown to be a relatively simple, inexpensive detector for gas chromatography. Compared with other detection systems currently employed, the use of infrared emission has a number of advantages. Since the system is not based on thermal conductivity, nitrogen or hydrogen can be used as a carrier gas in place of the more expensive helium required with a thermal conductivity detector. The system described in this application has been shown to exhibit a wide dynamic range characteristic of emission measurements. The detector has a relatively fast response time which is a potential asset in being able to detect narrow chromatographic peaks as might be obtained with capillary column gas chromatography.

Although the analytical applications of infrared emission described above centered on the measurement of the infrared emission from carbon dioxide, other combustion products such as oxides of nitrogen and sulfur should produce infrared emission at other wavelengths. Thus, a detection system having several detector/filter combinations could be produced which would respond not only to the presence of carbon but to nitrogen and sulfur as well.

The detection systems described above appear to respond to carbon dioxide produced by the combustion of compounds introduced into the flame, and do not appear to be greatly affected by the structural nature of the samples. They also respond to certain gases such as carbon monoxide and carbon dioxide which do not respond well with the flame ionization detector.

EXPERIMENT 3

The miniature capillary-head burner of Experiment 2 was modified for use with liquid samples. As the previously designed burner was intended to admit a gas stream from the gas chromatograph to the center of the burner-head, the burner was modified for nebulized liquid samples. The central sample injection capillary was removed, and the number of small-bore capillary tubes in the burner-head was increased from 6 to 19 (the internal diameter of the capillary tubes was 0.6 mm). The overall diameter of the burner orifice was 0.5 cm. The capillary-head burner was fitted with a Jarrell-Ash model X-88 atomic absorption cross-flow nebulizer and a 3 cm long×4 cm diameter teflon spray chamber. The nebulizer and spray chamber were coupled to the burner body by boring a one inch hole in the side of the burner body (perpendicular to the capillary-head) and press fitting the spray chamber/nebulizer assembly to the burner.

A 1:1 hydrogen/air flame stoichiometry was used for all measurements, and the fuel and oxidant flow-rate were maintained at 200 mL/min. A 1:1 fuel/oxidant mixture resulted in a stable flame approximately 4 cm in height by 1 cm in width. The infrared emissions were observed over a 0.6 cm vertical segment centered at a height of 1.5 cm from the burner top. The reagent grade liquid samples were introduced into the flame via aspiration by the nebulizer.

All flame infrared emission spectra were acquired on an unpurged Mattson Cygnus 100 Fourier transform spectrometer. Fourier transform infrared emission spectroscopy allows multiwavelength analysis. The Fourier transform spectrometer, by virtue of the multiplex nature of the data acquisition, is a multichannel instrument and can therefore monitor all infrared wavelengths simultaneously. Since the desired molecular emission occurs in the infrared spectral region, any standard, commercially available Fourier transform-spectrometer can be utilized without the need for special optics, beamsplitters, or detectors. The Fourier transform instrument also provides several advantages for infrared emission spectroscopy. These advantages include: a single instrument for both elemental and molecular analysis, high optical throughput, good spectral resolution, accurate wavelength recording due to the reference laser, the ability to signal average by coaddition, and the capability of performing spectral subtraction.

Figure 31:
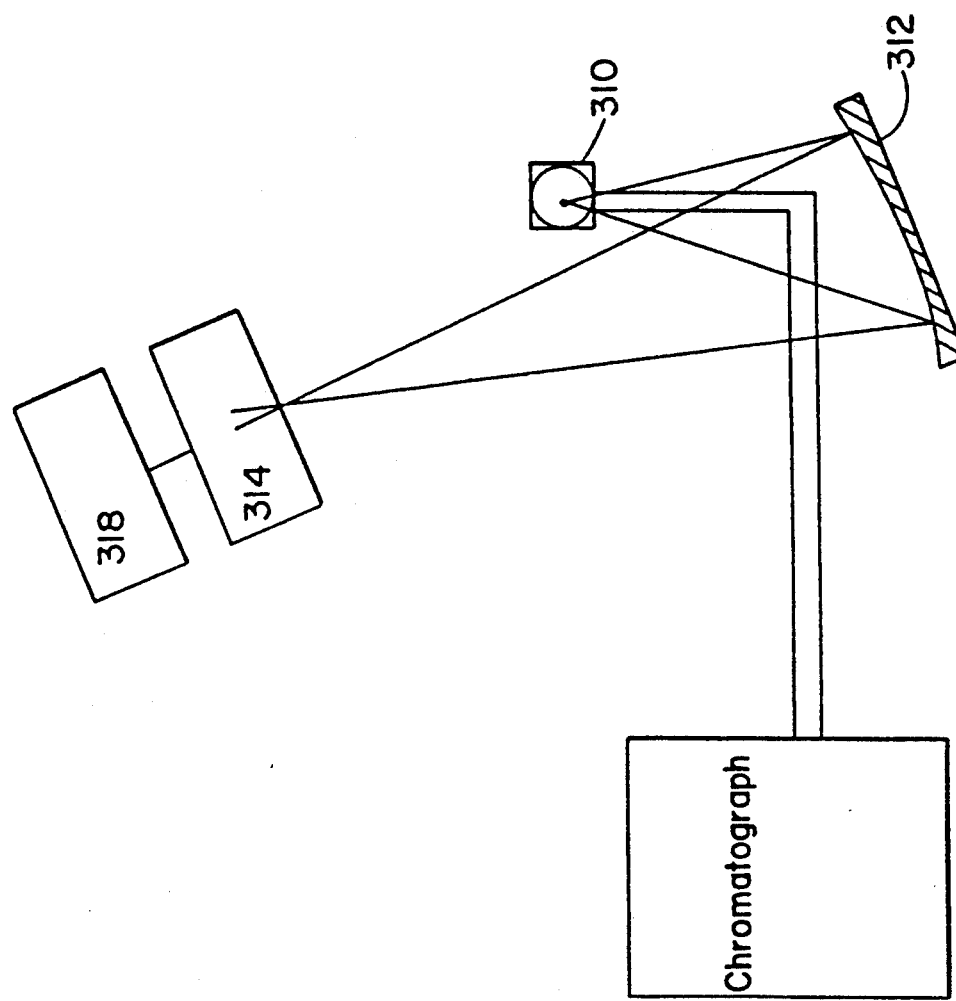
FIG. 31 schematically illustrates the experimental set up of the burner, mirror and Fourier transform spectrometer for Experiment 3.
Figure 32:
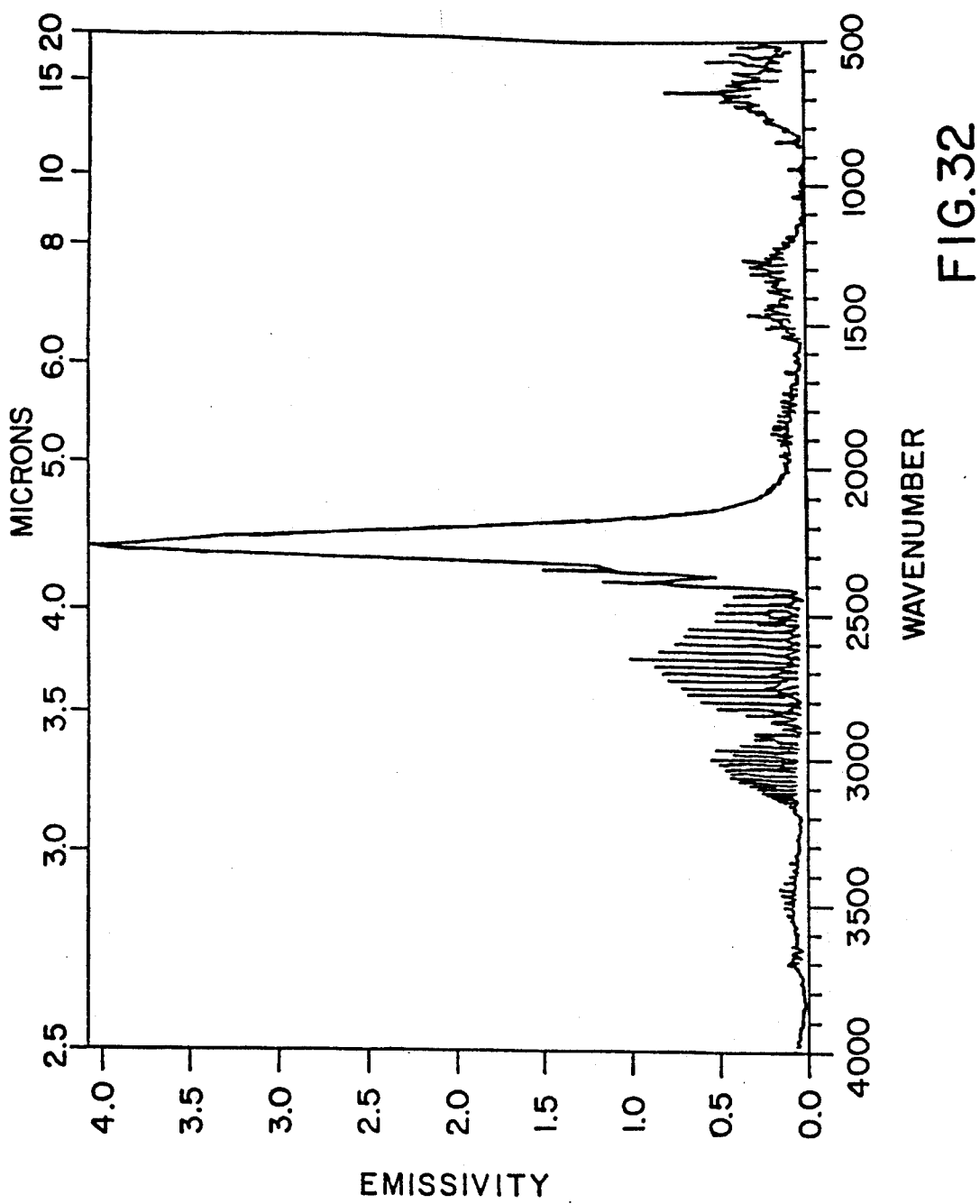
FIG. 32 is a flame infrared emission spectrum of carbon tetrachloride.
Figure 33:
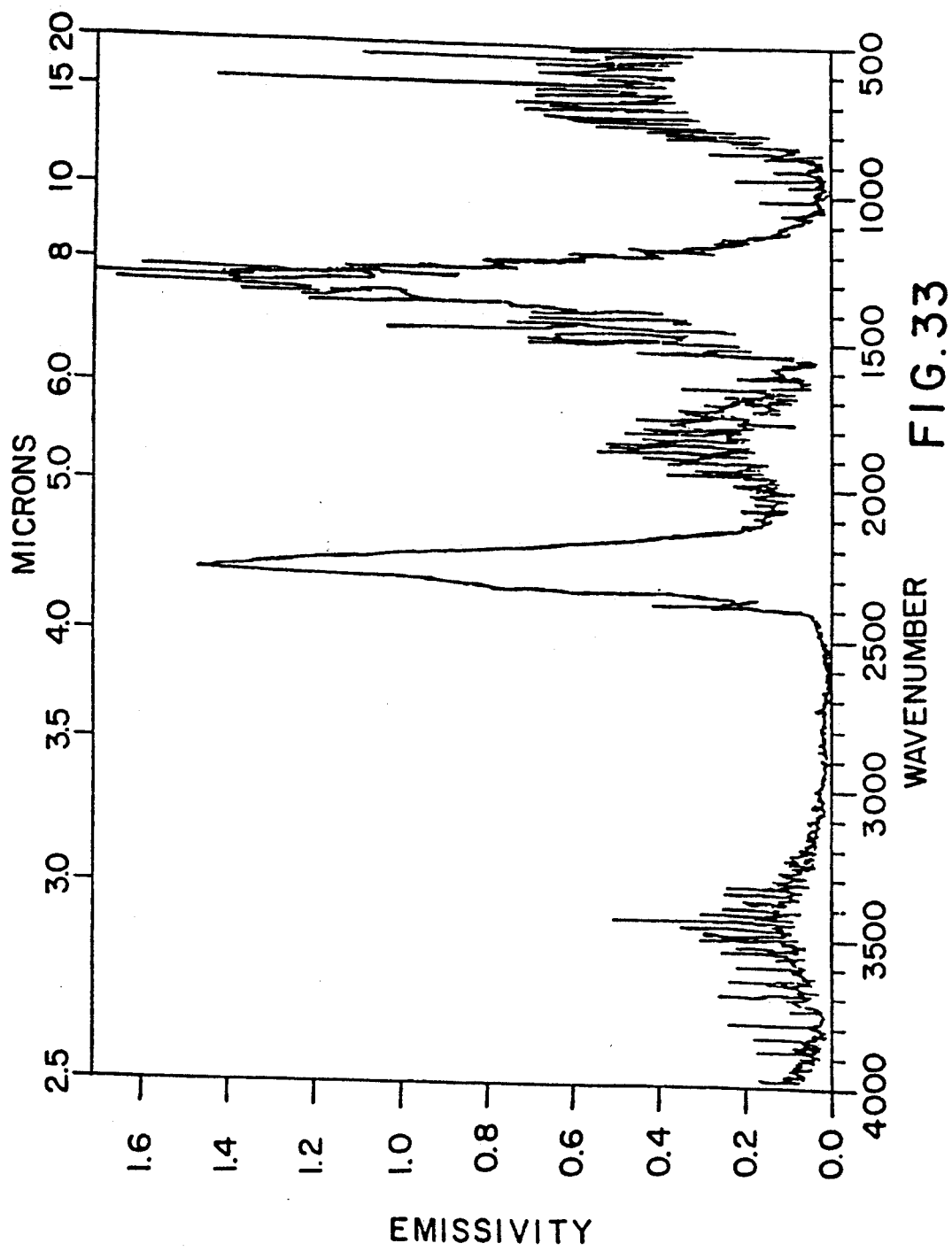
FIG. 33 is a flame infrared emission spectrum of methanesulfonyl fluoride.
Figure 34:
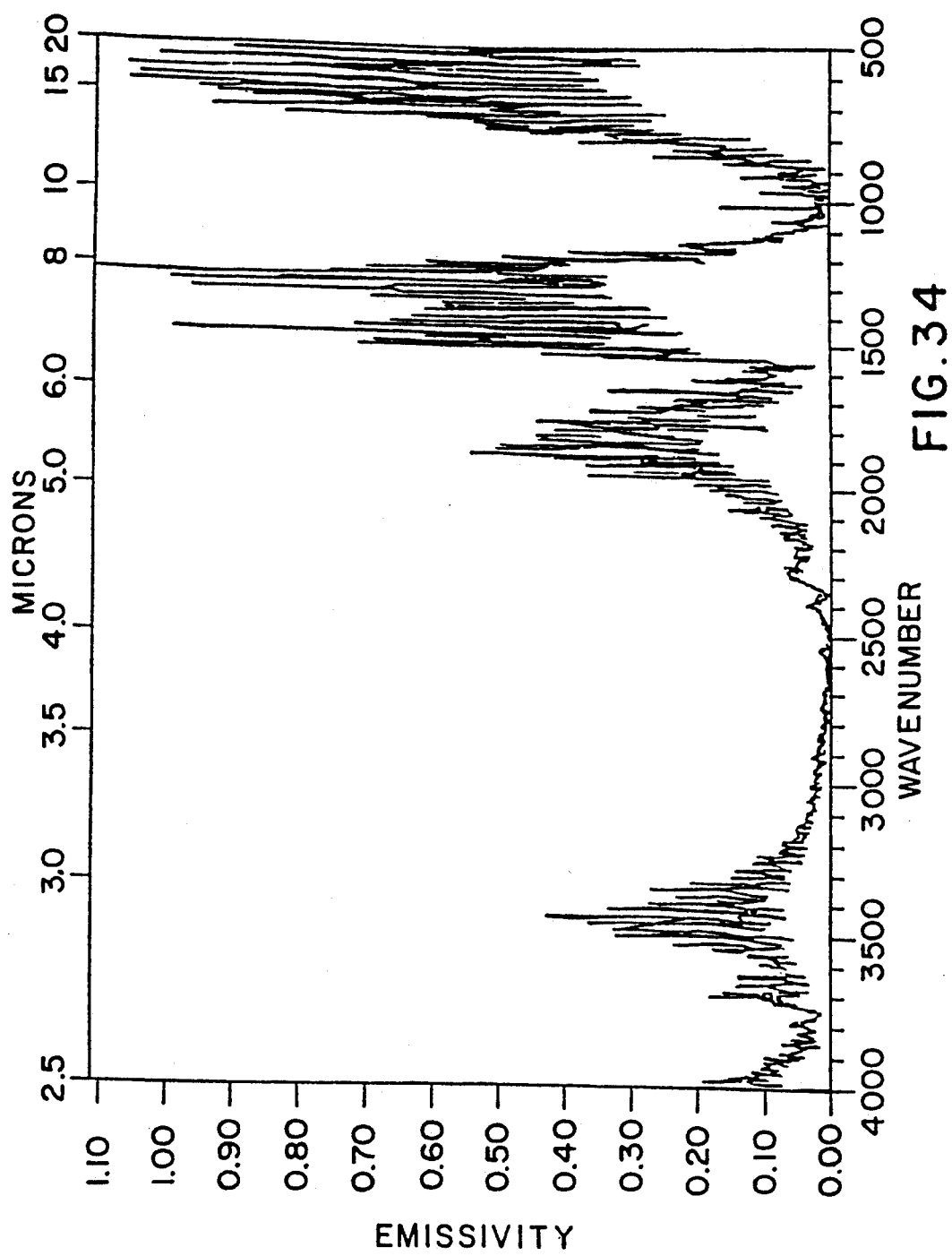
FIG. 34 is a flame infrared emission spectrum of the $H_2$/air background at high gain.
Figure 35:
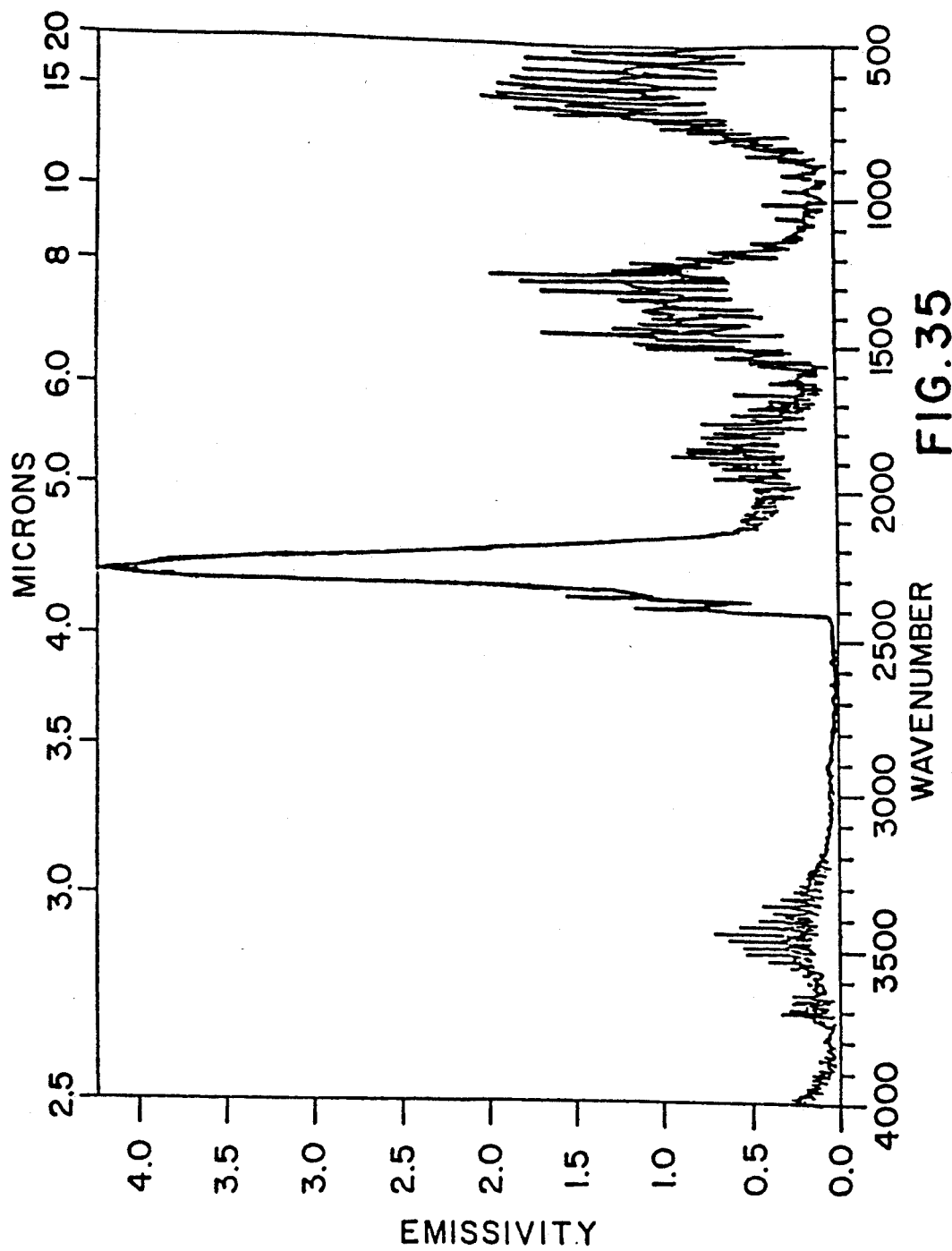
FIG. 35 is a flame infrared emission spectrum of methanol.
Figure 36:
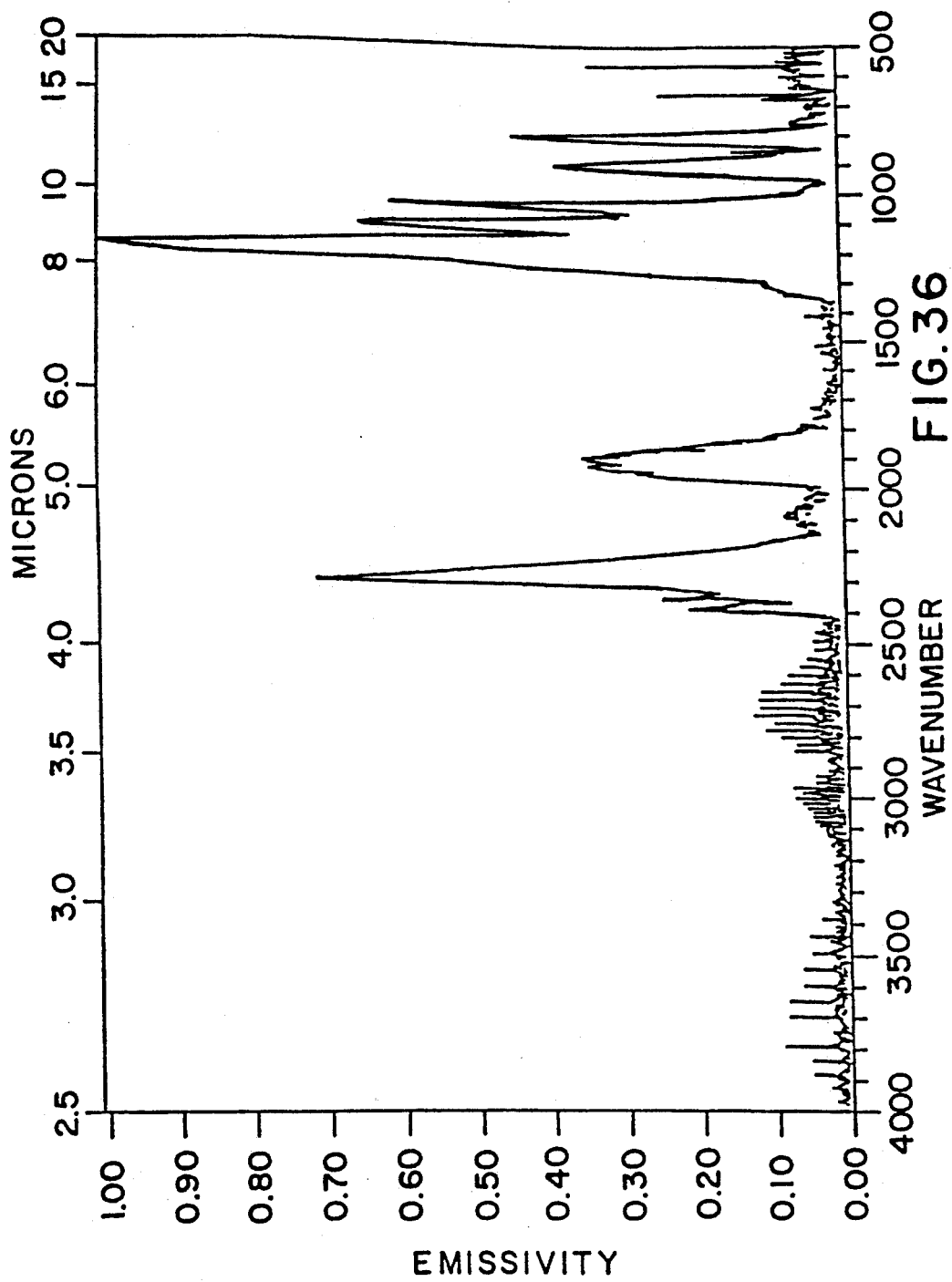
FIG. 36 is a flame infrared emission spectrum of trichlorotrifluoroethane.
Figure 37:
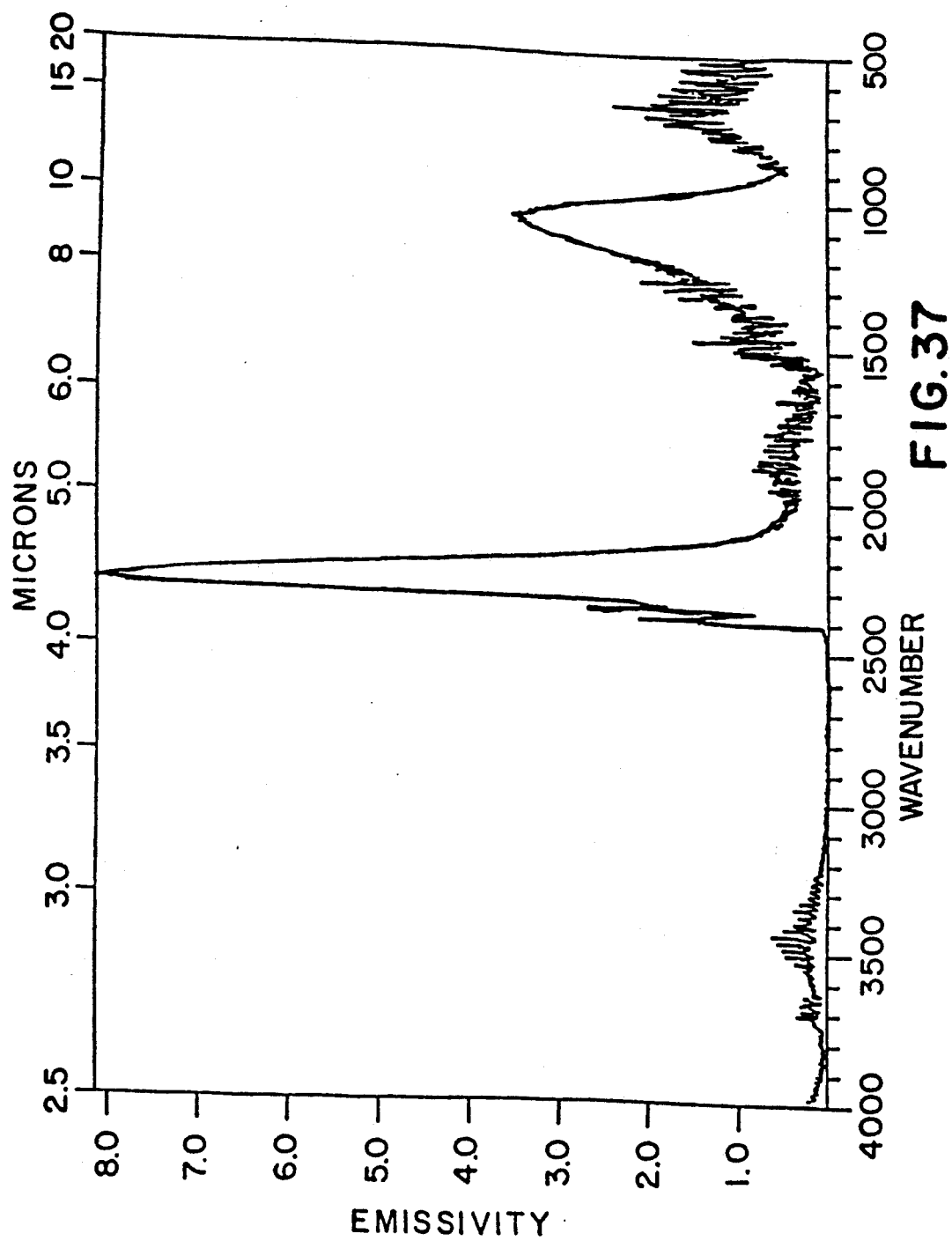
FIG. 37 is a flame infrared emission spectrum of tetramethylsilane.

FIG. 31 schematically shows the arrangement of the burner 310, mirror 312 and Fourier transform-spectrometer 314 for Experiment 3. A 5-cm-focal-length, 10-cm-diameter aluminum mirror 312 was used to collect and collimate the infrared emissions from the flame. It should be noted that the infrared collection mirror 312 was placed off the optical axis by approximately 30 degrees. No significant abberational defects were observed.

A room temperature, triglycine sulfate (TGS) detector ($D^* = 2 \times 10^9$ cm $H^{\frac{1}{2}}$ $W^{-1}$) and KBr beamsplitter were employed in the Fourier transform- spectrometer 314. All spectra were acquired with 4 cm$^{-1}$ resolution at a mirror velocity of 0.32 cm/s. A triangular apodization function was used with 1× zero filling and, due to the discrete line nature of the emission spectra, phase correction was not applied. Instead, the single-beam power spectra were calculated and plotted, and none of the spectra in FIGS. 32-37 have been corrected for instrumental response The hydrogen/air flame was chosen to excite the molecules of interest in order to eliminate carbon dioxide emissions from the fuel gases. Otherwise, the determination of carbon, as carbon dioxide, would be significantly impaired.

FIGS. 32-37 are characteristic infrared emission spectra for carbon tetrachloride, methanesulfonyl fluoride, the $H_2$/Air flame background, methanol, trichlorotrifluoroethane and tetramethylsilane. These spectra clearly show that bands other than those from $H_2O$ and $CO_2$ can be observed in the flame.

EXPERIMENT 4

Figure 38:
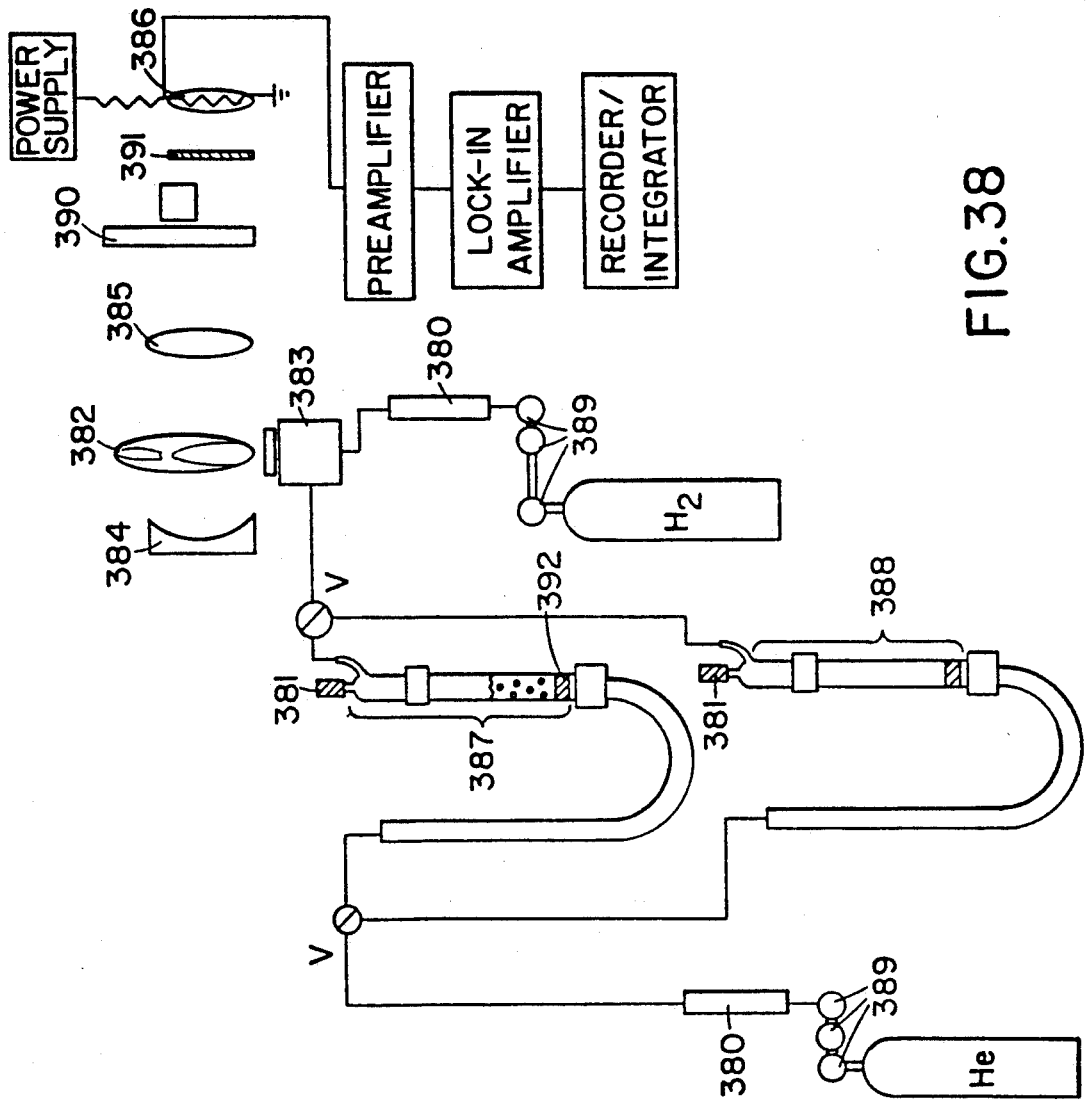
FIG. 38 schematically illustrates the experimental set up for Experiment 4 for the determination of chloride and available chlorine in aqueous samples.

The chlorine sensitive flame infrared emission detection instrument is shown in FIG. 38. The instrument consists of a chlorine generation and liberating apparatus and a flame infrared emission detection system. The chlorine generation and liberating apparatus contains two purge devices 387 and 388 (model #991710, Wheaton Scientific, Millville, N.J.) connected together in parallel using 3.2 mm o.d. polyethylene tubing and two, three-way valves (model #B-42XS4, Whitey Co., Highland Heights, Ohio) as described in Kubala et al., *Anal. Chem.*, 1989, Vol. 61 pgs. 1841-1846, incorporated herein by reference. One of the purge tubes serves as the sample chamber 387 while the second serves as the reference chamber 388.

Each purge device consists of a 5-mL demountable tube that can be disconnected for sample introduction and cleaning. A septum 381 located at the top of each purge tube allows the samples and reagents to be introduced by syringe (sulfuric acid syringe: model #2300, Becton-Dickson & Co., Rutherford, N.J.; KMnO₄ syringe model #1001, Hamilton Co., Reno, Nev.; water sample syringe: model #1002, Hamilton Co., Reno, Nev.).

Helium gas, maintained at a flow rate of 130 mL/min, was used to purge evolved $Cl_2$ from the aqueous solutions into the flame 382 of the flame infrared emission detector. The optimum flow rate of hydrogen in the capillary-head burner 383 was determined to be 324 mL/min with combustion supported only by entrained air. The supply pressures of the helium and hydrogen were regulated at 0.75 atm using triple-stage regulation 389.

The optical system of the flame infrared emission detector was modified from that described in Kubala, et al., Anal. Chem., 1989, Vol. 61, pgs. 1841-1846 by the addition of a 5-cm-focal-length, f/1 concave mirror 384 (Model #44340, Oriel Corp., Stratford, Conn.) installed behind the hydrogen/air flame. This back collection mirror 384, in conjunction with the $CaF_2$ lens 385, directed the infrared emission from the flame onto the PbSe detector 386.

In addition to the installation of the back collection mirror 384, the flame infrared emission detector was also modified by replacing the 4.4 $\mu$m $CO_2$ optical bandpass filter desribed in Kubala, et al., *Anal. Chem.*, 1989, Vol. 61, pgs. 1841–1846, with a 3.8 $\mu$m optical bandpass filter 391 (Model #S-902-079, Spectrogon, Secaucus, N.J.) to spectrally isolate a portion of the HCl emission consisting of most of the more intense part of the R branch. This optical bandpass filter 391 possessed a full-width at half-maximum height (FWHM) of 0.18 $\mu$m and was placed immediately in front of the detector 386.

The flame infrared emission was detected using a PbSe photoconductive cell operated at room temperature with a bias potential of 45 V. The detector preamplifier circuit, lock-in amplifier and recorder/integrator have been previously discussed in Kubula, et al., *Anal. Chem.*, 1989, Vol. 61, pgs. 1841–1846 and except for a slight change in the preamplifier circuit to allow for a larger bias voltage.

All chemicals were A.C.S. reagent grade and were used without further purification. A stock solution of 100 mM NaCl (Mallinckrodt, Inc., St. Louis, Mo.) was prepared by dissolving NaCl, dried at 120° C. for 24 hours, in deionized water. Standard NaCl solutions, having concentrations of 0.1, 0.5, 1.0, 2.0, 5.0, 8.0, and 10 mM, were prepared before use by diluting aliquots of the stock solution to the appropriate volumes.

A saturated solution of $KMnO_4$ (Mallinckrodt, Inc., St. Louis, Mo.) used in conjunction with concentrated $H_2SO_4$ (Mallinckrodt, Inc., St. Louis, Mo.) served as the oxidizing agent for the aqueous chloride determinations. The saturated $KMnO_4$ solution was boiled and filtered to remove any $MnO_2$ that might be present. Aqueous solutions of $AgNO_3$ (Thorn Smith, Inc., Beulah, Mich.) and $Na_2S_2O_3$ (Sargent-Welch Scientific Co., Skokie, Ill.) were used in the titrimetric analysis of aqueous chloride and available chlorine, respectively.

Prior to use, the flame in the flame infrared emission system was ignited, and the instrument was allowed to warm up until a stable baseline was obtained on the chart recorder. As part of the warm-up procedure, He purge gas was directed through the dry reference purge tube and into the flame. When the instrument had stabilized, the analysis for aqueous chloride or available chlorine was carried out according to the appropriate procedure indicated below.

Aqueous Chloride

To construct a calibration curve for chloride using the flame infrared emission system, the sample purge tube 387 was disconnected, a 1.0-ml volume of an aqueous chloride standard was placed on the glass frit 392, and a 0.5-mL volume of concentrated $H_2SO_4$ was added using a syringe. The purge assembly was then reconnected, and the He flow was switched from the reference purge tube 388 to the sample purge tube 387 using the dual, three-way valve system. The acidified standard solution was purged for approximately 70 seconds. A 0.1-mL aliquot of the saturated $KMnO_4$ solution was injected through the septum 381 and into the sample chamber using a syringe. The chlorine gas produced from the resulting oxidation of the aqueous chloride in the sample was liberated from the solution and introduced into the flame where it formed vibrationally excited HCl.

After the resulting HCl infrared emission peak had been recorded, the He flow was switched back through the reference purge device. The sample purge tube 387 was then disconnected and rinsed thoroughly with deionized water to remove excess reagents. This process was repeated for all chloride standards to construct a calibration curve of peak instensity versus chloride concentration.

Several natural water samples were collected from sources around the Waco area and stored according to standard procedures. One-mL volumes of these natural water samples were treated using the same procedure as outlined for the preparation of the chloride calibration curve, and the resulting infrared emission signal was recorded. Aqueous chloride concentrations in these natural water samples were read from the calibration curve using measured peak heights. For comparison purposes, aqueous chloride in these samples was also determined by argentometric titration using 0.0136N $AgNO_3$ with potassium chromate as an indicator according to procedures outlined in *Standard Methods for the Examination of Water and Wastewater*, (16th ed.; Greenberg, A. E.; Trussell, R. R.; Clesceri, L. S.; Franson, M. A. H.; Eds.; American Public Health Association: Washington, DC 1985; pp. 287–294).

Available Chlorine

Calibration curves for available chlorine ($Cl_2$, HOCl and $OCl^-$) was constructed using aqueous chloride standards as described previously. Bleach sample concentrations were read as chloride concentrations from the chloride calibration curve and converted into available $Cl_2$ concentration using the relationship, $\frac{1}{2}[Cl^-]=[Cl_2]$.

To determine available chlorine in bleach using the flame infrared emission system, a 0.5-mL aliquot of concentrated $H_2SO_4$ and a 1.0-mL volume of deionized water were added to the disconnected sample purge tube 387 as described for the aqueous chloride determinations. The sample purge device 387 was then reconnected and the He purge gas flow switched from the reference purge device to the sample purge device. After purging this acidified deionized water solution for approximately 70 seconds, a 0.1-mL aliquot of a bleach sample, diluted by a factor of 20 with deionized water, was introduced through the septum using a syringe. The $Cl_2$ gas generated from the acidification of the bleach sample was purged from the solution into the flame 382 where it formed vibrationally excited HCl. After the HCl infrared emission peak had been recorded, sample clean-up was performed as described previously.

Three commercially available bleach solutions were selected for the determination of available chlorine. For comparsion purposes, available chlorine in these samples was also determined by iodometric titration using 0.151N $Na_2S_2O_3$ according to the procedure outlined in Standard Methods as referenced above.

The flame infrared emission detection system used in this experiment for the determination of chloride and available chlorine is similar to the system which has been previously described for use in total inorganic carbon (TIC) determinations in Kubala et al., *Anal. Chem.*, 1989, Vol. 61, pgs. 1841–1846.

However, since the HCl infrared emission band occurs in the 3.16–4.24 μm spectral region of the hydrogen flame (FIG. 39B), the 4.4 μm optical bandpass filter used to isolate the $CO_2$ emission was replaced with a 3.8 μm bandpass filter.

Figure 39:
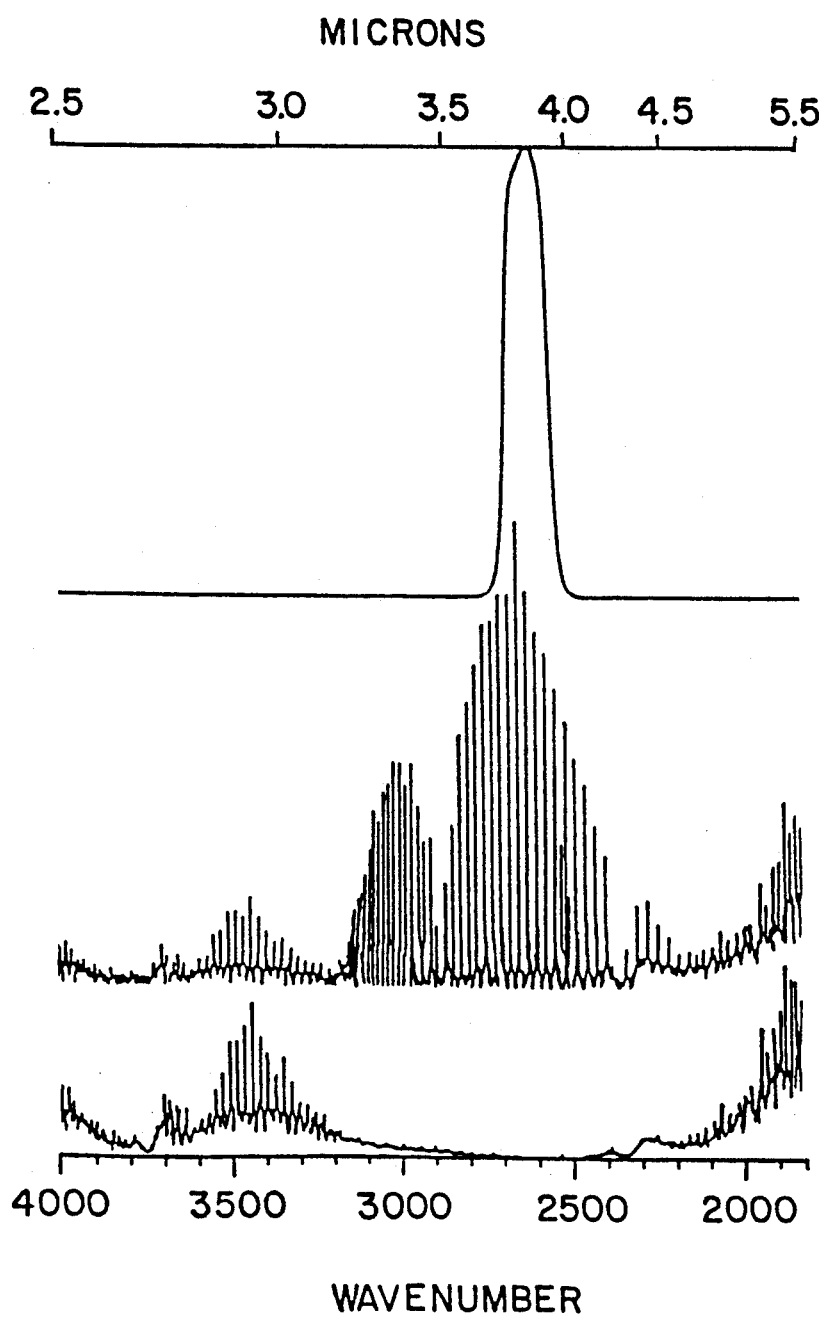
FIGS. 39A to 39C are Fourier-transform infrared spectra from 4000-1800 $cm^{-1}$ plotted on the same relative intensity scale (not corrected for instrument response) of (A) transmission spectrum of the bandpass filter, (B) flame infrared emission spectrum of HCl, and (C) flame infrared emission spectrum showing the background emission from water.

The spectra shown in FIG. 39 were obtained on a Mattson Cygnus 100 Fourier-transform infrared spectrometer. FIG. 39A is a transmission spectrum of the bandpass filter used in the flame infrared emission detector (maximum transmission at 3.8 μm 75% T, <0.10% elsewhere). FIG. 39B is a flame infrared emission spectrum from a hydrogen/entrained-air flame containing hydrogen chloride wherein the strong HCl stretching vibration is centered at 2900 $cm^{-1}$. FIG. 39C is a flame infrared emission spectrum from a hydrogen/entrained-air flame in the absence of hydrogen chloride showing the background emission from water. The resolution conditions are sufficient to reveal the rotational fine structure associated with the P- and R-branches of the HCl emission band (FIG. 39B). As shown in FIG. 39A, the 3.8 μm bandpass filter optically isolated the 3.64–4.03 μm portion of the R-branch of the HCl emission band. The corresponding flame background spectrum (FIG. 39C), shows that this region of the spectrum should be ideal for the detection of hydrogen chloride. A comparison of FIGS. 39A and 39C also indicates that a filter with a somewhat wider bandpass could have been used and would have been desirable from the standpoint of enhancing the total HCl emission received by the PbSe detector. However, to our knowledge, the filter selected for this study possessed the widest spectral bandpass in this region of any which were commercially available.

In contrast to the intensity of the water emission bands lying within the bandpass of the 4.4 μm $CO_2$ filter, the water emission bands occurring within the bandpass of the 3.8 μm HCl filter are relatively weaker (FIG. 39C) and produce a background signal approximately 12 times lower than in the case of $CO_2$ detection. Since the intensity of the HCl infrared emission band transmitted through the 3.8 μm optical filter is also weaker in comparison to the intensity of the $CO_2$ infrared emission band transmitted through the 4.4 μm optical filter, a detector-noise-limited situation was encountered, i.e. the noise amplitude was independent of the flame.

In order to increase the signal at the detector and, thus, improve the signal-to-noise ratio (SNR) of the system, two additional instrumental modifications were made. First, the detector bias voltage was increased from 30 V to 45 V in order to enchance the detectivity of the PbSe detector (*Infrared Detectors;* Hamamatsu Photonics, K. K., Solid State Division; 1126 Ichino-cho, Hamamatsu City, 435, Japan, February 1985). Second, a back collection mirror 384 (FIG. 38) was added behind the burner 383 to increase the light throughput of the optical system. The location of this mirror 384 was determined experimentally by adjusting the mirror position until the signal from the flame background water emission was maximized at the detector. Use of the mirror 384 enhanced the light throughput by a factor of 2.5. Both of these modifications resulted in improved SNR's and lower detection limits.

The purging apparatus (FIG. 38) consisted of two separate chambers, one for sample introduction and chlorine generation, and a second which served as a reference. Two, three-way valves permitted the He purge gas flow to be switched from one chamber to the other between sample determinations. In the previous study (Kubala et al, *Anal. Chem.,* 1989 Vol. 61 pgs. 1841–1846), degassed water was used in the reference purge tube 388 to maintain a constant flow of He saturated with water vapor to the flame. However, due to the corrosive nature of $Cl_2$ gas in the presence of water, it was found necessary to flow dry He through the reference chamber and the sample introduction system between sample determinations. This removed residual moisture from the walls of the sample introduction system and reduced corrosion of the burner and plugging of the sample introduction capillary. Therefore, in contrast to the flame infrared emission-TIC procedure, the flame infrared emission-Cl procedure employed a dry reference purge tube 388.

Because the flame infrared emission system functions as a mass flow-rate detector as shown in Experiment 2, the intensity of the signal arising from the vibrational excitation of HCl in the hydrogen flame is a function of both the He flow rate and hydrogen/air ratio. Although higher He flow rates resulted in increased peak heights and therefore increased signal-to-noise ratios, a practical upper limit was reached when the sample was forced out of the purge tube. A He flow rate of 130 mL/min was determined to represent the best compromise condition for maximizing signal-to-noise ratio without sample loss.

Because chlorine gas must be reduced by $H_2$ at flame temperatures to produced HCl

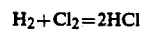

a fuel-rich flame was expected to enhance HCl emission and improve detection limits. As anticipated, a pure $H_2$ flame, supported only by entrained air, afforded SNR's that were approximately 2.5 times greater than those obtained under fuel-lean flame conditions.

To perform chloride determinations using the flame infrared emission system, the chloride ion must first be oxidized to chlorine gas in the sample chamber. The generation of chlorine gas from aqueous chloride samples requires a suitable oxidizing medium. To be satisfactory for use with the flame infrared emission detector, the oxidizing agent must meet two basic requirements. First, it must have a reduction half-cell potential sufficient to oxidize chloride ion to chlorine (in excess of +1.36 volts under standard conditions). Second, the kinetics of the oxidation must be fast. If generation of chlorine gas does not proceed rapidly, broad peaks will be obtained which adversely affect the sensitivity of the system.

Several oxidizing agents were investigated, including concentrated solutions of acidified potassium peroxydisulfate, manganese dioxide, and potassium permanganate. While acidified solutions of both potassium peroxydisulfate and maganese dioxide have suitable half-cell potentials for the reaction, the rate of chlorine production was too slow to be useful for the analysis. By contrast, saturated aqueous $KMnO_4$ and concentrated $H_2SO_4$ generated chlorine rapidly and quantitatively, and permitted analysis by the flame infrared emission system with good detection limits.

More extensive investigations also showed that the sulfuric acid played a role beyond that of supplying hydrogen ions for the reaction, which in excess permanganate is,

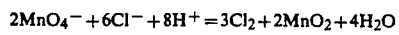

By first introducing the chloride-containing solution onto the glass frit of the purge tube and then adding concentrated sulfuric acid, considerable heat was generated. This heat was found to be critical for promoting the rapid generation of $Cl_2$ in the next step of the procedure when permanganate was added.

Sulfuric acid and deionized water were first introduced onto the frit, a stable baseline was re-established (about 70 seconds), and finally the bleach sample was introduced onto the hot, degassed acid. This procedure produced sharp peaks with good reproducibility. Although the reverse procedure (acid added to the degassed bleach) was not tested, degassing the bleach was avoided since the procedure could result in loss of dissolved chlorine ($Cl_2$) from the sample and degrade the accuracy of the analysis.

Figure 40:
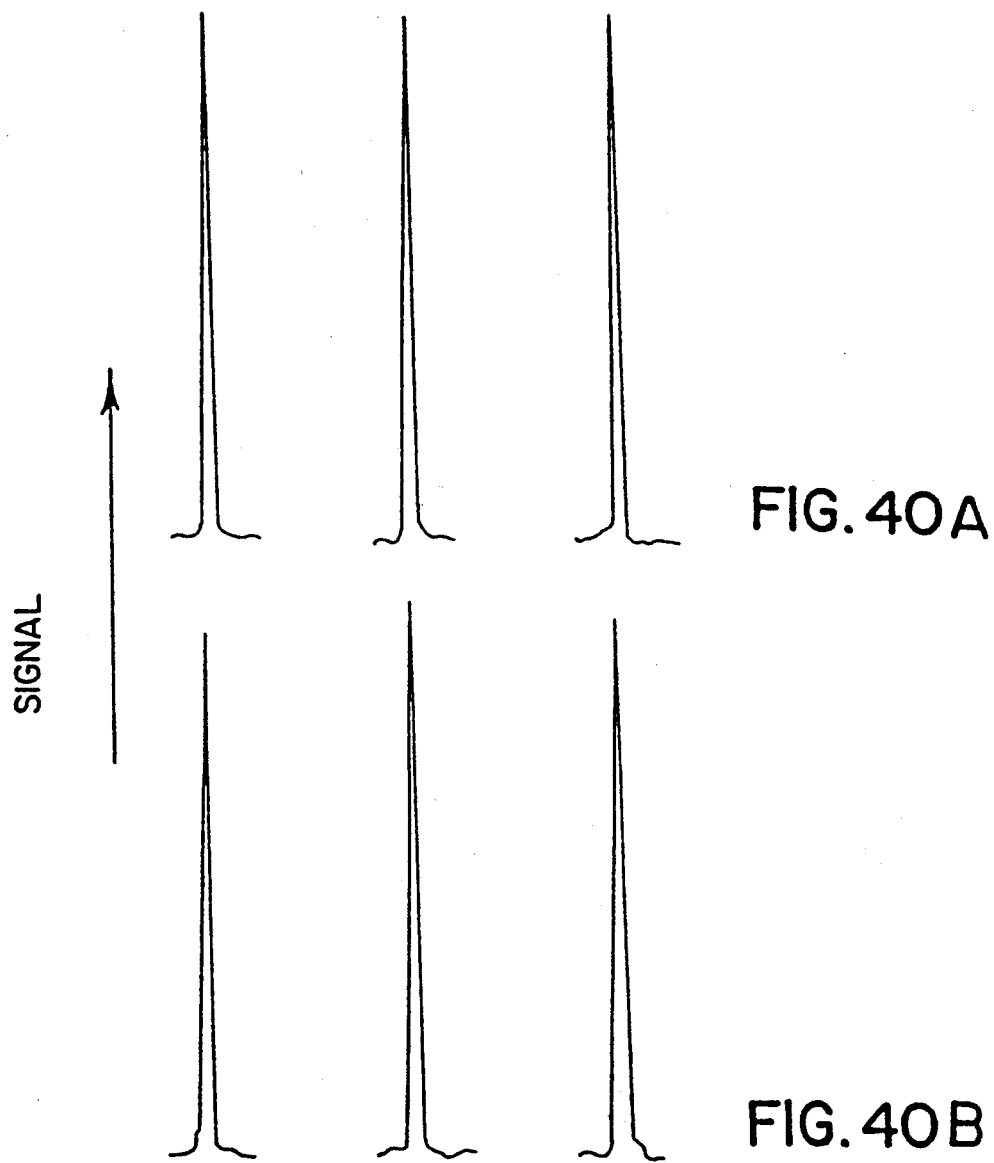
FIGS. 40A and 40B are hydrogen chloride signal profiles obtained by (A) treatment of an acidified aliquot of an NaCl solution with saturated $KMnO_4$ and (B)

The total time required for signal acquisition from an aqueous sample was approximately 3.5 min (from initial acid injection to purge tube disconnection and clean-up). By judicious selection of the oxidizing medium (for chloride) and proper ordering of reagent addition, good peak profiles were obtained (FIG. 40). The hydrogen chloride signal profiles shown in FIG. 40A were obtained by treatment of an acidified 1.0 ml aliquot of 8.00 mM NaCl solution with saturated $KMnO_4$ and those shown in FIG. 40B were obtained by the addition of concentrated surfuric acid to a 0.1 ml aliquot of acidified bleach sample, diluted 20-fold (4.0 umoles available chlorine). Since both the oxidation of chloride by permanganate and the formation of chlorine gas from hypochlorite by acidification tend to be slow at room temperature, the heat supplied by the hydration of sulfuric acid is a critical factor in controlling the kinetics of the reactions, and, hence, the shape of the peak profiles.

The reproducibility of the flame infrared emission procedures was studied by recording the signals from oxidizing eight 1.0-mL aliquots of a 5 mM NaCl standard. The relative standard deviation (RSD) was determined to be 3.34% for peak height measurements and 5.08% for peak area measurements. The difference in reproducibility between the peak height measurements and the peak area measurements most probably occurs in the trailing edge of the peak profile as discussed by Kubala et al, *Anal Chem.*, 1989, Vol. 61 pgs. 1841-1846.

Since the peak height measurements were consistently more reproducible for the standards and aqueous samples used in this study, peak height measurements were used exclusively. The root-mean-square signal-to-noise ratio ($SNR_{rms}$) was appoximately 223:1 for the HCl signals obtained from the oxidation of the 5.0 mM NaCl standard.

Calibration curves were prepared by oxidizing 0.10 to 10 mM NaCl standards and were found to be linear (correlation coefficient of 0.9997). The linear regression equation for a typical calibration curve possessed a slope of 11.46 mm/mM and a y-intercept of −0.09 mm. The detection limit for $Cl^-$ wit the flame infrared emission-chlorine system, defined as a concentration of $Cl^-$ producing a signal equivalent to twice the rms noise, was found to be 1.59 ppm ($4.49 \times 10^{-2}$ mM $Cl^-$). The detection limit for available $Cl_2$, based upon the $Cl^-$ calibration curve (and defined at twice the rms noise), was found to be 1.61 ppm ($2.26 \times 10^{-2}$ mM $Cl_2$).

Natural water and oil brine samples were used to evaluate the analytical performance of the flame infrared emission-chlorine system for the determination of aqueous chloride. The natural water samples included tap water from the Texas cities of Waco and Hewitt, surface waters from Lake Brazos, the Bosque and Brazos River, and brine samples from oil-bearing rock formations. The brine samples were obtained from the Van oil field located in Northeast Texas [Woodbine formation (975 m) and Nacitoch formation (366 m)] and were separated from the associated crude oil by slight heating (80° C.) and centrifugation. A 200-fold dilution of these brine samples was necessary in order to provide a concentration in the linear range of the calibration curve.

TABLE V

Comparison of Chloride Determined by Flame Infrared Emission and by Argentometric Titration for Selected Water and Oil Brine Samples.

| Sample | Titration (ppm)[a] | Flame Infrared Emission | % Rel Error |
|---|---|---|---|
| Hewitt Tap | 61.4 ± 0.1 | 60.6 ± 2.5 | −1.30 |
| Waco Tap | 23.4 ± 0.1 | 25.1 ± 1.8 | +7.26 |
| Bosque River | 17.1 ± 0.4 | 15.2 ± 1.2 | −11.1 |
| Brazos River | 38.2 ± 0.5 | 35.0 ± 0.5 | −8.38 |
| Lake Brazos | 32.0 ± 0.2 | 30.6 ± 1.7 | −4.38 |
| Woodbine Brine | (41.4 ± 0.1) × $10^3$ | (43.0 ± 1.2) × $10^3$ | +3.86 |
| Nacitoch Brine | (17.3 ± 2.0) × $10^3$ | (17.0 ± 0.3) × $10^3$ | −1.73 |

[a]Average and standard deviation of 4 sample determinations.

Table V compares the chloride values determined by argentometric titration using potassium chromate as an indicator with chloride values obtained using the flame infrared emission detector. Each measurement in the table is an average of four replications. Although the tap water samples used in this study were chlorinated, the concentrations of available chlorine as determined by iodometric titration were below the detection limit of the flame infrared emission detector. As a result, no interference from available chlorine was encountered in the determination of chloride ion for the tap water samples used in this study. However, even if the sensitivity of the flame infrared emission system were improved to the point where available chlorine levels in tap water could be detected along with chloride using the flame infrared emission system, interference from available chlorine would be eliminated by the acidification and sample purging step prior to addition of the $KMnO_4$ solution.

As shown in Table V, the precision of the results obtained with the flame infrared emission system is quite good (average relative standard deviation, RSD, 4.39%). The percent difference between the results obtained using the flame infrared emission system and those obtained by argentometric titration (Table V) cannot be ascribed simply to inaccuracies in the flame infrared emission method because the titration method for chloride is subject to interference from such common ions as bromide, iodide, and phosphate. (This will be discussed more fully). It is interesting to note that for the surface water samples (Bosque River, Brazos River and Lake Brazos) the titration method gave results which were all higher than those obtained using the flame infrared emission system. High results obtained by argentometric titration may be indicative of interference from such ions as phosphate which are present in these surface waters. From Table V, the average percent relative difference for the seven samples is 5.43%. The agreement between the results obtained with the flame infrared emission detector and the titration method is very good, considering that the titration method is not totally error free.

Three commercial bleach products were used to test the performance of the flame infrared emission system for the determination of available chlorine. Bleach samples were diluted 20-fold to give a concentration within the linear range of the flame infrared emission calibration curve.

TABLE VI

Comparison of Available Chlorine Determined by Flame Infrared Emission and by Iodometric Titration for Selected Bleach Samples.

| Sample | Titration (ppm)[a] | Flame Infrared Emmision (ppm)[a] | % Rel Error |
|---|---|---|---|
| Bleach Brand X | $(57.2 \pm 0.9) \times 10^3$ | $(60.7 \pm 0.8) \times 10^3$ | +6.12 |
| Bleach Brand Y | $(53.5 \pm 0.1) \times 10^3$ | $(52.4 \pm 0.7) \times 10^3$ | −2.06 |
| Bleach Brand Z | $(55.5 \pm 1.2) \times 10^3$ | $(55.9 \pm 1.6) \times 10^3$ | +0.72 |

[a]Average and standard deviation of 4 sample determinations.

Table VI compares the results obtained for available chlorine by iodometric titration with those obtained using the flame infrared emission detector and shows that the average precision obtained using the flame infrared emission detector is quite good (RSD 1.84%). Taking the iodometric titration as a reference method, the average relative error for the three bleach samples is 2.97%. The close agreement between available chlorine as determined by the flame infrared emission detector and as determined by iodometric titration demonstrates the feasibility of using chloride to prepare the flame infrared emission calibration curve.

Interferences with the flame infrared emission-chlorine analyzer can be classified into two major types: chemical and spectral. Spectral interferences in the flame infrared emission detector will occur whenever purgeable contaminants present in the sample are capable of existing as stable molecules or fragments at flame temperatures and emitting infrared radiation within the bandpass of the filter. Because of the specificity of infrared emission and the judicious selection of notch filters, however, the chance of severe interference (i.e., direct overlap) is not particularly likely.

A more subtle form of spectral interference can result from filter imperfections (or filter bleed). Interference filters of the type used in the flame infrared emission-chlorine analyzer have a small, but finite, transmittance at wavelengths well removed from the peak transmission wavelength. The filter used in this study, for example had a 0.1% transmittance in the vicinity of the 4.42 $\mu$m $CO_2$ emission band. While this transmittance seems small, optical leakage of the $CO_2$ band can produce measureable signals in the presence of large amounts of carbon-containing interferents.

Chemical interferences can occur with the flame infrared emission-chlorine analyzer in a number of ways, such as altering the oxidation process (in the case of chloride) or retarding the purging of chlorine ($Cl_2$) from the sample chamber. Thus, any concomitant which produces a volatile chlorine-containing compound that either does not burn readily in the flame or does not form HCl as a combustion product will depress the signal. Chemical interference can also occur if a non-volatile chlorine-containing compound is produced instead of $Cl_2$ or if a purgeable contaminant reacts with $Cl_2$ in the purge gas stream and reduces the amount of $Cl_2$ reaching the flame.

Bromide, iodide, and phosphate can introduce positive errors in the determination of chloride ion by argentometric titration. Since these anions can be present in natural waters at concentrations as high 1 mg/L [Br], 0.1 mg/L [I], and 0.4 mg/L [P] (*Standard Methods for the Examination of Water and Wastewater*, Greenburg, A. E., Trussel, R. R., Clesceri, L. S., Franson, M. A. H., Eds., American Public Health Association, 16th Ed., Washington, D.C. 1985, pp. 286–294; Manahan, S. E., *Environmental Chemistry*, 3rd. Ed., Willard Grant Press: Boston, Mass. 1979), the effect of these species as possible interferences in the determination of aqueous chloride using the flame infrared emission system was investigated.

To determine the extent to which these anions interfere with chloride determinations performed with the flame infrared emission detector, chloride determinations were repeated using 5 mM NaCl standards which had been spiked with bromide, iodide, and phophate significantly greater than the maximum concentration expected for natural waters. The signals obtained from the spiked solutions were then compared to an unspiked 5 mM NaCl standard.

TABLE VII

Comparison of Flame Infrared Emission Results with Argentometric Titration for Chloride Determination in the Presence of Selected Interferences.

| Sample | Flame Infrared Emission (ppm)[a] | Titration (ppm)[a] |
|---|---|---|
| Blank[b] | 175 ± 7.30 | 175 ± 1.03 |
| Bromide[c] | 107 ± 2.26 | 195 ± 0.621 |
| Iodide[d] | 174 ± 4.32 | 193 ± 1.03 |
| Phosphate[e] | 176 ± 4.94 | 195 ± 2.69 |

[a]Average and standard deviation of 4 sample determination.
[b]5.00 mM (175 ppm) $Cl^-$.
[c]5.00 mM $Cl^-$, 0.595 mM $Br^-$ (equivalent to 21.1 ppm $Cl^-$).
[d]5.00 mM $Cl^-$, 0.595 mM $I^-$ (equivalent to 21.1 ppm $Cl^-$).
[e]5.00 mM $Cl^-$, 0.223 mM $PO_4^{-3}$ (equivalent to 20.6 ppm $Cl^-$).

Table VII shows that the presence of bromide, iodide, or phosphate resulted in a large positive error in the argentometric titration method, with the apparent chloride concentration being given by the sum of the true chloride concentration (175 ppm) and the concentration of the interfering anion, expressed at its chloride equivalent (about 21 ppm). Although no observable difference in peak height occurred in the presence of iodide and phosphate for the flame infrared emission detector (Table VII), a 27% suppression of the HCl signal occured in the presence of bromide. In order to quantify this effect, 5 mM NaCl solutions having different bromide concentrations were prepared and analyzed. A plot of signal versus bromide concentration for 1.0 mL aliquots of 5.00 mM NaCl spiked with NaBr (FIG. 41), although not linear, did indicate an increasing suppression of the HCl signal as bromide ion concentration was increased.

While no attempt was made to identify the exact mechanism responsible for bromide interference in the chloride determination using the flame infrared emission system, the factors involved are almost certainly chemical in nature. The oxidation chemistry of the halides is complicated by the large number of higher oxidation states available to the halogens, and half-cell potentials provide only an approximate guide because the kinetics of the reactions are often slow. However, permanganate and bromine half-cell potentials (adjusted for conditions of the analysis, i.e., approximately 11 molar acid) indicate that in the presence of excess permanganate, bromide can be oxidized to both $Br_2$ and $BrO_3^-$. While bromate would remain in solution, any elemental bromine would be expelled along with elemental chlorine during the purging process. Since the molar solubilities of both $Cl_2$ and $Br_2$ are relatively high [$9.1 \times 10$ moles/L and 0.21 moles/L at 25° C., respectively], both would probably dissolve to some extent in the moisture which condenses between the chlorine generation chamber and the burner. Introduction of chlorine into bromine water under neutral conditions is known to result in the formation of bromate ion, $BrO_3^-$, and chloride ion, $$Br_2 + 5Cl_2 + 6H_2O = 2BrO_3^- + 10Cl^- + 12H^+$$

Any chloride ion which is not swept out of the condensed moisture as HCl during the 15–20 second time period required to record the flame infrared emission signal would contribute to a negative interference.

In the case of iodide, half-cell potentials suggest that reaction with excess permangante is even more likely to produce higher oxidation states [iodate and possibly periodic acid] which would remain in solution. Moreover, any $I_2$ that might form is also relatively insoluble in water [$1.3 \times 10^{-3}$ M] and is much less likely to be purged along with $Cl_2$ in sufficient quantities to act as an interferent. Further support for the proposed mechanism for bromide interference is the observation that increased corrosion and clogging of the stainless steel capillary tube (used to introduce the sample into the burner) occurred during the analysis of samples containing bromide. The presence of these deposits also results in some loss of precision for the chloride results as shown in Table VII.

One method of dealing with bromide interference in the determination of chloride by argentometric procedures is to pretreat the sample using iodate ion in acid solution. The reaction $$IO_3^- + 6Br^- + 6H^+ = I^- + 3Br_2 + 3H_2O$$

selectively produces bromine, which can be expelled by boiling the solution, and iodide ion which is not expected to interfere in the flame infrared emission procedure (Table VII). The feasibility of using iodate to eliminate bromide interference in the flame infrared emission analyzer was investigated, and the results are shown in Table VIII.

TABLE VIII

Comparison of Flame Infrared Emission Results for Chloride Determination in the Presence of Bromide for Several Sample Pretreatment Methods.

| Sample | Flame Infrared Emission (ppm)[a] | % Difference[b] |
|---|---|---|
| Chloride[c] | 175 ± 9 | 0 |
| Chloride/$IO_3^-$[d] | 173 ± 10 | −1.1 |
| Chloride/Bromide[e,f] | 168 ± 10 | −4.0 |
| Chloride/Bromide[e,g] | 166 ± 11 | −5.1 |

TABLE VIII-continued

Comparison of Flame Infrared Emission Results for Chloride Determination in the Presence of Bromide for Several Sample Pretreatment Methods.

| Sample | Flame Infrared Emission (ppm)[a] | % Difference[b] |
|---|---|---|
| Chloride/Bromide[e,h] | 94 ± 7 | −46.3 |

[a]Average and standard deviation of 4 sample determinations.
[b]Percent difference compared to chloride (175 ppm) in the absence of bromide.
[c]5.00 mM (175 ppm) $Cl^-$.
[d]5.00 mM $Cl^-$, 4.70 mM $KIO_3$.
[e]5.00 mM $Cl^-$, 4.70 mM $KIO_3$, 0.60 mM $Br^-$.
[f]Bromine expelled by boiling the solution prior to analysis.
[g]Bromine expelled by purging in the sample chamber prior to analysis.
[h]Bromine and chlorine purged together during analysis.

As shown in Table VIII, pretreatment of 1.0 mL of a 5 mM chloride solution with $KIO_3$ and permanganate did not alter the flame infrared emission results for chloride within experimental error. However, the presence of both iodate and bromide ion in the sample resulted in a 46.3% suppression of the flame infrared emission signal, compared with chloride solutions containing no bromide. This negative interference is even greater than the 27% suppression observed for bromide-containing samples which were not pretreated with iodate (Table VII), and may indicate that $Br_2$ makes up a greater percentage of the bromide oxidation products when iodate is added prior to treatment by permanganate. In contrast, considerably less suppression of the HCl signal occurred when the bromide-containing solution was pretreated with iodate and then boiled for 10 minutes before introduction into the purge tube (−4.0%) or pretreated with iodate and then purged directly in the sample chamber (−5.1%) to expel bromine prior to addition of permanganate. (Again, precision was somewhat degraded due to deposits which formed in the capillary tube during the analysis). These results, although preliminary, indicate that aqueous chloride solutions can be successfully pretreated with iodate to remove bromide interference in the flame infrared emission procedure.

As discussed previously, the flame infrared emission-chlorine procedure is capable of detecting available $Cl_2$ in aqueous samples. Since many municipalities add $Cl_2$ or a chlorine-containing compound (chloroamines) to tap water for disinfection, available chlorine may interfere in the determination of aqueous chloride. Thus, the initial purging step of the acid/sample mixture before oxidation of the aqueous chloride is useful in removing any available $Cl_2$ that may be present in the water sample.

Carbon dioxide can be present in the flame as a result of purging $CO_2$ from an acidified carbonate-containing solution as in Kubals, et al, *Anal. Chem.*, 1989, Vol 61. pgs. 1841–1846 or combusting a purgeable organic compound as in Experiments 1 and 2. Because the transmission characteristics of the 3.8 μm HCl bandpass filter allow for slight filter bleed in the region of the $CO_2$ infrared emission band ]centered at 4.42 μm], carbonates and purgeable organics could act as spectral interferences in the determination of aqueous chloride and available chlorine. In order to determine if the potential interference is detected by the flame infrared emission-chlorine system, 2-μL injections of cyclopentane were introduced into the purge tube in a manner similar to the procedure outlined for the determination of available chlorine (cyclopentane added to hot acid). Although the results were not quantified, they did indicate that a slight, but detectable amount of filter bleed from the $CO_2$ emission band occurred in the transmission of the 3.8 μm HCl optical bandpass filter. Thus, in chloride determination by the flame infrared emission system, the procedure sequence allowing the sample degassing prior to addition of permanganate is important for removing carbonate and volatile organic interferences before the chlorine generation step.

Other possible interferences in the flame infrared emission-chlorine method for chloride are those species that are not purged from solution, but are oxidized to $CO_2$ under the conditions of the flame infrared emission procedure. Permanganate, however, is not a sufficiently strong reagent to oxidize the majority of organic compounds to $CO_2$, and with the exception of a few species such as oxalates and oxalic acids, non-volatile inorganic or organic species are not expected to produce a chemical interference of this type.

The flame infrared emission detection system described in this experiment has been shown to be a sensitive, reproducible, accurate, and direct means of determining chloride in water and available chlorine in liquid bleach. It is easy to use and requires only a one-milliliter sample for each determination. In its present stage of development, the time required for signal acquisition from a sample is 3.5 minutes from the sample injection to purge-tube disconnection and clean up. The system is easily amenable to automation, and a multiple purge-tube version is envisioned.

Although only aqueous chloride and liquid bleach samples were investigated, it is possible to apply the flame infrared emission method to the determination of chlorine in any sample which can be pretreated to form elemental chlorine or hydrogen chloride in the sample chamber or contains purgeable chlorine-containing compounds which can be combusted to hydrogen chloride in the flame. Thus, determination of such species as chlorites, chloroamines, chlorine dioxide and volatile organic chlorides is feasible. A special advantage of the flame infrared emission method is its lack of interference from iodide and phosphate, two ions which cause large positive errors in the determination of chloride by argentometric titration. The interference caused by bromide ion in the flame infrared emission method should be eliminated by sample pretreatment using iodate.

EXPERIMENT 5

The schematic layout for the dual channel flame infrared emission detector is shown in FIG. 42. The detection system consists of an optical dual channel module, followed by the electronic signal processing module.

The dual channel optical arrangement is made up of a flame excitation source 421 (Hydrogen/air combustion flame), collimating lens 422, focusing lenses 423 and 424, mirrror 425, zinc selenide beam splitter 426, mechanical light beam chopper 427 (for signal modulation), and optical band pass filters 428 (for spectral band isolation).

The light from the source 421 is collimated by a calcium fluoride lens 422 of focal length 5 cm (P#43150- Oriel corporation- Stratford - Conn.), and the mirror 425 of focal length 2.5 cm (P#44350- Oriel corporation - Stratford - Conn.). The collimated radiation is then modulated at a frequency of 570 Hz by a mechanical light beam chopper 427 (designed and machined locally in this lab). The modulated radiation is then passed through a zinc selenide beam splitter 426 (P#45360- Oriel corporation- Stratford - Conn.), which serves the role of a beam splitter dividing the radiation in two portions. Each portion of the divided radiation is then focussed onto a 1×5 mm lead selenide detector 429 (P#P791- Hamamatsu Corporation- Bridge water-N.J.) by calcium fluoride lenses 423 and 424 of focal length 5 cm (P#43150 - Oriel corporation- Stratford - Conn.). Optical band pass filters 428 were placed in front of the detectors for isolating the spectral bands of interest. The filters 428 used were (1) 3.0±0.03 μm narrow band pass filter (P#58160- Oriel corporation-Stratford - Conn.), (2) 4.4±0.03 μm narrow band pass filter (P#58300- Oriel corporation-Stratford - Conn.), (3) 3.8±0.03 μm narrow band pass filter (P#58230 - Oriel corporation- Stratford - Conn.), (4) 2.35±0.01 μm narrow band pass filter (P#Spectrogon- Secaucus - N.J.), (5) 2.5±0.05 μm short pass filter (P#Spectrogon-Secaucus N.J.).

One half of the divided optical path serves as the reference channel for monitoring the source background fluctuations, and the other half as the analytical channel for monitoring the analytical signals of interest. The 3.0 μm filter wa placed in the reference channel to monitor and compensate for the background fluctuations in the flame due to $H_2O$ emission from the flame. Depending on the desired analyte, the 4.4 μm notch filter (to isolate the $CO_2$ emission band), the 3.8 μm notch filter (to isolate the HCl band), or 2.35 μm notch filter in combination with the 2.5 μm short pass filter (to isolate the HF band) could be placed in the analytical channel. The additional short pass filter was necessary, to effectively isolate the HF band from the strong interference band at 3.0 um due to background emission from $H_2O$ present in the flame.

The pre-amplifier circuit configuration for the dual channel system is shown in FIG. 43. The lead selenide detectors 431 and 432 were biased at +70 volts from a regulated dc power supply (P#6516 Hewlett Packard- Avondale- Calif.). The biasing circuit was tied together to the common power supply to achieve the classical Wheatstone bridge configuration. The value of the matching load resistors (300k) 434 and 435 for biasing the lead selenide detectors were chosen based on the manufacturer's specification sheet. A 20K ohm multi-turn trimmer potentiometer 433 was connected in series with the resistor 434, which along with the detector 431 constitute the reference arm of the wheatstone bridge network. The potentionmeter 433 was used to fine tune the zero adjustment of the Wheatstone bridge to achieve an accurate balance condition. The voltages, $V_{Ri}$ and $V_{Ai}$ developed at the junctions R and A respectively were amplified separately by the pre-amplifier circuits. The pre-amplifier circuit configuration of the reference and analytical channels are identical in all respects (in terms of the values of the resistor and capacitors, and the operational amplifers used). A BIFET operational amplifier (TL 071-Texas instruments - Dallas- Tex.) was used. The operational amplifiers were powered from a standard regulated ±15 V dual dc power supply (P#2718 - Heath Co - Benton Harbor-Mich.). The pre-amplifier output $V_{Ro}$ and $V_{Ao}$ were then connected separately to the B and A input of the lock in amplifier (Ithaco-3962 single phase lock in amplifier - Ithaca - N.Y.). The differential imput mode (A−B) of the lock-in amplifier was chosen for operation. Under these conditions the output of the lock-in amplifier is also the differential output, i.e. $V_{Ao} - V_{Ro}$.

The following represent typical operating conditions for the dual channel system. With just the flame background seen by both channels, the signal from the analytical channel (with the appropriate band pass filter in place) was connected to the A input of the lock in amplifier which was operated in the single ended input mode. After proper phase setting and time constant adjustment, the approximate value of the signal was recorded. The analytical channel signal was disconnected from the lock in amplifier input and the reference channel signal was connected. The reference channel signal level was approximately 50 times greater than the analytical channel signal level. The signal level to the reference channel was attenuated optically with an iris diaphragm 420 placed in front of the lens 424. The aperture width of the iris was adjusted until the signal level in the reference channel was approximately the same as in the analytical channel. The analytical channel signal was then re-connected back to the A input of the lock-in amplifier and the reference channel signal was then connected to the B input of the lock-in amplifier. The differential input mode (A−B) of the lock-in amplifier was chosen for operation. The aperture width was then adjusted further until the output of the lock-in amplifier was approximately zero. Finer zero adjustments were made with the help of the trimmer potentiometer 433. The output of the lock-in amplifier was connected to a recorder/integrator (P#HP3394A-Hewlett Packard Avondale-Calif.) for subsequent data processing.

A Shimadzu Gas chromatograph (model GC-8A-Shimadzu Instrument Inc- Columbia-Md.) with a thermal conductivity detector and temperature programming capability was used throughout this work. The outlet of the column was interfaced to the burner body of the flame infrared emission detector by the method already described for Experiment 2. The design and construction of the burner are as described for Experiment 1 and 2. The stainless steel capillary interface tube was wrapped with a heating tape and the temperature of the heating tape was maintained at 250° C. This was necessary to prevent the column effluent from condensing in the interface tube. The capillary burner head supported a hydrogen-air combustion flame. The $H_2$ and the air flow rates to the burner were regulated by means of standard flow meters (P#3227-20 (for hydrogen) and P#3227-26 (for air) Cole Parmer company - Chicago Ill.). The gas chromatographic column used throughout this work was a 6 ft×⅛″ SP alloy column packed with carbopack-B and 5% Fluorocol. (P#1-2425 - Supelco Inc- Bellafonte -Pa.). This column is specially designed for separation of fluoro and chloro carbons. Helium was used as the carrier gas through out and a flow rate of 30 mL/min was used. The liquid samples were introduced into the gas chromatograph by means of standard Hamilton microliter syringes. All the optical components were mounted on aluminum blocks designed and machined locally. The aluminum mounts were painted flat black to minimize stray radiation and reflections reaching the detector. A shield made of aluminum and painted flat black on both the inside and the outside was placed around the burner to minimize flame flicker due to air currents from the atmosphere and the chopper blade. All experiments were performed after a 30 minute warm-up period to allow for the stabilization of electronic components and lead selenide detector response.

Preliminary optimization studies were undertaken to optimize and evaluate the performance characteristics of the dual channel system. The parameters chosen for optimization were (a) selectivity ratio and (b) minimum detectable quantity or detection limits. These are the two most important figures of merit of any selective detection system, since a given selective detection system should have a high selectivity towards a species of interest and at the same time should be able to detect very small quantities of that species. The experimental variables that were considered to have a significant effect on these two parameters were (a) detector bias voltage (b) the optical filter in the reference channel for background compensation and (c) the method of balancing the Wheatstone bridge network.

The experiments were conducted with Freon-113 and pentane as representative analytes. Freon-113 was used to evaluate the response of the system in the fluorine, and chlorine selective modes of operation. Pentane was used as the hydrocarbon comparison standard for evaluation of selectivity ratios of the fluorine and the chlorine modes of operation, since pentane does not produce any HCl or HF on combustion. Typical selectivity ratios and detection limit calculations are shown in Table IX for the fluorine selective mode of operation.

TABLE IX

| | Subtracted Mode | Unsubtracted Mode |
|---|---|---|
| VOLUME OF FREON-113 INJECTED (ml) | 0.001 | 0.001 |
| VOLUME OF PENTANE INJECTED (ml) | 0.010 | 0.001 |
| SIGNAL FOR FREON-113 (mm) | 123 | 113 |
| SIGNAL FOR PENTANE (mm) | 4.0 | 17 |
| RMS NOISE (mm) | 0.1 | 1.0 |
| (S/N) Ratio (FOR FREON-113) | 1225 | 113 |
| DENSITY OF FREON-113 (gm/ml) | 1.575 | 1.575 |
| PEAK WIDTH FOR FREON-113 (sec) | 24 | 24 |
| DETECTION LIMIT FOR FREON-113 (ng/sec) | 107 | 1160 |
| SELECTIVITY RATIO | 305 | 7 |

In Table IX the detection limit for Freon-113 was calculated from the following equation $$\frac{2 \times V_{FC\text{-}113} \times d_{FC\text{-}113}}{(S/N)\text{Ratio} \times \text{Peak Width}} \times 10^9$$

wherein V is volume (mL) injected and d is density (g/mL). The selectivity ratio is the ratio of the signal for Freon-113/signal for pentane.

A study of the effect of detector bias voltage on the selectivity ratio and detection limits was carried out. The 4.4 μm filter was placed in the reference channel for background compensation and the 2.35 & 2.50 μm filters were placed in the analytical channel to isolate the HF bands. The chromatographic conditions were the same as described above. The experiments were carried out at 180° C. (isothermal) and one and ten microliter sample sizes were used. The results are summarized in table X, and graphically illustrated in FIG. 44.

TABLE X

| NO | DETECTOR BIAS VOLTAGE (VOLTS) | MINIMUM DETECTABLE QUANTITY (micrograms/sec) | SELECTIVITY RATIO |
|---|---|---|---|
| 1 | 30 | 1.95 | 52 |
| 2 | 40 | 1.70 | 58 |
| 3 | 50 | 1.52 | 63 |
| 4 | 60 | 1.44 | 70 |
| 5 | 70 | 1.46 | 77 |
| 6 | 80 | 1.55 | 83 |
| 7 | 90 | 1.70 | 87 |

The results indicate that even though the selectivity ratio (fluorine/carbon) increases linearly with increasing detector bias voltage the minimum detectable quantity (MDQ) of Freon-113 shows a distinct minimum around 70 volts, and a further increase in the bias voltage leads to poorer detection limits. Based on these results a detector bias voltage of 70 volts was chosen as an optimum value for further experiments.

A study to evaluate the relative efficiency of the reference channel filters to compensate for the source background fluctuations was carried out. The two filters compared were the 3.0 μm filter (to compensate for source background fluctuations due to $H_2O$ emission in the flame), and the 4.4 μm filter (to compensate for the $CO_2$ emission resulting from the combustion). The results of the filter comparison are summarized in Table XI.

TABLE XI

| FILTER COMPARISON | SUBTRACTED MODE (micron filter) 3.0 | 4.4 | UNSUBTRACTED MODE |
|---|---|---|---|
| 1. SELECTIVITY RATIO | | | |
| a. Fluorine Mode | 305 | 81 | 7 |
| b. Chlorine mode | 175 | 114 | 6 |
| 2. DETECTION LIMIT nanograms/sec | | | |
| a. Fluorine Mode | 107 | 1150 | 1160 |
| b. Chlorine Mode | 375 | 1440 | 1010 |
| c. Carbon Mode | 112 | — | 127 |

These results clearly indicate that with the 3.0 μm filter in the reference channel, both selectivity ratio and detection limits are far better than with the 4.4 μm filter. The corresponding results for the unsubstracted mode of operation are given for the sake of comparison. With the 4.4 μm filter in the reference channel, even though the selectivity ratio is better than that in the unsubtracted mode, the detection limits are slightly worse, but with the 3.0 μm filter in the reference channel both the selectivity ratio and the detection limits are substantially better than the corresponding unsubtracted mode. Based on these results the 3.0 μm filter was chosen for background compensation in further studies.

The Wheatstone bridge configuration for implementing the background compensation has already been discussed. The bridge balancing condition was actually achieved by two different methods and the relative performances of these methods were evaluated with the two parameters i.e. selectivity ratio, and detection limits. The two methods compared are (1) optical attenuation and (2) electronic attenuation. A brief discussion of these two methods is presented in the following section.

The Wheatstone bridge network used for the optical attenuation method is shown in FIG. 43. This method has already been discussed. The bridge balance condition was achieved (under the flame background conditions) by optically attenuating the signal intensity in the reference channel by means of an iris diaphragm, until it approximately equaled the signal in the analytical channel. Under these conditions any fluctuations in source intensity common to both channels would mutually cancel each other and only signals due to species of interest would appear in the analytical channel.

The electronic attentuation method could further be classified into (1) an adjustable load resistor method and (2) an adjustable pre amplifier gain method.

The Wheatstone bridge network used in the adjustable load resistor method is shown in FIG. 45. In this method the bridge balance (under the flame background conditions) was achieved by adjusting the value of the resistance of the load resistor 451 on the reference arm of the bridge. The load resistor 451 and the lead selenide detector 453 constitute the reference arm of the wheatstone bridge. The load resistor 451 on the reference channel is a multiturn trimmer potentionmeter whose value could be adjusted until the potential at points R and A are approximately equal. Under these conditions the signal levels $V_{Ri}$ and $V_{Ai}$ are equal and hence differential output $(V_{Ao}-V_{Ro})$ is zero.

The Wheatstone bridge network used in the adjustable pre-amplifier gain method is shown in FIG. 46. It is essentially the same as used in the previous method, shown in FIG. 45, the only difference being that the signal levels $V_{Ao}$ and $V_{Ro}$ are made equal by adjusting the gain of the reference preamplifier circuit with a gain control resistor 465. The gain of the reference channel circuit was adjusted until the signal level $V_{Ro}$ became equal to $V_{Ao}$. Under these condition the differential output $(V_{Ao}-V_{Ro})$ is zero.

The results obtained for these three methods are summarized in Table XII.

TABLE XII

| SUBTRACTED MODE | OPT. ATTEN-UATION | ELECTRONIC ATTENUATION Load Resistor/Preamp Gain |
|---|---|---|
| 1. Selectivity Ratio | | |
| a. Fluorine Mode | >726 | 766/305 |
| b. Chlorine Mode | >238 | 282/175 |
| 2. Detection Limits (nanograms/sec) | | |
| a. Fluorine Mode | 96 | 547/107 |
| b. Chlorine Mode | 116 | 850/375 |
| c. Carbon Mode | 22 | 26/122 |

The corresponding results for the unsubtracted mode of operation are given in Table XIII.

TABLE XIII

| UN-SUBTRACTED MODE | OPT. ATTEN-UATION | ELECTRONIC ATTENUATION Load Resistor/Preamp Gain |
|---|---|---|
| 1. Selectivity Ratio | | |
| a. Fluorine Mode | 16 | 6/9 |
| b. Chlorine Mode | 9 | 9/6 |
| 2. Detection Limits (nanograms/sec) | | |
| a. Fluorine Mode | 1130 | 2620/1160 |

TABLE XIII-continued

| UN-SUBTRACTED MODE | OPT. ATTEN-UTATION | ELECTRONIC ATTENTUATION Load Resistor/Preamp Gain |
|---|---|---|
| b. Chlorine Mode | 1190 | 1650/1010 |
| c. Carbon Mode | 231 | 242/127 |

The results indicate that the optical attenuation method offers the optimum values of detection limits and selectivity ratio, and based on the results this was the method of choice for balancing the bridge network in all the subsequent experiments. The preliminary optimization studies lead to the choice of the following factors for subsequent experiments:

a) A detector bias voltage of +70 volts, b) A 3.0 μm filter in the reference channel for background compensation, and c) The optical attenuation method to balance the bridge network.

Table XIV summarizes the relative performance of the dual channel system in the subtracted mode to that of the unsubtracted mode obtained under the optimum conditions mentioned above.

TABLE XIV

| | SUBTRACTED MODE | UNSUBTRACTED MODE |
|---|---|---|
| 1. Selectivity Ratio | | |
| a. Fluorine Mode | >726 | 16 |
| b. Chlorine Mode | >238 | 9 |
| 2. Detection Limits (nanograms/sec) | | |
| a. Fluorine Mode | 96 | 1130 |
| b. Chlorine Mode | 116 | 1190 |
| c. CARBON MODE | | |
| 1. For Freon-113 | 22 | 231 |
| 2. For Pentane | 2 | 265 |

The response for pentane in the carbon mode is included for the sake of comparison. In the unsubtracted mode the detection limit for pentane and for Freon-113 are about the same. However, in the unsubtracted mode, the detection limit for pentane is about an order of magnitude better than that for Freon-113.

The response characteristics of the dual channel system in the three different selective modes (carbon, chlorine, fluorine) were evaluated. Calibration standards of Freon-113 in dichloromethane were prepared in the concentration range from 0.1 to 10 micrograms. The calibration standard of Freon-113 was chromatographed at 180° C. (isothermal), on a Carbopack-B (5%Fluorocol) column, with helium as the carrier gas at a flow rate of 30 ml/min. The chromatographic peak height was plotted as a function of amount of Freon-113 injected. The results are summarized in Table XV and the calibration plots are shown in FIG. 47. The calibration plots indicate excellent linearity in the detector response for the amounts of Freon-113 injected.

TABLE XV

| # | Amount of Freon-113 injected (micrograms) | Peak Height (mm) Fluorine Mode | Chlorine Mode | Carbon Mode |
|---|---|---|---|---|
| 1 | 0.212 | 1.0 | 0.9 | 4.0 |
| 2 | 0.430 | 1.8 | 1.6 | 6.0 |
| 3 | 0.630 | 3.5 | 3.7 | 10.0 |
| 4 | 0.612 | 5.0 | 4.7 | 12.0 |
| 5 | 1.013 | 7.0 | 6.0 | 15.2 |
| 6 | 2.152 | 13.0 | 12.0 | 23.0 |
| 7 | 3.130 | 19.0 | 19.0 | 32.0 |
| 8 | 4.060 | 24.0 | 25.0 | 42.0 |
| 9 | 5.074 | 34.0 | 29.0 | 40.0 |
| 10 | 6.093 | 43.0 | 39.0 | 60.0 |
| 11 | 7.067 | 47.0 | 44.0 | 68.0 |
| 12 | 8.092 | 54.0 | 50.0 | 78.0 |
| 13 | 9.035 | 60.0 | 56.0 | 86.0 |
| 14 | 9.866 | 66.0 | 62.0 | 88.0 |

Based on the results obtained for the preliminary optimization of the dual channel system, it can be safely concluded that the background subtraction to compensate for source fluctuations leads to a much superior detection system in comparison to the unsubtracted mode of operation. This conclusion is exemplified by the two parameters: (a) selectivity ratio and (b) detection limits. Further investigations were carried out to test and evaluate the performance of the dual channel system and see how well the these improvements translate in a real-time analysis situation. A gas chromatographic separation of a chlorofluorocarbon mixture was chosen for this purpose. The essential idea behind this approach was that in a mixture of chlorofluorocarbon and hydrocarbons chromatographed under an element selective mode, only the compounds containing the given element of interest would respond while others would be virtually excluded. A synthetic mixture of seven compounds consisting of chlorinated, fluorinated and aliphatic hydrocarbons was prepared. The composition of this mixture and the chromatographic conditions are given below. (1) dichloromethane (300 μg) (2) trichlorofluoromethane (150 μg) (3) trichloromethane (400 μg) (4) trichloro trifluoroethane (150 μg) (5) tetrachloromethane (400 μg) (6) hexane (20 μg) (7) heptane (20 μg). This mixture was separated on a Carbopack (5% fluorocol) column under temperature programming from 140° C. to 190° C. at 20° C./min with helium as the carrier gas at a flow rate of 30 mL/min. The fluorine selective mode of operation was carried out with the 2.35 μm and 2.50 μm filter combination in the analytical channel. The chlorine selective mode was carried out using the 3.8 μm filter in the analytical channel. The carbon mode of operation was carried out using the 4.4 μm filter in the analytical channel. A 3.0 um filter was used throughout in the reference channel.

All chromatograms were run under identical conditions. The chromatograms are shown in FIG. 48.

In the carbon mode 7 peaks result with the order of elusion from left to right as listed above. The compounds exhibiting peaks in the chlorine mode are from left to right (1) dichloromethane, (2) trichlorofluoromethane, (3) trichloromethane, (4) trichlorotrifluoroethane and (5) tetrachloromethane. In the fluorine mode only the two fluorinated compounds (2) trichlorofluoromethane and (4) trichlorotrifluoroethane are present from left to right. The chromatograms are shown in the subtracted and unsubtracted modes to illustrate the relative performance in the three selective modes of operation.

The results indicate that in the chlorine selective mode only the chlorinated compounds respond and similarly in the fluorine selective mode only the fluorine containing compounds respond. This confirms the preliminary results obtained earlier in terms of the selectivity ratio values obtained for the element selective mode. Also the results of the unsubtracted mode of operation are given for comparison. It is clear from these results that in the unsubtracted mode (for the chlorine and fluorine selective modes) the signal to noise ratio is far worse than in the subtracted mode. The signal-to-noise ratio improvements are about an order of magnitude better for the subtracted mode in comparison to the unsubtracted mode. In the fluorine and chlorine selective unsubtracted modes the analyte peaks are just barely visible above the noise. In fact, the peak heights are just about twice the rms noise level (the theoretical criterion for detection limit).

The real advantage of the element selective mode of operation of the GC-flame infrared emission detector over the commercial non selective GC detectors can be appreciated in situations calling for the analysis of fluorinated compounds in a complex matrix containing a host of non-fluorinated compounds. Qualitative and quantitive analysis of such a complex mixture can be very tedious and is often plagued with serious quantitative errors. Unambiguous qualitative identification can be very frustrating as a result of tedious steps involved in optimization of separation conditions. A reliable quantitative analysis can be highly complicated in the absence of complete resolution of the component peaks. When the analyst is interested only in the fluorinated compounds and not in the myriad of other components present in the matrix, then the fluorine selective GC-flame infrared emission detector provides the ideal choice. Since the fluorine selective mode of the detector responds selectively only to the fluorinated compounds, a simpler chromatograph with less peaks results, obviating the need for tedious and elaborate optimization schemes. Unambiguous qualitiative identification and reliable quantitative data can be achieved under these conditions. As a part of our investigative study of the performance of the dual channel system operating in the fluorine selective mode, we have attempted to simulate such a condition; the details of the experimental approach are descibed in the following section.

A complex 19-component mixture of various organic compounds was prepared by mixing these compounds in approximately equal proportions by volume. The composition of this mixture is given below. (1) chlorobenzene, (2) chlorotoluene, (3) 2-chlorobutane (4) 1-chloro-2-methyl butane, (5) 1-chloro-2-methylpropane, (6) isopropyl chloride, (7) 1,3-dichloro-1-propene, (8) 3-pentanone, (9) ethyl acetate, (10) ethanol, (11) carbon tetrachloride, (12) chloroform (13) dichloromethane, (14) pentane, (16) fluorobenzene, (16) difluorobenzene, (17) hexafluorobenzene, (18) trichlorotrifluoroethane, (19) methanesulfonyl fluoride. This mixture contains only 5 fluorinated compounds. The chromatographic conditions chosen for the separation were based on the optimum separation conditions chosen for the separation of the 5 fluorinated compounds. The optimum conditions were arrived at by chromatographing the 5 component mixture of the fluorinated compounds. The optimum chromatographic conditions that resulted were, column: Carbopack-B (5%Fluorocol), helium carrier gas (30 mL/min), temperature programming 180° C. to 220° C. at 20° C./min. The 19 component complex mixture was chromatographed under these conditions, with (a) a commercial TCD detector, (b) a flame infrared emission detector in the carbon mode and (c) a flame infrared emission detector in the fluorine selective mode. The chromatograms for the respective modes are shown in FIGS. 49, 50 and 51. With the TCD detector and the flame infrared emission detector in the carbon mode of operation only 15 peaks out of the total of 19 components are visible indicating an incomplete resolution of component peaks. As a result, no attempt has been made to identify and assign the component peaks in these two modes of operation. With the fluoride selective mode the results are rather impressive. Only the 5 peaks due to the 5 fluorinated components ((1) methanesulfonylfluoride, (2) trichlorotrifluoroethane, (3) fluorobenzene, (4) difluorobenzene and (5) hexafluorobenzene from left to right) are present. The chromatogram looks much simpler with excellent baseline resolution. The intrinsic simplicity of the chromatographic profile lends itself to an unambiguous peak identification. (The actual peak assignments were made using the retention times of these fluorinated compounds from individual injections of these compounds under identical chromatographic conditions).

In a further embodiment, a flame infrared emission detector is combined with a flame ionization detector wherein the same flame is used to simultaneously conduct both types of detection. The flame infrared detector provides better quantitation of moles of carbon present in the compounds while the flame ionization detector provides higher sensitivity to extremely small amounts of hydrocarbons. Additionally the flame infrared emission detector is able to detect compounds not observed by the flame ionization detector such as carbon monoxide and carbon dioxide. An experimental schematic for a combined flame infrared emission flame ionization detector is shown in FIG. 52. The burner body 520 is the same as used for Experiment 2. Hydrogen/Air is used as the fuel/oxidant mixture being supplied to the capillary tubes of the burner through a Swagelok T 523a, 523b. The sample is supplied through the central capillary 526. The flame ionization detector utilizes two electrodes in an electrode assembly 522 where a potential of approximately 300 V DC is regulated between the electrodes by a power supply. An electrometer measures the ion current across the flame.

The infrared emission is simultaneously detected by a PbSe detector 524. Radiation from the flame is modulated by an optical chopper 525. The infrared detector 524 must not "see" the electrodes (due to blackbody emission background), therefore an aperture device is mounted on the infrared detector unit.

Although the invention has been described by reference to some preferred embodiments, it is not intended that the novel infrared detection means and method be limited thereby but various modifications are intended to be included as falling within the spirit and broad scope of the foregoing disclosure, the attached drawings and the following claims.

We claim:

1. A method for detecting and making quantitative measurements of at least one selected component in a sample, in which at least one selected component of the sample, or at least one selected substance present in the sample and characteristic of the at least one selected component, is introduced into an exciting means, and when the at least one selected component is present in the sample, gas-phase, infrared-active molecules emit infrared radiation at at least one characteristic wavelength in proportion to the quantity of the at least one selected component in the sample, comprising the steps of:
   a. exciting the gas-phase, infrared-active molecules with a flame to emit radiation, wherein when the at least one selected component is present in the sample, the gas-phase, infrared-active molecules emit radiation at at least one characteristic wavelength with an intensity proportional to the quantity of the at least one selected component in the sample, and wherein fluctuating background radiation is simultaneously emitted at the at least one characteristic wavelength of the gas-phase, infrared-active molecules and at other wavelengths,
   b. splitting the emitted radiation into first and second beams;
   c. first detecting radiation in the first beam at the at least one characteristic wavelength, and generating a first electrical signal representative of the emitted radiation at at least one characteristic wavelength, and secondly detecting radiation in the second beam having the emitted background radiation and generating a second electrical signal representative of the simultaneously emitted background radiation; and
   d. combining the first and second electrical signals to cancel fluctuations in intensity at the at least one characteristic wavelength caused by fluctuations in the background radiation.

2. A method according to claim 1, wherein said first detecting step includes discriminating the at least one characteristic wavelength by allowing passage of radiation at the at least one characteristic wavelength and inhibiting the passage of other wavelengths, and said second detecting step includes discriminating against the at least one characteristic wavelength by allowing passage of the emitted background radiation and inhibiting the passage of radiation at the at least one characteristic wavelength.

3. A method according to claim 1, wherein said combining step includes subtracting the second electrical signal from the first electrical signal.

4. A method according to claim 1, further including attenuating the second beam to adjust the level of the second output signal.

5. A method for detecting and making quantitative measurements of at least one selected component in a sample, in which at least one selected component of the sample, or at least one selected substance produced from the at least one selected component in the sample and characteristic of the at least one selected component, is introduced into an exciting means, and when the at least one selected component is present in the sample, gas-phase infrared-active molecules emit infrared radiation at at least one characteristic wavelength in proportion to the quantity of the at least one selected component in the sample, comprising the steps of:
   a. exciting the gas-phase, infrared-active molecules with a flame to emit radiation, wherein when the at least one selected component is present in the sample, the gas-phase infrared-active molecules emit radiation at at least one characteristic wavelength with an intensity proportional to the quantity of the at least one selected component in the sample; and
   b. selectively detecting infrared radiation emitted at the at least one characteristic wavelength and generating an output signal representative thereof, and thereby determining the quantity of the at least one selected component in the sample.

6. A method according to claim 5, including the step of discriminating the at least one characteristic wavelength by allowing only the at least one characteristic wavelength to be detected in the detecting step while inhibiting the detection of other wavelengths.

7. A method according to claim 6, wherein said discriminating step includes separating the wavelengths of the emitted radiation into an infrared spectrum.

8. A method according to claim 6, wherein said discriminating step includes utilizing a monochromator.

9. A method according to claim 6, wherein said discriminating step includes utilizing an interferometer.

10. A method according to claim 9, wherein said discriminating step includes utilizing a computer coupled to the interferometer for performing a Fourier transform analysis on an output signal from the interferometer to thereby obtain a spectral analysis characteristic of the sample.

11. A method according to claim 5, further including utilizing a computer for performing signal processing on the output signal produced by said detecting step to provide an output indicative of the quantity of the at least one selected component present in the sample.

12. A method according to claim 5, including vaporizing a liquid sample and utilizing the resultant vapors in said exciting step.

13. A method according to claim 5, wherein said exciting step includes generating said flame fueled by hydrogen/air or hydrogen/oxygen.

14. A method according to claim 5, wherein the at least one selected component or the at least one selected substance contains carbonates or calcinates, further including acidifying the at least one selected component or the at least one selected substance to generate $CO_2$ therefrom, and utilizing the $CO_2$ so generated in the exciting step.

15. A method according to claim 5, wherein the at least one selected component or the at least one selected substance contains carbon-containing compounds, further including oxidizing the at least one selected component or the at least one selected substance to generate $CO_2$ therefrom, and utilizing the $CO_2$ so generated in the exciting step.

16. A method according to claim 5, wherein the at least one selected component or the at least one selected substance contains hypochlorous acid or hypochlorite ions, further including acidifying the at least one selected component or the at least one selected substance with HCl to generate $Cl_2$ therefrom, and utilizing the $Cl_2$ so generated in the exciting step, wherein said flame is a hydrogen/air or hydrogen/oxygen flame.

17. A method according to claim 5, wherein the at least one selected component or the at least one selected substance contains chloride ions, further including oxidizing and acidifying the at least one selected component or the at least one selected substance to generate chlorine $Cl_2$ therefrom, and utilizing the $Cl_2$ so generated in the exciting step, wherein said flame is a hydrogen/air or hydrogen/oxygen flame.

18. A method according to claim 5, wherein the at least one selected component of the sample or the at least one selected substance includes carbon-containing compounds, and said exciting step includes generating said flame, and oxidizing the at least one selected component of the sample or the at least one selected substance in the flame to generate $CO_2$ therefrom, and utilizing the $CO_2$ so generated in the exciting step.

19. A method according to claim 5, wherein the at least one selected component or the at least one selected substance includes chlorine-containing organic compounds, and said exciting step includes generating said flame, and combusting the at least one selected component or the at least one selected substance in the flame to thereby generate HCl therefrom, and utilizing the HCl so generated in the exciting step.

20. A method according to claim 5, wherein the at least one selected component or the at least one selected substance includes fluorine-containing organic compounds, and said exciting step includes generating said flame, and combusting the at least one selected component or the at least one selected substance in the flame to thereby generate HF therefrom, and utilizing the HF so generated in the exciting step.

21. Apparatus for detecting and making quantitative measurements of at least one selected component in a sample, in which at least one selected component of the sample, or at least one selected substance produced from the at least one selected component in the sample and characteristic of the at least one selected component, is introduced into an exciting means, and when the at least one selected component is present in the sample, gas-phase, infrared-active molecules emit infrared radiation at at least one characteristic wavelength in proportion to the quantity of the at least one selected component in the sample, comprising:
  a. flame means for exciting the gas-phase, infrared-active molecules with a flame to emit radiation along a first path, wherein when the at least one selected component is present in the sample, the gas-phase, infrared-active molecules emit radiation at at least one characteristic wavelength with an intensity proportional to the quantity of the at least one selected component in the sample, and wherein the exciting means simultaneously emits fluctuating background radiation along said first path at the at least one characteristic wavelength of the gas-phase, infrared-active molecules and at other wavelengths,
  b. beam splitting means disposed on said first path for directing a portion of the emitted radiation over a second path;
  c. first and second infrared detector means located on said first and second paths respectively, wherein said first detector means generates a first electrical signal responsive to emitted radiation at the at least one characteristic wavelength, and said second detector means generates a second electrical signal responsive to the simultaneously emitted background radiation;
  d. first wavelength discriminating means located on said first path between said beam splitting means and said first detector means, and second wavelength discriminating means located on said second path between said beam splitting means and said second detector means, wherein said first wavelength discriminating means allows passage of radiation at the at least one characteristic wavelength and inhibits the passage of other wavelengths, and said second wavelength discriminating means allows passage of the emitted background radiation and inhibits the passage of radiation at the at least one characteristic wavelength; and
  e. means connected to said first and second detector means for combining the first and second electrical signals to thereby cause a cancellation of fluctuations in intensity at the at least one characteristic wavelength caused by fluctuations in the background radiation.

22. Apparatus according to claim 21, wherein said means for combining includes means for subtracting the second electrical signal from the first electrical signal.

23. Apparatus according to claim 21, further including optical attenuating means, located on said second path between said beam splitting means and said second detector means, for adjusting the level of the second output signal.

24. Apparatus according to claim 21, wherein said first and second detector means are coupled to a biasing circuit means for achieving equalization of the first and second output signals.

25. Apparatus for detecting and making quantitative measurements of at least one selected component in a sample, in which at least one selected component of the sample, or at least one selected substance produced from the at least one selected component in the sample and characteristic of the at least one selected component, is introduced into an exciting means, and when the at least one selected component is present in the sample, gas-phase infrared-active molecules emit infrared radiation at at least one characteristic wavelength in proportion to the quantity of the at least one selected component in the sample, comprising:
  a. flame means for exciting the gas-phase, infrared-active molecules with a flame to emit radiation over a first path, wherein when the at least one selected component is present in the sample, the gas-phase, infrared-active molecules emit radiation at at least one characteristic wavelength with an intensity proportional to the quantity of the at least one selected component in the sample; and
  b. infrared discriminating and detector means located on said given path for detecting infrared radiation at the at least one characteristic wavelength and for generating an output signal representative thereof, and thereby determining the quantity of the at least one selected component in the sample.

26. Apparatus according to claim 25, wherein said infrared discriminating and detector means includes wavelength discriminating means located on said path, between the exciting means and the infrared detector means, for allowing the at least one characteristic wavelength to pass from the exciting means to the detector means while inhibiting the passage of other wavelengths.

27. Apparatus according to claim 25, wherein said infrared discriminating and detector means includes means for separating the wavelength of the emitted radiation into an infrared spectrum.

28. Apparatus according to claim 25, wherein said infrared discriminating and detector means includes a monochromator.

29. Apparatus according to claim 25, further including a computer means, responsive to an output signal from the infrared detector means, for performing signal processing thereon to provide an output indicative of the quantity of the at least one selected component present in the sample.

30. Apparatus according to claim 25, wherein said infrared discriminating and detector means includes an interferometer.

31. Apparatus according to claim 30, further comprising a computer means, coupled to the interferometer, for performing a Fourier transform analysis on an output signal from the interferometer to thereby obtain a spectral analysis characteristic of the sample.

32. Apparatus according to claim 25, further including vaporizing means for vaporizing a liquid sample and for conducting the resultant vapors into said exciting means.

33. Apparatus according to claim 25, wherein said exciting means includes means for generating said flame fueled by hydrogen/air or hydrogen/oxygen.

34. Apparatus according to claim 25, wherein said infrared detector means includes a thermal infrared detector.

35. Apparatus according to claim 25, wherein said infrared detector means includes a quantum detector.

36. Apparatus according to claim 25, wherein the at least one selected component or the at least one selected substance contains carbonates or calcinates, further including means for acidifying the at least one selected component or the at least one selected substance to generate $CO_2$ therefrom, wherein the $CO_2$ so generated is introduced into the exciting means.

37. Apparatus according to claim 25, wherein the at least one selected component or the at least one selected substance contains carbon-containing compounds, further including means for oxidizing the at least one selected component or the at least one selected substance to generate $CO_2$ therefrom, wherein the $CO_2$ so generated is introduced into the exciting means.

38. Apparatus according to claim 25, wherein the at least one selected component or the at least one selected substance contains hypochlorous acid or hypochlorite ions, further including means for acidifying the at least one selected component or the at least one selected substance with HCl to generate $Cl_2$ therefrom, wherein the $Cl_2$ so generated is introduced into the exciting means, said exciting means including a hydrogen/air or hydrogen/oxygen flame.

39. Apparatus according to claim 25, wherein the at least one selected component or the at least one selected substance contains chloride ions, further including means for oxidizing and acidifying the at least one selected component or the at least one selected substance to generate chlorine $Cl_2$ therefrom, wherein the $Cl_2$ so generated is introduced into the exciting means, said exciting means including a hydrogen/air or hydrogen/oxygen flame.

40. Apparatus according to claim 25, wherein the at least one selected component of the sample or the at least one selected substance includes carbon-containing compounds, and said exciting means includes a flame generating means for oxidizing the at least one selected component of the sample or the at least one selected substance to generate $CO_2$ therefrom, wherein the $CO_2$ so generated is introduced into the exciting means.

41. Apparatus according to claim 25, wherein the at least one selected component or the at least one selected substance includes chlorine-containing organic compounds, and said exciting means includes a flame generating means for combusting the at least one selected component or the at least one selected substance to thereby generate HCl therefrom, wherein the HCl so generated is introduced into the exciting means.

42. Apparatus according to claim 25, wherein the at least one selected component or the at least one selected substance includes fluorine-containing organic compounds, and said exciting means includes a flame generating means for combusting the at least one selected component or the at least one selected substance to thereby generate HF therefrom, wherein the HF so generated is introduced into the exciting means.

* * * * *

UNITED STATES PATENT AND TRADEMARK OFFICE
CERTIFICATE OF CORRECTION

Page 1 of 2

PATENT NO. : 5,246,868
DATED : September 21, 1993
INVENTOR(S) : Busch, et. al.

It is certified that error appears in the above-indentified patent and that said Letters Patent is hereby corrected as shown below:

In claim 1, line 15, column 55, delete the comma "," and substitute a semicolon --;--, therefore.

In claim 5, line 63, column 55, immediately after the first 'at', insert --the--, therefore.

In claim 21, line 44, column 57, delete the comma "," and substitute a semicolon --;--, therefore.

In claim 21, line 46, column 57, immediately after 'emitted', insert --infrared--, therefore.

In claim 25, line 33, column 58, delete "first" and substitute --given--, therefore.

In claim 25, line 36, column 58, immediately after the first 'at', insert --the--, therefore.

In claim 26, line 48, column 58, immediately after the first 'the', insert --flame--, therefore.

In claim 27, line 55, column 58, delete "wavelength" and substitute --wavelengths--, therefore.

In claim 38, line 32, column 59, immediately after '25', delete the period "." and substitute a comma --,--, therefore.

UNITED STATES PATENT AND TRADEMARK OFFICE
CERTIFICATE OF CORRECTION

PATENT NO. : 5,246,868
DATED : September 21, 1993
INVENTOR(S) : Busch, et. al.

It is certified that error appears in the above-indentified patent and that said Letters Patent is hereby corrected as shown below:

In Claim 38, line 32, column 59, immediately after '25', delete the period "." and substitute a comma --,--, therefore.

Signed and Sealed this

Nineteenth Day of July, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO.    :   5,246,868

DATED         :   September 21, 1993

INVENTOR(S)   :   Kenneth W. Busch *et al.*

It is certified that error appears in the above-identified patent and that said Letters Patent is hereby corrected as shown below:

Title page,
On the first column of the cover page, after item [73] Assignee: replace "Research Corporation Technologies, Inc. Tucson, Ariz." with --Baylor University, Waco, Texas--.

Signed and Sealed this

Eleventh Day of October, 1994

Attest:

BRUCE LEHMAN

Attesting Officer

Commissioner of Patents and Trademarks